US009994630B2

(12) United States Patent
Berry et al.

(10) Patent No.: US 9,994,630 B2
(45) Date of Patent: Jun. 12, 2018

(54) CLOSTRIDIUM DIFFICILE ANTIBODIES

(71) Applicant: Cangene Corporation, Winnipeg (CA)

(72) Inventors: Jody Berry, Carlsbad, CA (US); Darrell Johnstone, Winnipeg (CA); Joyee Antony George, Winnipeg (CA); Bonnie Tighe, Winnipeg (CA)

(73) Assignee: CANGENE CORPORATION, Winnipeg Manitoba (CA)

(*) Notice: Subject to any disclaimer, the term of this patent is extended or adjusted under 35 U.S.C. 154(b) by 0 days. days.

(21) Appl. No.: 15/338,990

(22) Filed: Oct. 31, 2016

(65) Prior Publication Data

US 2017/0051047 A1 Feb. 23, 2017

Related U.S. Application Data

(63) Continuation of application No. 13/592,286, filed on Aug. 22, 2012, now Pat. No. 9,505,847.

(60) Provisional application No. 61/526,031, filed on Aug. 22, 2011.

(51) Int. Cl.

| | |
|---|---|
| ***C07K 16/40*** | (2006.01) |
| ***C07K 16/12*** | (2006.01) |
| ***A61K 39/40*** | (2006.01) |
| ***A61K 45/06*** | (2006.01) |
| *A61K 39/00* | (2006.01) |

(52) U.S. Cl.

CPC .......... *C07K 16/1282* (2013.01); *A61K 39/40* (2013.01); *A61K 45/06* (2013.01); *C07K 16/40* (2013.01); *A61K 2039/505* (2013.01); *C07K 2317/14* (2013.01); *C07K 2317/24* (2013.01); *C07K 2317/33* (2013.01); *C07K 2317/51* (2013.01); *C07K 2317/515* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 5,231,003 A | 7/1993 | Coughlin et al. | |
| 5,736,139 A * | 4/1998 | Kink .................... | C07K 14/245 424/164.1 |
| 6,667,035 B1 * | 12/2003 | Von Eichel-Streiber ...... | C07K 14/33 424/130.1 |
| 7,597,891 B2 | 10/2009 | Simon | |
| 8,236,311 B2 * | 8/2012 | Ambrosino ............ | A61K 39/08 424/141.1 |
| 9,274,119 B2 | 3/2016 | Aburatani et al. | |
| 9,505,847 B2 * | 11/2016 | Cassan ............... | C07K 16/1282 |
| 2004/0137601 A1 | 7/2004 | Von Eichel-Streiber et al. | |
| 2005/0287150 A1 | 12/2005 | Ambrosino et al. | |
| 2007/0071763 A1 | 3/2007 | Burnie et al. | |
| 2007/0231333 A1 | 10/2007 | Boghaert et al. | |
| 2009/0087478 A1 | 4/2009 | Hansen et al. | |
| 2009/0202556 A1 | 8/2009 | Ohta et al. | |
| 2009/0269336 A1 | 10/2009 | Hong et al. | |
| 2009/0280116 A1 | 11/2009 | Smith et al. | |
| 2010/0233181 A1 | 9/2010 | Ambrosino et al. | |
| 2010/0233182 A1 | 9/2010 | Ambrosino et al. | |

FOREIGN PATENT DOCUMENTS

| | | | |
|---|---|---|---|
| EP | 1613655 | A1 | 1/2006 |
| JP | 2007-533330 | A | 11/2007 |
| JP | 2008-516970 | A | 5/2008 |
| JP | 2009-529578 | A | 8/2009 |
| JP | 2010-511388 | A | 4/2010 |
| WO | 2006/044643 | A2 | 4/2006 |
| WO | 2006/071877 | A2 | 7/2006 |
| WO | 2006/121422 | A2 | 11/2006 |
| WO | 2007/070569 | A2 | 6/2007 |
| WO | 2007/106744 | A2 | 9/2007 |
| WO | 2009/087978 | A1 | 7/2009 |
| WO | 2011/067616 | A1 | 6/2011 |
| WO | 2011130650 | A2 | 10/2011 |

OTHER PUBLICATIONS

Marozsan et al., "Protection against Clostridium difficile infection with broadly neutralizing antitoxin monoclonal antibodies", J Infect Dis, Sep. 1, 2012, pp. 706-713, vol. 206, No. 5.

Lyerly et al., "Characterization of Toxins A and B of Clostridium difficile with Monoclonal Antibodies", Infect Immun, Oct. 1986, pp. 70-76, vol. 54, No. 1.

Lowy et al., "Treatment with monoclonal antibodies against Clostridium difficile toxins", N Engl J Med, Jan. 21, 2010, pp. 197-205, vol. 362, No. 3.

Kink et al., "Antibodies to Recombinant Clostridium difficile Toxins A and B Are an Effective Treatment and Prevent Relapse of C.difficile Associated Disease in a Hamster Model of Infection", Infect Immun, May 1998, pp. 2018-2025, vol. 66, No. 5.

Kamiva et al., "Production of monoclonal antibody to Clostridium difficile toxin A which neutralizes enterotoxicity but not haemagglutination activity", FEMS Microbiol Lett, Jul. 1, 1991, pp. 311-315, vol. 65, No. 3 (No PDF).

International Search Report and Written Opinion for PCT/US2012/051948 dated Jan. 23, 2013.

International Preliminary Report on Patentability for PCT/US2012/051948 dated Mar. 6, 2014.

Hussack et al., "Toxin-Specific Antibodies for the Treatment of Clostridium Difficile: Current Status and Future Perspectives", Toxins, Molecular Diversity Preservation International (MDPI), May 7, 2010, pp. 998-1018, vol. 2, No. 5.

Hussack et al., "Neutralization of Clostridium difficile toxin A with single-domain antibodies targeting the cell receptor binding domain", J Biol Chem, Mar. 18, 2011, pp. 8961-8976, vol. 286, No. 11.

(Continued)

*Primary Examiner* — Mary Maille Lyons

(74) *Attorney, Agent, or Firm* — Thompson Coburn LLP

(57) ABSTRACT

Compositions and methods for the treatment or prevention of *Clostridium difficile* infection in a subject are provided. The compositions comprise antibodies to *Clostridium difficile* toxin A. The methods provide for administering the antibodies to a subject in an amount effective to reduce or eliminate or prevent relapse from *Clostridium difficile* bacterial infection.

16 Claims, 43 Drawing Sheets

(56) References Cited

OTHER PUBLICATIONS https://Lirias.kuleuven.be/handle/123456789/350999, "In Vitro and In Vivo Characterization of Neutralizing Monoclonal Antibodies Against Clostridium Difficile Toxins A and B", Sep. 21, 2012.

Guo et al., "Protein Tolerance to Random Amino Acid Change", Proceedings of the National Academy of Sciences USA, 2004, pp. 9205-9210, vol. 101 No. 5.

Greenspan et al., "Defining Epitopes: It's Not Easy as it Seems", Nature Biotechnology, 1999, pp. 936-937, vol. 17.

Giannasca et al., "Serum antitoxin antibodies mediate systemic and mucosal protection from Clostridium difficile disease in hamsters", Infect Immun, Feb. 1999, pp. 527-538, vol. 67, No. 2.

Frey et al., "Localization of Two Epitopes Recognized by Monoclonal Antibody PCG-4 on Clostridium difficile Toxin A", Infect Immun, Jun. 1992, pp. 2488-2492, vol. 60, No. 6.

Demarest et al., "Neutralization of Clostridium difficile toxin A using antibody combinations", Mabs, Mar.-Apr. 2010, pp. 190-198, vol. 2, No. 2.

Correspondence re Lowly et al., "Treatment with monoclonal antibodies against Clostridium difficile toxins", N Engl J Med, Apr. 15, 2010, pp. 1444-1446, vol. 362, No. 15.

Babcock et al., "Human Monoclonal Antibodies Directed against Toxins A and B Prevent Clostridium difficile-induced mortality in Hamsters", Infect Immun Nov. 2006, pp. 6339-6347, vol. 74, No. 11.

Office Action for U.S. Appl. No. 13/592,286 dated Mar. 1, 2016.

* cited by examiner

Figure 1
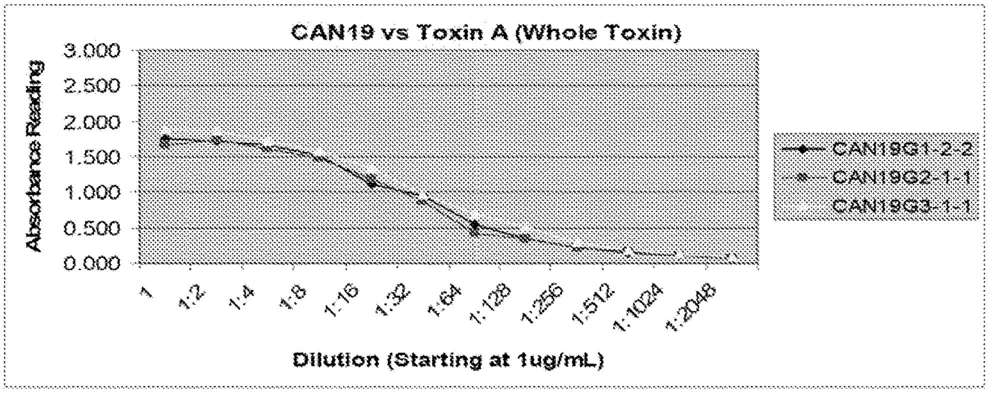
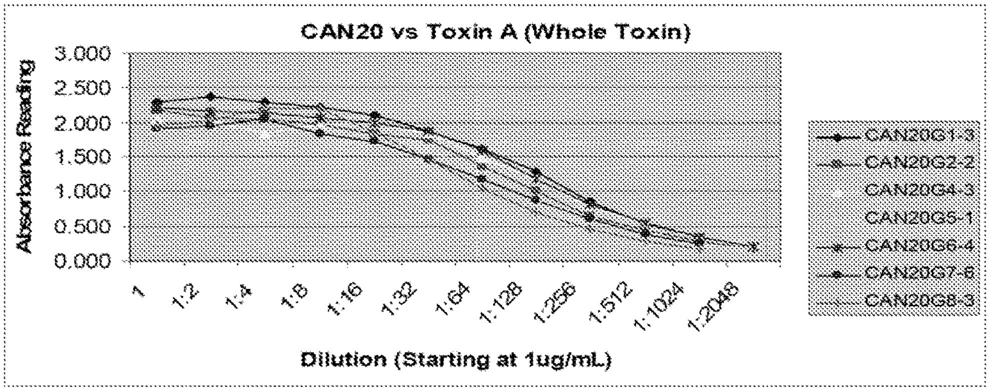

Figure 4
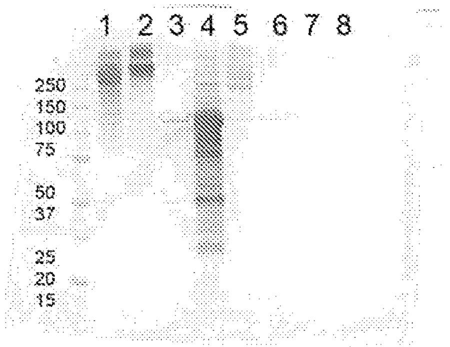
Blot A: Probed with CAN19G1 at 0.5 μg/ml protein loaded at 2 μg
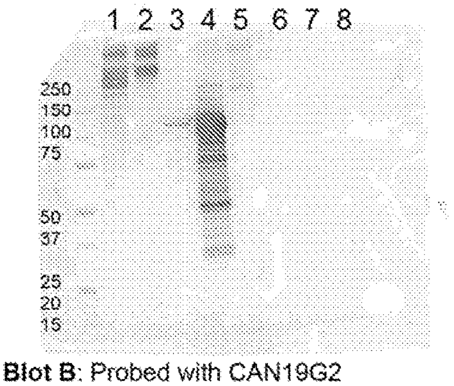
Blot B: Probed with CAN19G2 at 0.5 μg/ml protein loaded at 2 μg
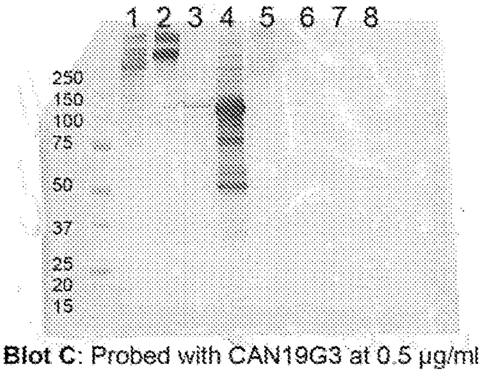
Blot C: Probed with CAN19G3 at 0.5 μg/ml protein loaded at 2 μg
1. Toxin A
2. Toxoid A
3.
4. Toxin A Fragment 4
5. Toxin B
6.
7. Toxin B Fragment 4
8. PilF (negative CNT)

Figure 10

| Primer Name | Category | Primer Sequence |
|---|---|---|
| 5'mVK-Lead-1 | Subgroup Specific | GGTGCAGATTTTCAGCTTCC |
| 3'KappaConstRT | | GTGCTGTCTTTGCTGTCCTG |
| 5'mVH-Lead-2 | | BTNCTYYTCTKCCTGRT |
| 5'mVH-Lead-2A | | TGGSTGTGGAMCTTGCTATT |
| 3'mIG1-2C RT | | AGGASAGCTGGGAAGGTGTG |
| 5'mVK-Lead-3 | Non-Subgroup Specific | CTWKGRSTKCTGCTKYTCTG |
| 5'mVK-Lead-3A | | CCTGTTAGGCTGTTGGTGCT |
| 5'mVH-IGHV1-Lead | | RKCARCARCTRCAGGTGTCC |
| 5'mVH-Lead-1 | | CCYWNTTTTAMAWGGTGTCCAKTGT |
| 5'mVH-Lead-3 | | GGATGGAGCTRTATCATBCTC |
| 5'mVH-Lead-4 | | GRTCTTTMTYTTHHTCCTGTCA |
| 5'mVH-Lead-5 | | VCCTTWMMTGGTATCCWGTST |

W = A or T
S = C or G
R = A or G
Y = C or T
K = G or T
M = A or C
B = C, G, or T (not A)
D = A, G, or T (not C)
H = A, C, or T (not G)
V = A, C, or G (not T)
N = A, C, G, or T

Figure 11

| | | | |
|---|---|---|---|
| **Result summary:** | **Productive IGK rearranged sequence** (no stop codon and in-frame junction) | | |
| V-GENE and allele | Musmus IGKV4-74*01 | score = 1324 | identity = **96,81%** (273/282 nt) |
| J-GENE and allele | Musmus IGKJ1*01 | score = 180 | identity = 100,00% (36/36 nt) |
| FR-IMGT lengths, CDR-IMGT lengths and AA JUNCTION | [26.17.36.10] | [7.3.9] | CLQYHRSPRTF |

Figure 12

```
       FR1-IMGT           CDR1-IMGT    FR2-IMGT    CDR2-IMGT          FR3-IMGT               CDR3-IMGT  FR4-IMGT
        (1-26)             (27-38)      (39-55)     (56-65)           (66-104)               (105-117)  (118-128)
   A            B            BC        C       C'     C'C"     C"      D        E        F        FG         G
(1-15)       (16-26)      (27-38)  (39-46) (47-55) (56-65) (66-74) (75-84)  (85-96)  (97-104) (105-117) (118-128)
-------------> ----------->         -------> -------->        -------> -------> ---------> ------->          ---------->
1       10  15 16   23 26 27      38 3941  46 47     55 56     65 66     74 75  80 84 85  89   96 97  104 105 11112 117 118    128
|........|....| |......|..| |..........| |.|....| |.......| |........| |.......| |....|...| |..|.......| |......| |.....||....| |.........|
vh                   QIQLVQSGP.EVKKP GETVKISCKAS GYTF....TNQG MNWVKQAP GKGLKWMGW INTN..TGEP TYTEEFK.G RFAFSLETSA STAYLQINNLKN EDTATYFC YVNYDY..YTMDF WGQGTSVTVSS
IGHV7-4-1*02         QVQLVQSGS.ELKKP GASVKVSCKAS GYTF....TSYA MNWVRQAP GQGLEWMGW INTN..TGNP TYAQGFT.G RFVFSLDTSV STAYLQISSLKA EDTAVYYC AR  YYYYYGMDV WGQGTTVTVSS
(Homo sapiens)       I    P V   ET I         NQG    K    K K          E   TEE K   A  E A      NN N    T F YV D   T F    S

|--------------------------------------------V-REGION--------------------------------------------||N-||--------J-REGION--------|
                                                                                                          IGHJ6*01
```

```
         FR1-IMGT           CDR1-IMGT      FR2-IMGT     CDR2-IMGT           FR3-IMGT                 CDR3-IMGT
FR4-IMGT
          (1-26)             (27-38)        (39-55)      (56-65)            (66-104)                 (105-117)
(118-128)
     A            B            BC          C        C'      C'C"      C"      D         E        F        FG
G
  (1-15)       (16-26)      (27-38)    (39-46)  (47-55)  (56-65)  (66-74) (75-84)  (85-96)  (97-104)  (105-117)
(118-128)
-------------> ----------->               -------> -------->          -------> --------> ---------> ------->
----------->
1       10  15 16   23 26 27      38 3941  46 47     55 56     65 66     74 75  80 84 85  89   96 97  104 105 11112
117 118    128
|........|....| |......|..| |..........| |.|....| |.......| |........| |.......| |....|...| |..|.......| |......|
|.....||....| |.........|
vk                  .VVLTQSPAIMSASL GDRVTMTCTAS SSVI.....STY LHWYQQKP GSSPKLWIY ST.......S TLASGVP.P RFSGSG..SG TSYSLTISSMEA EDAATYYC
                    LQYHR....SFRT FGGGTKLEIK.
IGKV1-39*01         DIQMTQSPSSLSASV GDRVTITCRAS QSI......SSY LNWYQQKP GKAPKLLIY AA.......S SLQSGVP.S RFSGSG..SG TDFTLTISSLQP EDFATYYC QQSYSTP
                    LT FGGGTKVEIK.
(Homo sapiens)       VVL   AIM  L    M  T   S V      T   H       SS   W  ST        T A    P           SYS    MEA  A     L YHR    R
                    L

|--------------------------------------------V-REGION--------------------------------------------
||||-J-REGION-|

     IGKJ4*01
```

Figure 13a

IGVH

CAN20G2 Heavy
Closest Human framework insertion.
Kozak Seq and HAVT20 Leader
IGHV7-4-1*02
CAN20G CDRs
IGHJ6*01
Altered HpaI GTT-AAC RE site for cloning

```
<--------------------------------------------------------------Kozak Seq and HAVT20 Leader------------------------------
GCCGCCACCATGGCATGCCCTGGCTTCCTGTGGGCACTTGTGATCTCCACCTGTCTT

-------------------------------><-----------------------------------------------FR1----------------------------------------
GAATTTTCCATGGCTCAGGTGCAGCTGGTGCAATCTGGGTCTGAGTTGAAGAAGCC

---------------------------------------------------------------------------------><----------------------CDR1-------------------
TGGGGCCTCAGTGAAGGTTTCCTGCAAGGCTTCTGGGTATACCTTCACAAACCAAG

----><-------------------------------------------------------FR2---------------------------------------------------------><----
GAATGAATTGGGTGCGACAGGCCCCTGGACAAGGGCTTGAGTGGATGGGATGGAT

------------------CDR2-----------------------><------------------------------------------------------------------------------
AAACACCAACACTGGAGAGCCAACGTATGCCCAGGGCTTCACAGGACGGTTTGTC

-------------------------------------------------------------------FR3----------------------------------------------------------
TTCTCCTTGGACACCTCTGTCAGCACGGCATATCTGCAGATCAGCAGCCTAAAGGC

-------------------------------------------------------><----------------------------------CDR3------------------------------
TGAGGACACTGCCGTGTATTACTGTTATGTCAATTACGATTATTATACTATGGACTT

-><-----------------------------------------FR4---------------------------->
CTGGGGGCAAGGGACCACGGTCACCGTCTCCTCA
```

Translation:

```
<---------------------------FR1------------------------------><----CDR1------><--------------------FR2---------------------><---
Q V Q L V Q S G S E L K K P G A S V K V S C K A S G Y T F T N Q G M N W V R Q A P G Q G L E W M G W I N

---CDR2--><------------------------------------------------FR3------------------------------------- ><----------CDR3--------
T N T G E P T Y A Q G F T G R F V F S L D T S V S T A Y L Q I S S L K A E D T A V Y Y C Y V N Y D Y Y T M D

-><-------------FR4------>
F W G Q G T T V T V S S
```

CAN20G2 Kappa
IGKV1D-39*01
CAN20G2 CDRs
IGKJ4*01

<----------------------------------------------------------------Kozak Seq and HAVT20 Leader------------------------------------
GCCGCCACCATGGCATGCCCTGGCTTCCTGTGGGCACTTGTGATCTCCACCTGTCTT ---------------------------------><---------------------------------------------------------FR1---------------------------------------------
GAATTTTCCATGGCTGACATCCAGATGACCCAGTCTCCATCCTCCCTGTCTGCATCT ---------------------------------------------------------------------------------------><-------------------CDR1---------------------
GTAGGAGACAGAGTCACCATCACTTGCCGGGCAAGTTCAAGTGTAATTTCCACTTA -><------------------------------------------------------------FR2---------------------------------------------------------------><---------
CTTAAATTGGTATCAGCAGAAACCAGGGAAAGCCCCTAAGCTCCTGATCTATAGCA --CDR2-><----------------------------------------------------------------------FR3-------------------------------------------------------
CATCCAGTTTGCAAAGTGGGGTCCCATCAAGGTTCAGTGGCAGTGGATCTGGGACA -----------------------------------------------------------------------------------------------------------------------------------------------------
GATTTCACTCTCACCATCAGCAGTCTGCAACCTGAAGATTTTGCAACTTACTACTG -><------------------------------CDR3-----------------------------><------------------------------------FR4----------------------------
TCTCCAGTATCACCGTTCCCCACGGACGTTCGGCGGAGGGACCAAGGTGGAGATCA

----->
AA

Translation:

<--------------------------------------------FR1-------------------------------------><-----CDR1-----><---------------FR2----------
D I Q M T Q S P S S L S A S V G D R V T I T C R A S S S V I S T Y L N W Y Q Q K P G

-------------------------><CDR2><---------------------------------------------FR3------------------------------------------
K A P K L L I Y S T S S L Q S G V P S R F S G S G S G T D F T L T I S S L Q P E

------------------------><------------CDR3-------------><---------------FR4--------------->
D F A T Y Y C L Q Y H R S P R T F G G G T K V E I K

Figure 14a

CAN20G2 Heavy Total: 8 Resurfaced AA
Kozak and HAVT20 Leader
CAN20G2 Framework Sequence
CAN20G2 CDR <------------------------------------------Kozak and HAVT20 Leader------------------------------
GCCGCCACCATGGCATGCCCTGGCTTCCTGTGGGCACTTGTGATCTCCACCTGTCTT --------------------------><--------------------------------------FR1--------------------------------------
GAATTTTCCATGGCTCAGATCCAGTTGGTGCAGTCTGGACCTGAGCTGAAGAAGCC ---------------------------------------------------------------------><-------------------CDR1--------------------
TGGAGAGACAGTCAAGATCTCCTGCAAGGCTTCTGGGTATACCTTCACAAACCAAG ---><---------------------------------------------------FR2-------------------------------------------><----
GAATGAACTGGGTGAAACAGGCTCCAGGAAAGGGTTTAAAGTGGATGGGCTGGAT -----------------CDR2-----------------><----------------------------------------------------------------------
AAACACCAACACTGGAGAGCCAACATATACTGCCGATTTCACAGGACGGTTTGCC ----------------------------------------------------------FR3-------------------------------------------------------
TTCTCTTTAGAAACCTCTGTGAGCACTGCCTATTTGCAGATCAACTCCCTCAAAGC
TGAGGACACGGCTACATATTTCTGTTATGTCAATTACGATTATTATACTATGGACT ---------------------------------------------------><-------------------------------CDR3-------------------------

---><---------------------------FR4------------------------------------>
TCTGGGGTCAAGGAACCCTGGTCACCGTCTCCTCA

Translation:

<----------------------------FR1-------------------------><------CDR1----><---------------------FR2-------------------><---
QIQLVQSGPELKKPGETVKISCKASGYTFTNQGMNWVKQAPGKGLKWMGWIN

--CDR2---><-----------------------------------FR3---------------------------------------><----------CDR3------
TNTGEPTYTADFTGRFAFSLETSVSTAYLQINSLKAEDTATYFCYVNYDYYTM

---><-------------FR4---------->
DFWGQGTLVTVSS

Figure 14b

CAN20G2 Kappa Total: 7 Resurfaced AA

<----------------------------------------Kozak and HAVT20 Leader----------------------------------------
GCCGCCACCATGGCATGCCCTGGCTTCCTGTGGGCACTTGTGATCTCCACCTGTCTT ------------------------><----------------------------------------FR1----------------------------------------
GAATTTTCCATGGCTGACGTTCAGCTCACCCAGTCTCCAAGCATCATGTCTGCATC --------------------------------------------------------------------><------------CDR1------------
TCTAGGGGATCGGGTCACCATGACCTGCACTGCCAGCTCAAGTGTAATTTCCACTT ---><-----------------------------------------FR2-----------------------------------------><-----
ACTTGCACTGGTATCAGCAGAAGCCAGGATCCTCCCCCAAACTCTGGATTTATAGC ---CDR2---><------------------------------------------------------------------------------------
ACATCCACCCTGGCTTCTGGAGTCCCAAGCCGCTTCAGTGGCAGTGGGTCTGGGAC -----------------------------------------------FR3-----------------------------------------------
CGACTACTCTCTCACAATCAGCAGCATGGAGCCTGAAGATGCTGCCACTTATTACT ----><--------------------CDR3--------------------><----------------------FR4----------------------
GCCTCCAGTATCACCGTTCCCCACGGACGTTCGGTGGAGGCACCAAGGTGGAAAT

---------->
CAAA

Translation:

<------------------------------FR1------------------------------><-------CDR1------><---------
D V Q L T Q S P S I M S A S L G D R V T M T C T A S S S V I S T Y L H W

-----------------FR2-----------------><CDR2><------------------------FR3------------------------
Y Q Q K P G S S P K L W I Y S T S T L A S G V P P R F S G S G S G T D Y S

------------------------------------------><-----------CDR3--------><-----------FR4----------->
L T I S S M E P E D A A T Y Y C L Q Y H R S P R T F G G G T K V E I K

Figure 15

CAN20G2 Heavy Resurfaced

GCCGCCACCATGGCATGCCCTGGCTTCCTGTGGGCACTTGTGATCTCCACCTGTCTTGAATTTTCCATG

<--------------------FR1------------------------------------------------------------------------------------------

GCTCAGATCCAGTTGGTGCAGTCTGGACCTGAGCTGAAGAAGCCTGGAGAGACAGTCAAGATCTCCT

------------------><------------------CDR1------------------><-------------------------FR2-------------------------------

GCAAGGCTTCTGGGTATACCTTCACAAACCAAGGAATGAACTGGGTGAAACAGGCTCCAGGAAAGGG

----------------------------------><--------------------CDR2------------------><---------------------FR3---------------------

TTTAAAGTGGATGGGCTGGATAAACACCAACACTGGAGAGCCAACATATACTGCCGATTTCACAGGA

-----------------------------------------------------------------------------------------------------------------------------------

CGGTTTGCCTTCTCTTTAGAAACCTCTGTGAGCACTGCCTATTTGCAGATCAACTCCCTCAAAGCTGA

----------------------------------------><--------------------------CDR3-------------------------><-----------FR4-----------

GGACACGGCTACATATTTCTGTTATGTCAATTACGATTATTATACTATGGACTTCTGGGGTCAAGGAAC

------------------------------------->

CCTGGTCACCGTCTCCTCAGGTGAGTGCGGCCGCGAGCCCAGACACTGGACGCTGAACCTCGCGGAC
AGTTAAGAACCCAGGGGCCTCTGCGCCCTGGGCCCAGCTCTGTCCCACACCGCGGTCACATGGCACCA
CCTCTCTTGCAGCCTCCACCAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCCTCAG
GACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAGAGTTGGTGAGAGGCCAGCA
CAGGGAGGGAGGGTGTCTGCTGGAAGCCAGGCTCAGCGCTCCTGCCTGGACGCATCCCGGCTATGCAG
TCCCAGTCCAGGGCAGCAAGGCAGGCCCCGTCTGCCTCTTCACCCGGAGGCCTCTGCCCGCCCCACTC
ATGCTCAGGGAGAGGGTCTTCTGGCTTTTTCCCCAGGCTCTGGGCAGGCACGGGCTAGGTGCCCCTAA
CCCAGGCCCTGCACACAAAGGGGCAGGTGCTGGGCTCAGACCTGCCAAGAGCCATATCCGGGAGGAC
CCTGCCCCTGACCTAAGCCCACCCCAAAGGCCAAACTCTCCACTCCCTCAGCTCGGACACCTTCTCTCC
TCCCAGATTCCAGTAACTCCCAATCTTCTCTCTGCAGAGCCCAAATCTTGTGACAAAACTCACACAT
GCCCACCGTGCCCAGGTAAGCCAGCCCAGGCCTCGCCCTCCAGCTCAAGGCGGGACAGGTGCCCTAG
AGTAGCCTGCATCCAGGGACAGGCCCCAGCCGGGTGCTGACACGTCCACCTCCATCTCTTCCTCAGCA
CCTGAACTCCTGGGGGGACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAA
GTTCAACTGGTACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATCTCCA
AAGCCAAAGGTGGGACCCGTGGGGTGCGAGGGCCACATGGACAGAGGCCGGCTCGGCCCACCCTCTG
CCCTGAGAGTGACCGCTGTACCAACCTCTGTCCCTACAGGGCAGCCCCGAGAACCACAGGTGTACA
CCCTGCCCCCATCCCGGGAGGAGATGACCAAGAACCAGGTCAGCCTGACCTGCCTGGTCAAAGG
CTTCTATCCCAGCGACATCGCCGTGGAGTGGGAGAGCAATGGGCAGCCGGAGAACAACTACAA
GACCACGCCTCCCGTGCTGGACTCCGACGGCTCCTTCTTCCTCTATAGCAAGCTCACCGTGGAC
AAGAGCAGGTGGCAGCAGGGGAACGTCTTCTCATGCTCCGTGATGCATGAGGCTCTGCACAACC
ACTACACGCAGAAGAGCCTCTCCCTGTCTCCGGGTAAATGATGAGCTAGC

Translation:

<--------------------FR1-----------------><--CDR1----><-------------FR2---------------><--CDR2--><------------------

QIQLVQSGPELKKPGETVKISCKASGYTFTNQGMNWVKQAPGKGLKWMGWINTNTGEPTYTADFTGRFA

---------FR3-----------------------------------><------CDR3------><-----FR4--------->

FSLETSVSTAYLQINSLKAEDTATYFCYVNYDYYTMDFWGQGTLVTVSS

Figure 16

CAN20G2 Kappa Resurfaced

ALTERED BamHI SITE ggaTCC→ggcAGC

<------------------------------------------------------------------Kozak and HAVT20 Leader-----------------------------------
GCCGCCACCATGGCATGCCCTGGCTTCCTGTGGGCACTTGTGATCTCCACCT ------------------------------------------------------><------------------------------------------FR1------------------------------------------
GTCTTGAATTTTCCATGGCTGACGTTCAGCTCACCCAGTCTCCAAGCATCAT ----------------------------------------------------------------------------------------------------------------------------><----CDR1---
GTCTGCATCTCTAGGGGATCGGGTCACCATGACCTGCACTGCCAGCTCAAGT ----------------------------------------><--------------------------------------------------FR2--------------------------------------------------
GTAATTTCCACTTACTTGCACTGGTATCAGCAGAAGCCAGGCAGCTCCCCCA -------------------------------------><------CDR2---------><------------------------------------------FR3-----------------------------------
AACTCTGGATTTATAGCACATCCACCCTGGCTTCTGGAGTCCCAAGCCGCTT -------------------------------------------------------------------------------------------------------------------------------------------
CAGTGGCAGTGGGTCTGGGACCGACTACTCTCTCACAATCAGCAGCATGGA ---------------------------------------------------------------------------------------><-------------------------------CDR3-----------------------------
GCCTGAAGATGCTGCCACTTATTACTGCCTCCAGTATCACCGTTCCCCACGG ------><-------------------------------------FR4------------------------------------->
ACGTTCGGTGGAGGCACCAAGGTGGAAATCAAACGTAAGTGCACTTTGCGGCCGCTAGGA
AGAAACTCAAAACATCAAGATTTTAAATACGCTTCTTGGTCTCCTTGCTATAATTATCTGGGATAAGCATGC
TGTTTTCTGTCTGTCCCTAACATGCCCTGTGATTATCCGCAAACAACACACCCAAGGGCAGAACTTTGTTAC
TTAAACACCATCCTGTTTGCTTCTTTCCTCAGGAACTGTGGCTGCACCATCTGTCTTCATCTTCCCGCCAT
CTGATGAGCAGTTGAAATCTGGAACTGCCTCTGTTGTGTGCCTGCTGAATAACTTCTATCCCAGAGAG
GCCAAAGTACAGTGGAAGGTGGATAACGCCCTCCAATCGGGTAACTCCCAGGAGAGTGTCACAGAGC
AGGACAGCAAGGACAGCACCTACAGCCTCAGCAGCACCCTGACGCTGAGCAAAGCAGACTACGAGAA
ACACAAAGTCTACGCCTGCGAAGTCACCCATCAGGGCCTGAGCTCGCCCGTCACAAAGAGCTTCAAC
AGGGGAGAGTGTTGATAGTTAACG Translation:

<-----------------------------------------FR1-----------------------------------------------><-------CDR1------><---------------
D V Q L T Q S P S I M S A S L G D R V T M T C T A S S S V I S T Y L H W Y

-----------------------FR2------------------><CDR2><----------------------------------FR3-----------------------------------
Q Q K P G S S P K L W I Y S T S T L A S G V P P R F S G S G S G T D Y S L

-------------------------------------------------------><-------------CDR3---------><---------------FR4------------->
T I S S M E P E D A A T Y Y C L Q Y H R S P R T F G G G T K V E I K R T VAAPSVFIFP
PSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Figure 17

Alignment with the closest gene and allele from the IMGT V domain directory: *All species* (All species)

```
                FR1-IMGT         CDR1-IMGT    FR2-IMGT      CDR2-IMGT            FR3-IMGT                    CDR3-IMGT     FR4-IMGT
                 (1-26)           (27-38)     (39-55)        (56-65)             (66-104)                    (105-117)     (118-128)
             A               B        BC        C      C'      C'C"      C"       D         E          F         FG           G
          (1-15)         (16-26)   (27-38)   (39-46) (47-55)  (56-65)  (66-74)  (75-84)  (85-96)    (97-104)   (105-117)    (118-128)
            ---------->  ------->            ------> ------>           ------>  ------>  ---------> ------->                 ---------->
            1         10   15 16   23 26 27         38 3941  46 47     55 56      65 66     74 75  80 84 85  89    96 97  104 105 11112 117 118     128
            |.......|....| |......|..| |..........| |.|....| |.......| |........| |.......| |...|...| |..|......| |......| |....||....| |.........|
Avastin     DIQMTQSPSSLSASV GDRVTITCSAS QDI......SNY LNWYQQKP GKAPKVLIY FT.......S SLHSGVP.S RFSGSG..SG TDFTLTISSLQP EDFATYYC QQYST....VPWT FGQGTKVEIK.
KappaChain
IGKV1D-     DIQMTQSPSSLSASV GDRVTITCQAS QDI......SNY LNWYQQKP GKAPKLLIY DA.......S NLETGVP.S RFSGSG..SG TDFTFTISSLQP EDIATYYC QQYDNLP    WT FGQGTKVEIK.
33*01
(Homo                            S                           V   FT          S HS                     L           F        ST
sapiens)
            |---------------------------------------------V-REGION---------------------------------------------------------||--J-REGION--|
                                                                                                                               IGKJ1*01
```

**Region(s) and domain(s) identified in the sequence (by comparison with the closest genes and alleles *Homo sapiens* IGKV1D-33*01 and IGKJ1*01)**

```
>M64855|IGKV1D-33*01|Homo sapiens|F|V-REGION|321..607|287 nt|1| | | |95 AA|95+0=287| | |
DIQMTQSPSSLSASVGDRVTITCQASQDISNYLNWYQQKPGKAPKLLIYDASNLETGVPSRFSGSGSGTDFTFTISSLQPEDIATYYCQQYDNLP


>M64855|IGKV1D-33*01|Homo sapiens|F|V-REGION|321..607|287 nt|1| | | | |287+0=287| | |
GACatcCAGatgACCcagTCTccaTCCtccCTGtctGCAtctGTAggaGACagaGTCaccATCactTGCcagGCGagtCAGgacATTagcAACtatTTAaatTGGtatCAGcagAAAccaGGGaaaGCCcctA
AGctcCTGatcTACgatGCAtccAATttgGAAacaGGGgtcCCAtcaAGGttcAGTggaAGTggaTCTgggACAgatTTTactTTCaccATCagcAGCctgCAGcctGAAgatATTgcaACAtatTACtgtCA
AcagTATgatAATctcCCT

>J00242|IGKJ1*01|Homo sapiens|F|J-REGION|251..288|38 nt|2| | | |12 AA|12+0=38| | |
WTFGQGTKVEIK

>J00242|IGKJ1*01|Homo sapiens|F|J-REGION|251..288|38 nt|2| | | | |38+0=38| | |
Tggacgttcggccaagggaccaaggtggaaatcaaa

WTFGQGTKVEIK
```

Figure 18

Hybrid (closest humanized Avastin Kappa Chain) IGKV1D-33-01 Kappa Chain and CAN20G2 Kappa CDRs

Kozak and HAVT20 Leader
Framework 1-2-3
CAN20G2 Kappa CDR1-2-3
IGKJ1-01
Altered nucleotides (codons) bold and underlined and capitalized to match Avastin.

<-----------------------------Kozak and HAVT20 Leader-----------------------------
GCCGCCACCATGGCATGCCCTGGCTTCCTGTGGGCACTTGTGATCTCCACCT ----------------------------><----------------------------FR1----------------------------
GTCTTGAATTTTCCATGGCTGACATCCAGATGACCCAGTCTCCATCCTCCCTGTCT --------------------------------------------------------><-----------CDR1-----------
GCATCTGTAGGAGACAGAGTCACCATCACTTGCAGCGCGAGTTCAAGTGTAATTTC -----------><----------------------------FR2----------------------------
CACTTACTTAAATTGGTATCAGCAGAAACCAGGGAAAGCCCCTAAGGTGCTGATCTA -><------CDR2------><----------------------------FR3----------------------------
CAGCACATCCAGCTTGCACAGCGGGGTCCCATCAAGGTTCAGTGGAAGTGGATCTG ------------------------------------------------------------------------------
GGACAGATTTTACTCTGACCATCAGCAGCCTGCAGCCTGAAGATTTCGCAACATATT --------><--------------------CDR3--------------------><----------------FR4----------------
ACTGTCTCCAGTATCACCGTTCCCCACGGACGTTCGGCCAAGGGACCAAGGTGG ----------->
AAATCAAACGTAAGTGCACTTTGCGGCCGCTAGGAAGAAACTCAAAACATCAAGATTTTAA
ATACGCTTCTTGGTCTCCTTGCTATAATTATCTGGGATAAGCATGCTGTTTTCTGTCTGTCCCT
AACATGCCCTGTGATTATCCGCAAACAACACACCCAAGGGCAGAACTTTGTTACTTAAACAC
CATCCTGTTTGCTTCTTTCCTCAGGAACTGTGGCTGCACCATCTGTCTTCATCTTCCCGCC
ATCTGATGAGCAGTTGAAATCTGGAACTGCCTCTGTTGTGTGCCTGCTGAATAACTTCT
ATCCCAGAGAGGCCAAAGTACAGTGGAAGGTGGATAACGCCCTCCAATCGGGTAACTC
CCAGGAGAGTGTCACAGAGCAGGACAGCAAGGACAGCACCTACAGCCTCAGCAGCAC
CCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTGATAGT
TAACG

Figure 19a

Kozak and HAVT20 Leader
CAN20G2 Heavy V-Region
Human IgG1 Constant with Introns
Double Stop <----------Kozak and HAVT20 Leader----------
GCCGCCACCATGGCATGCCCTGGCTTCCTGTGGGCACTTGTGATCTCCACCT ----------><---------- CAN20G2 Heavy V-Region----------
GTCTTGAATTTTCCATGGCTCAGATCCAGTTGGTGCAGTCTGGACCTGAGGT

GAAGAAGCCTGGAGAGACAGTCAAGATCTCCTGCAAGGCTTCTGGGTATAC

CTTCACAAACCAAGGAATGAACTGGGTGAAACAGGCTCCAGGAAAGGGTTT

AAAGTGGATGGGCTGGATAAACACCAACACTGGAGAGCCAACATATACTGA

AGAGTTCAAGGGACGGTTTGCCTTCTCTTTAGAAACCTCTGCCAGCACTGCC

TATTTGCAGATCAACAACCTCAAAAATGAGGACACGGCTACATATTTCTGTT

ATGTTAACTACGATTATTATACTATGGACTTCTGGGGTCAAGGAACCTCGGT

----------><---------- Human IgG1 Constant with Introns----------
CACCGTCTCCTCAGGTGAGTGCGGCCGCGAGCCCAGACACTGGACGCTGAA

CCTCGCGGACAGTTAAGAACCCAGGGGCCTCTGCGCCCTGGGCCCAGCTCT

GTCCCACACCGCGGTCACATGGCACCACCTCTCTTGCAGCCTCCACCAAGG

GCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTG

ACGGTGTCGTGGAACTCAGGCGCCCTGACCAGCGGCGTGCACACCTTCC

Figure 19a Cont.

CGGCTGTCCTACAGTCCTCAGGACTCTACTCCCTCAGCAGCGTGGTGAC

CGTGCCCTCCAGCAGCTTGGGCACCCAGACCTACATCTGCAACGTGAAT

CACAAGCCCAGCAACACCAAGGTGGACAAGAGAGTTGGTGAGAGGCCAG

CACAGGGAGGGAGGGTGTCTGCTGGAAGCCAGGCTCAGCGCTCCTGCCTGG

ACGCATCCCGGCTATGCAGTCCCAGTCCAGGGCAGCAAGGCAGGCCCCGTC

TGCCTCTTCACCCGGAGGCCTCTGCCCGCCCCACTCATGCTCAGGGAGAGGG

TCTTCTGGCTTTTTCCCCAGGCTCTGGGCAGGCACGGGCTAGGTGCCCCTAA

CCCAGGCCCTGCACACAAAGGGGCAGGTGCTGGGCTCAGACCTGCCAAGAG

CCATATCCGGGAGGACCCTGCCCCTGACCTAAGCCCACCCCAAAGGCCAAA

CTCTCCACTCCCTCAGCTCGGACACCTTCTCTCCTCCCAGATTCCAGTAACT

CCCAATCTTCTCTCTGCAGAGCCCAAATCTTGTGACAAAACTCACACATG

CCCACCGTGCCCAGGTAAGCCAGCCCAGGCCTCGCCCTCCAGCTCAAGGC

GGGACAGGTGCCCTAGAGTAGCCTGCATCCAGGGACAGGCCCCAGCCGGGT

GCTGACACGTCCACCTCCATCTCTTCCTCAGCACCTGAACTCCTGGGGGGA

CCGTCAGTCTTCCTCTTCCCCCCAAAACCCAAGGACACCCTCATGATCT

CCCGGACCCCTGAGGTCACATGCGTGGTGGTGGACGTGAGCCACGAAG

ACCCTGAGGTCAAGTTCAACTGGTACGTGGACGGCGTGGAGGTGCATAA

Figure 19a Cont.

TGCCAAGACAAAGCCGCGGGAGGAGCAGTACAACAGCACGTACCGTGT

GGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAA

CCATCTCCAAAGCCAAAGGTGGGACCCGTGGGGTGCGAGGGCCACATGGA

CAGAGGCCGGCTCGGCCCACCCTCTGCCCTGAGAGTGACCGCTGTACCAAC

CTCTGTCCCTACAGGGCAGCCCCGAGAACCACAGGTGTACACCCTGCCCC

CATCCCGGGAGGAGATGACCAAGAACCAGGTCAGCCTGACCTGCCTGGT

CAAAGGCTTCTATCCCAGCGACATCGCCGTGGAGTGGGAGAGCAATGG

GCAGCCGGAGAACAACTACAAGACCACGCCTCCCGTGCTGGACTCCGAC

GGCTCCTTCTTCCTCTATAGCAAGCTCACCGTGGACAAGAGCAGGTGGC

AGCAGGGGAACGTCTTCTCATGCTCCGTGATGCATGAGGCTCTGCACAA

CCACTACACGCAGAAGAGCCTCTCCCTGTCTCCGGGTAAATGATGA

Translation Introns Removed:

<---------Kozak and HAVT20 Leader-------><----------------------------- CAN20G2 Heavy V-Region----------
AATMACPGFLWALVISTCLEFSMAQIQLVQSGPEVKKPGETVKISCKASGYTFTNQG

MNWVKQAPGKGLKWMGWINTNTGEPTYTEEFKGRFAFSLETSASTAYLQINNLKNE

><----------- Human IgG1 Constant with Introns----------
DTATYFCYVNYDYYTMDFWGQGTSVTVSSASTKGPSVFPLAPSSKSTSGGTAALGCL

VKDYFPEPVTVSWNSGALTSGVHTFPAVLQSSGLYSLSSVVTVPSSSLGTQTYICNVN

HKPSNTKVDKRVEPKSCDKTHTCPPCPAPELLGGPSVFLFPPKPKDTLMISRTPEVTCV

Figure 19a Cont.

VVDVSHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHEAL

HNHYTQKSLSLSPGK

Figure 19b

Kozak and HAVT20 Leader
CAN20G2 Kappa V-Region
Altered BamHI Site
Kappa Constant with Introns
Double Stop <-----------------Kozak and HAVT20 Leader-----------------
GCCGCCACCATGGCATGCCCTGGCTTCCTGTGGGCACTTGTGATCTCCACCTGTCTT ----------><-----------------CAN20G2 Kappa V-Region-----------------
GAATTTTCCATGGCTCAAGTTGTTCTCACCCAGTCTCCAGCAATCATGTCTGCATCT

CTAGGGGATCGGGTCACCATGACCTGCACTGCCAGCTCAAGTGTAATTTCCACTTA

CTTGCACTGGTATCAGCAGAAGCCAGGCTCTTCCCCCAAACTCTGGATTTATAGCA

CATCCACCCTGGCTTCTGGAGTCCCACCTCGCTTCAGTGGCAGTGGGTCTGGGACC

TCTTACTCTCTCACAATCAGCAGCATGGAGGCTGAAGATGCTGCCACTTATTACTG

CCTCCAGTATCACCGTTCCCCACGGACGTTCGGTGGAGGCACCAAGCTGGAAATCA

---><-----------------Kappa Constant with Introns-----------------
AACGTAAGTGCACTTTGCGGCCGCTAGGAAGAAACTCAAAACATCAAGATTTTAAATACGCT

TCTTGGTCTCCTTGCTATAATTATCTGGGATAAGCATGCTGTTTTCTGTCTGTCCCTAACAT

GCCCTGTGATTATCCGCAAACAACACACCCAAGGGCAGAACTTTGTTACTTAAACACCATCC

TGTTTGCTTCTTTCCTCAGGAACTGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCCCAGGAGAGTGTC

ACAGAGCAGGACAGCAAGGACAGCACCTACAGCCTCAGCAGCACCCTGACGCTGAGCAAAGC

AGACTACGAGAAACACAAAGTCTACGCCTGCGAAGTCACCCATCAGGGCCTGAGCTCGCCCG

Figure 19b Cont.

```
------------------------------------------------------------------>
TCACAAAGAGCTTCAACAGGGGAGAGTGTTGATAG

Translation Introns Removed:

<--------Kozak and HAVT20 Leader--------><-------------------------------------CAN20G2 Kappa V-Region--------------
AATMACPGFLWALVISTCLEFSMAQVVLTQSPAIMSASLGDRVTMTCTASSSVISTYLHWYQ

------------------------------------------------------------------------------------------------------------------
QKPGSSPKLWIYSTSTLASGVPPRFSGSGSGTSYSLTISSMEAEDAATYYCLQYHRSPRTFG

----------------><----------------------------------Kappa Constant with Introns-----------------------------------
GGTKLEIKRTVAAPSVFIFPPSDEQLKSGTASVVCLLNNFYPREAKVQWKVDNALQSGNSQE

------------------------------------------------------------------------------------------------->
SVTEQDSKDSTYSLSSTLTLSKADYEKHKVYACEVTHQGLSSPVTKSFNRGEC
```

Neutralization of CNJ Toxin A (250 ng/ml) with Humanized Can 20 Mabs

- cCan20G2
- HE-Can20G2
- hCDR
- AVA
- CDAIgG

X-axis: Concentration (ug/ml): 20.00, 10.00, 5.00, 2.50, 1.25, 0.63, 0.31, 0.16
Y-axis: Percent Neutralization (0.0–70.0)

CLOSTRIDIUM DIFFICILE ANTIBODIES

CROSS REFERENCE TO RELATED APPLICATIONS

This application is a Division of U.S. application Ser. No. 13/592,286, filed Aug. 22, 2012, which claims priority to U.S. Provisional Application No. 61/526,031 filed Aug. 22, 2011, the disclosures of which are incorporated herein by reference in their entireties.

INCORPORATION OF SEQUENCE LISTING

The sequence listing that is contained in the file named "57964_159885_Seq List.txt", which is 101,876 bytes (measured in operating system MS-Windows), created on Oct. 11, 2016, is filed herewith by electronic submission and incorporated herein by reference in its entirety. The sequence listing contains SEQ ID NOs: 1-104.

FIELD

The invention relates to monoclonal antibodies to *Clostridium difficile* toxin A. The invention further relates to compositions and methods for the treatment or prevention of infection by the bacteria, *Clostridium difficile*, in a vertebrate subject. Methods are provided for administering antibodies to the vertebrate subject in an amount effective to reduce, eliminate, or prevent relapse from infection. Methods for the treatment or prevention of *Clostridium difficile* infection in an organism are provided.

BACKGROUND

*Clostridium difficile* (*C. difficile*) is a common nosocomial pathogen and a major cause of morbidity and mortality among hospitalized patients throughout the world. Kelly et al., New Eng. J. Med., 330:257-62, 1994. The increased use of broad spectrum antibiotics and the emergence of unusually virulent strains of *C. difficile* have lead to the idea that vaccines may be well suited to reduce disease and death associated with this bacterium. *C. difficile* has few traditional antibiotic options and frequently causes a recurring disease (25% of cases). *C. difficile* claims about 20,000 lives in the USA alone per year and causes around 500,000 confirmed infections. Recently, more virulent strains of *C. difficile* have emerged that produce more toxin such as the B1/NAB1/027 strain, which also has a decreased susceptibility to metronidazole. Outbreaks of *C. difficile* have necessitated ward and partial hospital closure. With the increasing elderly population and the changing demographics of the population, *C. difficile* is set to become a major problem in the 21$^{st}$ century. The spectrum of *C. difficile* disease ranges from asymptomatic carriage to mild diarrhea to fulminant pseudomembranous colitis.

*C. difficile* has a dimorphic lifecycle whereby it exists both as an infectious and tough spore form and a metabolically active toxin-producing vegetative cell. *C. difficile*-associated disease (CDAD) is believed to be caused by the vegetative cells and more specifically the actions of two toxins, enterotoxin toxin A and cytotoxin toxin B. Vaccines and therapy for *C. difficile* have been to date focused upon the toxins (A and B), toxoids of A and B, recombinant fragments of A and B, and vegetative cell surface layer proteins (SLPAs).

Toxin A is a high-molecular weight protein that possesses multiple functional domains. The toxin is broken up into 4 functional domains: an amino-terminal glucosyltransferase that modifies Rho-like GTPases leading to cytoskeletal dysregulation in epithelial cells, an autocatalytic cysteine protease domain, a hydrophobic membrane-spanning sequence, and a highly repetitive carboxy-terminal host-cell binding domain. The carboxy terminal domain anchors the toxin to the host cell carbohydrate receptors on intestinal epithelial cells which initiates the internalization process thereby delivering the amino-terminal enzymatic domains to the cytoplasm of the target cells. The delivery of the enzymatic domain and glucosyltransferase activity leads to diarrhea and inflammation due to the apoptotic cell death of the intoxicated cells.

Many studies have shown the importance of antibodies against the toxins in affecting the disease outcome. Studies have also shown the correlation between serum anti-toxinA antibodies with protection from CDAD and relapse. These studies have led to the creation of toxin mAb therapies for CDAD.

Despite these advances, there is an unmet need for effective treatment and/or prevention of *C. difficile* associated infections including prevention from relapse of CDAD. The present invention provides mouse and humanized antibodies to toxin A to satisfy these and other needs.

SUMMARY

The present invention provides for antibodies, or antigen-binding portions thereof, that bind to *Clostridium difficile* (*C. difficile*) toxin A. The antibody or antigen-binding portion thereof may bind to fragment 4 of *C. difficile* toxin A.

In one embodiment, the present invention provides for an isolated monoclonal antibody, or an antigen-binding portion thereof, comprising a heavy chain region and a light chain region, wherein the heavy chain region comprises three complementarity determining regions (CDRs), CDR1, CDR2 and CDR3, having amino acid sequences about 80% to about 100% homologous to the amino acid sequences set forth in SEQ ID NOs: 29, 30 and 31, respectively, and wherein the light chain region comprises three CDRs, CDR1, CDR2 and CDR3, having amino acid sequences about 80% to about 100% homologous to the amino acid sequences set forth in SEQ ID NOs: 21, 22 and 23, respectively.

Also provided is an isolated monoclonal antibody, or an antigen-binding portion thereof, that binds to *C. difficile* toxin A and comprises a heavy chain region, wherein the heavy chain region comprises three CDRs, CDR1, CDR2 and CDR3, having amino acid sequences about 80% to about 100% homologous to the amino acid sequences set forth in SEQ ID NOs: 29, 30 and 31, respectively.

The present invention further provides for an isolated monoclonal antibody, or an antigen-binding portion thereof, that binds to *C. difficile* toxin A and comprises a light chain region, wherein the light chain region comprises three CDRs, CDR1, CDR2 and CDR3, having amino acid sequences about 80% to about 100% homologous to the amino acid sequences set forth in SEQ ID NOs: 21, 22 and 23, respectively.

The antibody or antigen-binding portion thereof may have a dissociation constant ($K_D$) of less than about $1\times10^{-11}$ M. The antibody or antigen-binding portion thereof may be humanized or chimeric.

In one embodiment, the heavy chain region of the antibody or antigen-binding portion thereof comprises an amino acid sequence about 80% to about 100% homologous to the amino acid sequence set forth in SEQ ID NO: 89; the light chain region of the antibody or antigen-binding portion thereof comprises an amino acid sequence about 80% to about 100% homologous to the amino acid sequence set forth in SEQ ID NO: 91.

In another embodiment, the heavy chain region of the antibody or antigen-binding portion thereof comprises an amino acid sequence about 80% to about 100% homologous to the amino acid sequence set forth in SEQ ID NO: 93; the light chain region of the antibody or antigen-binding portion thereof comprises an amino acid sequence about 80% to about 100% homologous to the amino acid sequence set forth in SEQ ID NO: 95.

The antibody or antigen-binding portion thereof may be the following: (a) a whole immunoglobulin molecule; (b) an scFv; (c) a Fab fragment; (d) an F(ab')2; and (e) a disulfide linked Fv.

The antibody or antigen-binding portion thereof may comprise at least one constant domain selected from the group consisting of: a) an IgG constant domain; and (b) an IgA constant domain.

One embodiment of the present invention provides for an isolated monoclonal antibody or an antigen-binding portion thereof, that binds to *C. difficile* toxin A and comprises a heavy chain variable region, wherein the heavy chain variable region comprises an amino acid sequence about 80% to about 100% homologous to the amino acid sequence set forth in SEQ ID NOs: 12, 28, 44 or 60.

Another embodiment of the present invention provides for an isolated monoclonal antibody, or an antigen-binding portion thereof, that binds to *C. difficile* toxin A and comprises a light chain variable region, wherein the light chain variable region comprises an amino acid sequence about 80% to about 100% homologous to the amino acid sequence set forth in SEQ ID NOs: 4, 20, 36 or 52.

Yet another embodiment of the present invention provides for an isolated monoclonal antibody, or an antigen-binding portion thereof, wherein the antibody, or antigen-binding portion thereof, binds to the same epitope of *C. difficile* toxin A recognized by an antibody comprising a heavy chain variable region and a light chain variable region having amino acid sequences about 80% to about 100% homologous to the amino acid sequences set forth in SEQ ID NOs: 28 and 20, respectively.

Also encompassed by the present invention are an antibody produced by hybridoma designated CAN20G2 and the hybridoma designated CAN20G2.

The present invention provides for an isolated monoclonal antibody, or an antigen-binding portion thereof, wherein, in an in vivo toxin A challenge experiment, when the antibody, or an antigen-binding portion thereof, is administered to a mammal at a dosage ranging from about 8 mg/kg body weight to about 13 mg/kg body weight about 24 hours before the mammal is exposed to greater than about 100 ng of *C. difficile* toxin A, the chance of survival for the mammal is greater than about 80% within about 7 days.

Also encompassed by the present invention is an isolated monoclonal antibody, or an antigen-binding portion thereof, wherein the antibody, or antigen-binding portion thereof, at a concentration ranging from about 4 μM to about 17 μM, neutralizes greater than about 40% of about 150 ng/ml *C. difficile* toxin A in an in vitro neutralization assay.

The present invention provides for an isolated nucleic acid encoding a peptide comprising an amino acid sequence about 80% to about 100% homologous to the amino acid sequence set forth in SEQ ID NOs: 12, 28, 44, 60, 4, 20, 36 or 52. The present invention also provides for an isolated nucleic acid comprising a nucleic acid sequence about 80% to about 100% homologous to the nucleic acid sequence set forth in SEQ ID NOs: 68, 69, 70, 71, 72, 73, 74 or 75. Also provided is a cell comprising any of these nucleic acids. The cell can be a bacterial cell or a eukaryotic cell, such as a mammalian cell. Non-limiting examples of the cells include COS-1, COS-7, HEK293, BHK21, CHO, BSC-1, Hep G2, SP2/0, HeLa, myeloma or lymphoma cells.

The present invention provides for a composition comprising the antibody or antigen-binding portion thereof and at least one pharmaceutically acceptable carrier.

The present invention provides for a method of preventing or treating *C. difficile*-associated disease comprising administering to a subject an effective amount of the present antibody or antigen-binding portion thereof. The antibody or antigen-binding portion thereof may be administered intravenously, subcutaneously, intramuscularly or transdermally. The method may contain another step of administering to the subject a second agent. For example, the second agent may be a different antibody or fragment thereof, or may be an antibiotic such as vancomycin, metronidazole or fidaxomicin.

BRIEF DESCRIPTION OF THE DRAWINGS

FIG. 1 shows a standardized ELISA showing the reactivity of purified murine mAbs on *Clostridium difficile* toxin A.

FIG. 4 shows a Western immunoblot of Purified Murine CAN19 mAbs (0.5 μg/ml). Lane 1: Toxin A; Lane 2: Toxoid A; Lane 4: Toxin A Fragment 4; Lane 5: Toxin B; Lane 7: Toxin B Fragment 4; Lane 8: PilF (negative control). Expected sizes: Toxin A (308 kDa); Toxin A Fragment 4 (114 kDa); Toxin B (280 kDa).

FIG. **6*a*** is an epitope binning graph showing biotinylated CAN20G1 antibody binding to SA (streptavidin) biosensor. The bound antibody is then incubated with free Toxin A and free CAN20G1. The CAN20G1-Toxin A complex is again incubated with free antibody. A large nm shift in wavelength will indicate binding of the analyte indicating that CAN20G1 and the free antibody have different epitopes. 1, Biotinylated CAN20G1 to SA biosensors. 2, Free whole toxin A forming complex with CAN20G1. 3, Free CAN20G1 associating with biotinylated CAN20G1-Toxin A complex. 4, Association sample curves. 5, Dissociation step.

FIG. **6*b*** is a graph showing the final three steps (3-5) of the full program. A large nm shift in wavelength will indicate binding of the analyte indicating that CAN20G1 and the free antibody have different epitopes. In this case, only CDA1 (Merck anti-toxin A mAb used as a control) had a significant nm shift in wavelength demonstrating that CDA1 binds to a different epitope while CAN20G1, G2, G5, and G8 bind to the same epitope bin as CAN20G1.

Figure 7:
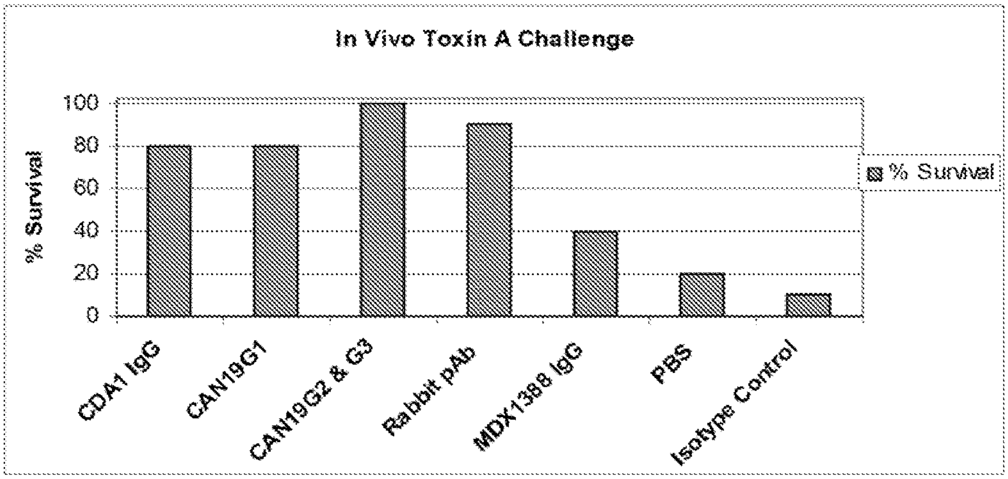

FIG. 7 is a bar graph showing the effects of *C. difficile* toxin A on mouse survival and the efficacy of the CAN19 mAbs against the toxin A challenge.

Figure 8:
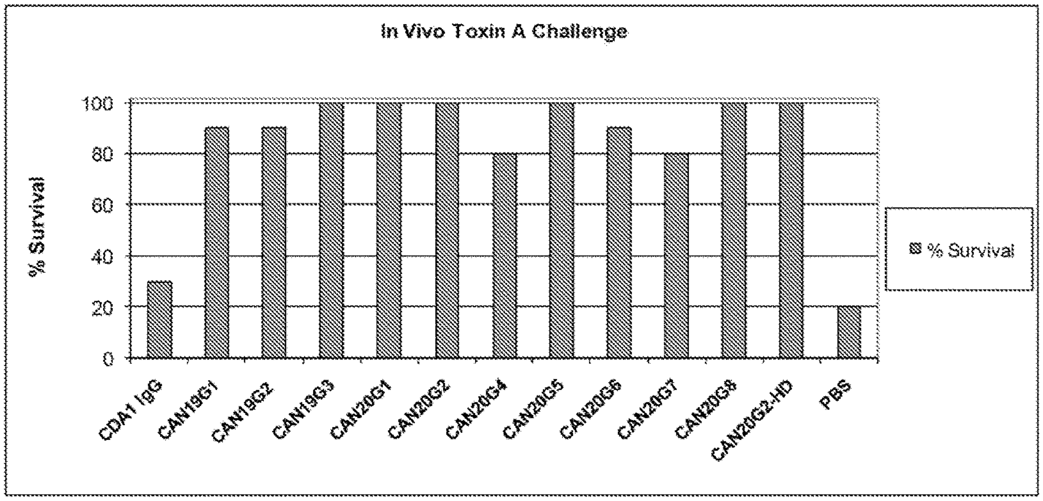

FIG. 8 is a bar graph showing the effects of *C. difficile* toxin A on mouse survival and the efficacy of the CAN19 and CAN20 mAbs against toxin A challenge.

Figure 9:
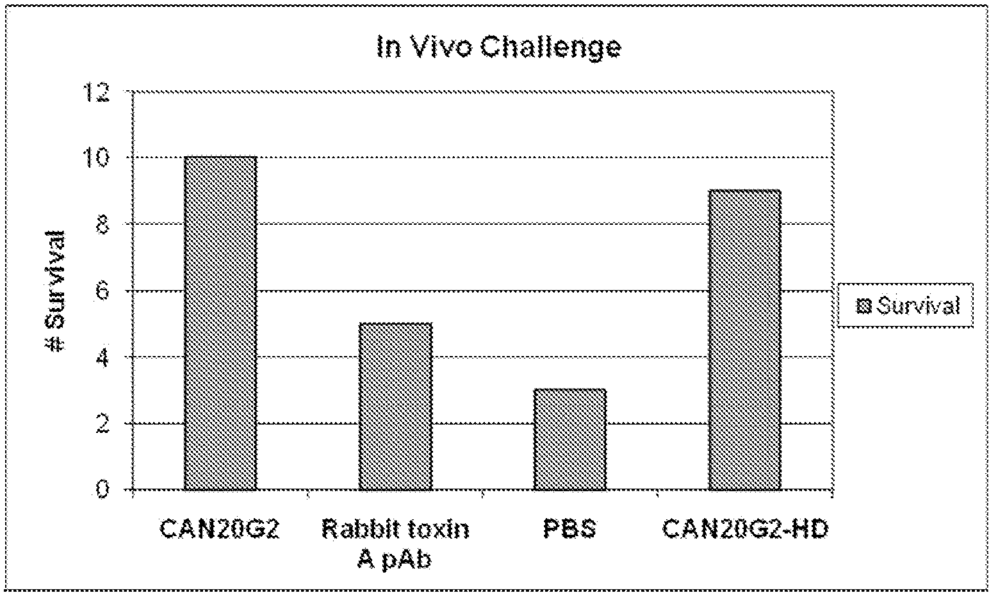

FIG. 9 is a bar graph showing the effects of *C. difficile* toxin A on mouse survival and the efficacy of the murine CAN20G2 mAb at full dose and half dose against toxin A challenge.

FIG. 10 shows primers used for V gene amplification from RNA. The degenerate base symbols are IUPAC (International union of pure and applied chemistry) codes for representing degenerate nucleotide sequence patterns.

FIG. 11 shows V-gene sequencing results for muCAN20G2 that includes both VH and VL sequences from the muCAN20G2 parental clones.

FIG. 12 shows alignment of muCAN20G2 v-regions with the closest human germline v-region. The human germlines were used as acceptor frameworks for humanization.

FIGS. 13*a* and 13*b* show CDR-huCAN20G2 design. The closest matching human frameworks are IGHV7-4-1*02 and IGKV1-39*01. The CDRs (IMGT Numbering) of the muCAN20G2 were inserted into the human framework. FIG. 13A shows the heavy chain variable region, including both nucleic acid sequence and amino acid sequence. FR1, FR2 and FR3 are from IGHV7-4-1*02; FR4 is from IGHJ6*01. FIG. 13B shows the light (kappa) chain variable region, including both nucleic acid sequence and amino acid sequence. FR1, FR2 and FR3 are from IGKV1-39*01; FR4 is from IGKJ4*01.

FIGS. 14*a* and 14*b* show HE-huCAN20G2 Design. Resurfaced and altered codons are in bold. The nucleotide sequence was translated to ensure correct frame. FIG. 14A shows the heavy chain variable region, including both nucleic acid sequence and amino acid sequence. FIG. 14B shows the light (kappa) chain variable region, including both nucleic acid sequence and amino acid sequence.

FIG. 15 shows the HE-huCAN20G2 Heavy Chain. Resurfaced and altered codons are in bold. After v-region design, an IgG1 constant region was added. The introns were removed and the nucleotide sequence was translated to ensure correct frame.

FIG. 16 shows HE-huCAN20G2 Kappa Chain. Resurfaced and altered codons are in bold. After v-region design, a Kappa constant region was added. The introns were removed and the nucleotide sequence was translated to ensure correct frame.

FIG. 17 shows AVA-huCAN20G2 kappa V-region alignment. The Avastin kappa v-region was aligned to the IMGT domain directory and identified the closest germline v-region. IGKV1D-33-01 was used as the acceptor framework for the AVA mAb design.

FIG. 18 shows AVA-huCAN20G2. The Avastin kappa v-region was aligned to the IMGT domain directory and identified the closest germline v-region. After analysis and design, a kappa constant region was added. As previously, the constant regions contain introns. For the AVA-huCAN20G2 heavy chain, the previously designed and resurfaced HE-huCAN20G2 heavy chain was used. FR1, FR2 and FR3 are from IGKV1D-33-01; FR4 is from IGKJ1-01.

FIGS. 19*a* and 19*b* show chimeric CAN20G2. Murine V-regions were designed with human constant regions. The introns were removed and the nucleotide sequence was translated to ensure correct frame. FIG. 19A shows the heavy chain, including both nucleic acid sequence and amino acid sequence. FIG. 14B shows the light (kappa) chain, including both nucleic acid sequence and amino acid sequence.

Figure 20A:
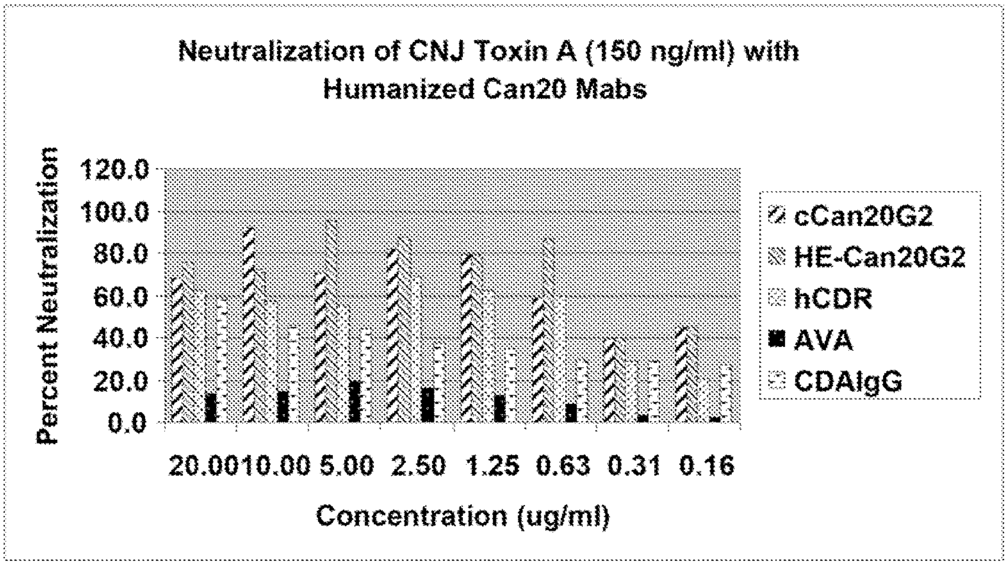

FIG. 20*a* shows neutralization data for purified human CAN20G2 clones at 150 ng/ml depicted as a bar graph.

Figure 20B:
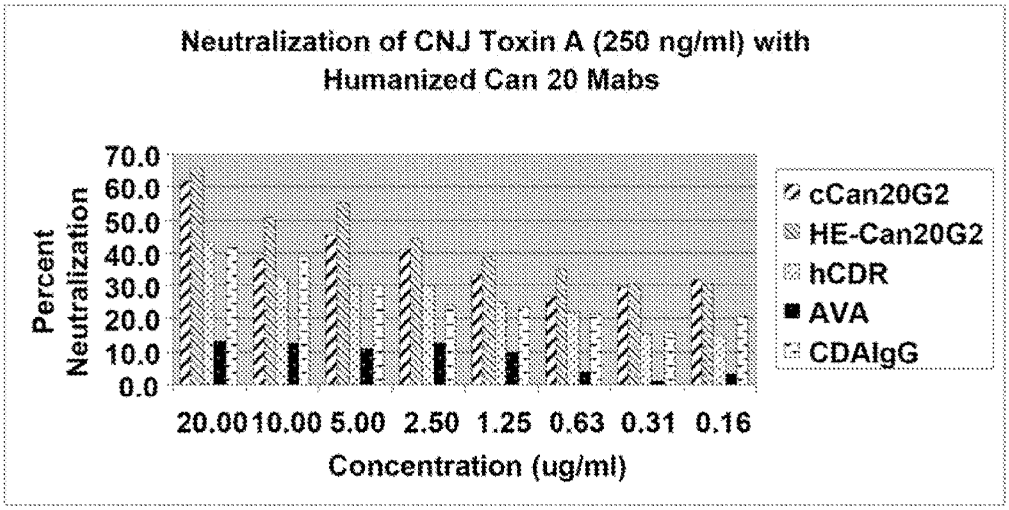

FIG. 20*b* shows neutralization data for purified human CAN20G2 clones at 250 ng/ml depicted as a bar graph.

Figure 21A:
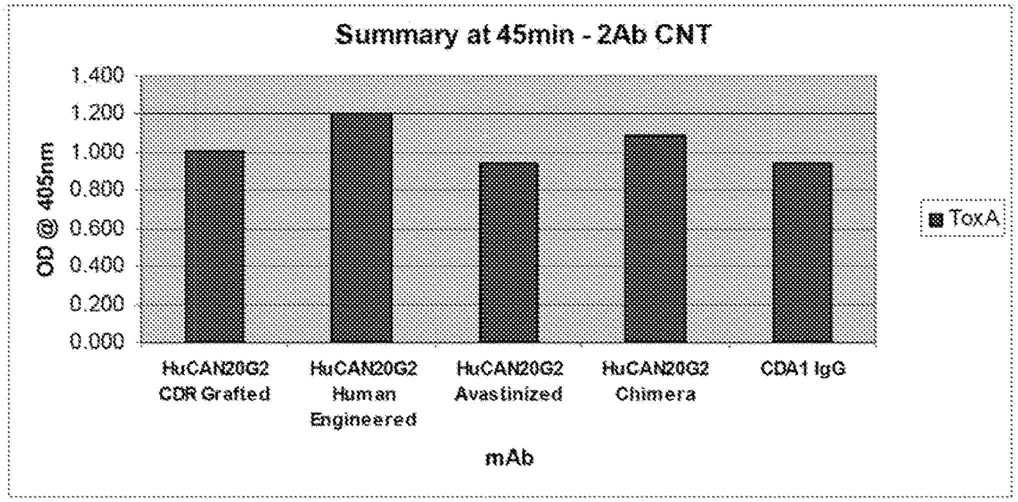

FIG. 21*a* shows ELISA to screen transfection supernatant for expressed human Can20G2 mAbs binding to toxin A at 45 minutes.

Figure 21B:
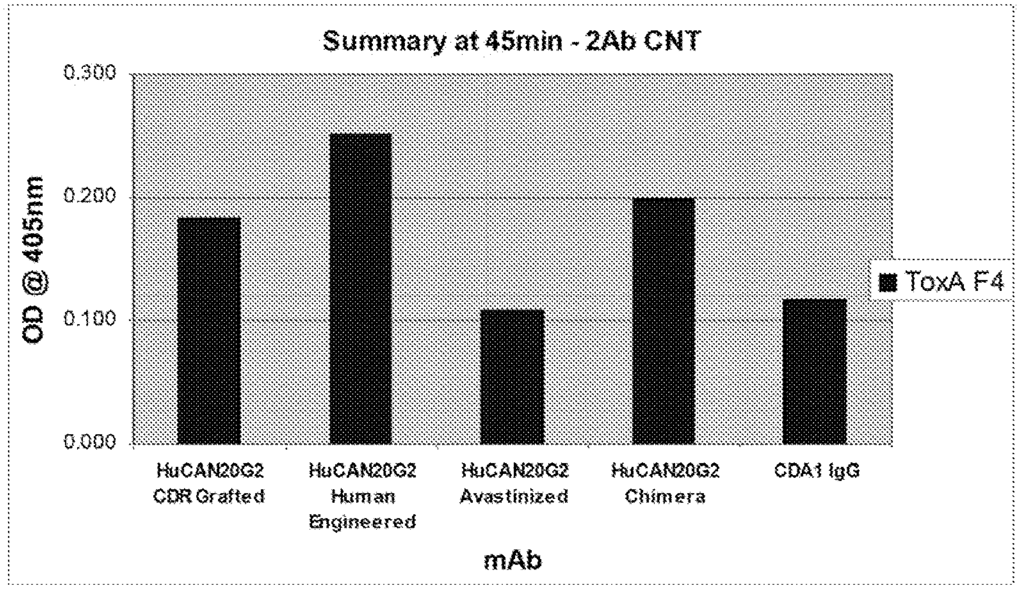

FIG. 21*b* shows ELISA to screen transfection supernatant for expressed human Can20G2 mAbs binding to toxin A fragment 4 at 45 minutes.

Figure 21C:
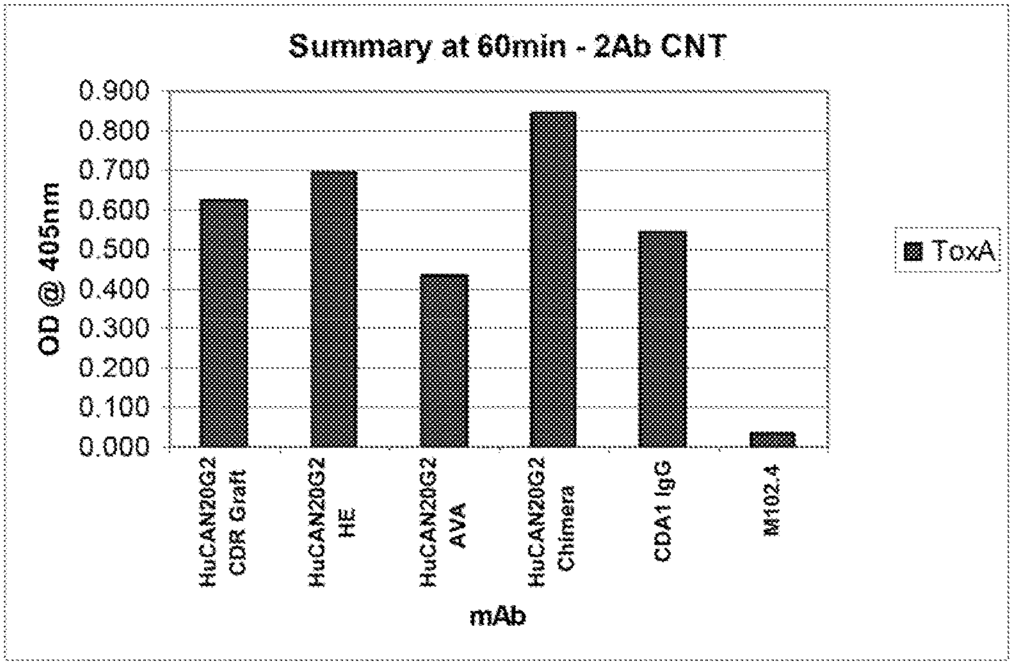

FIG. 21*c* shows ELISA to screen transfection supernatant for expressed human Can20G2 mAbs binding to toxin A at 60 minutes.

Figure 21D:
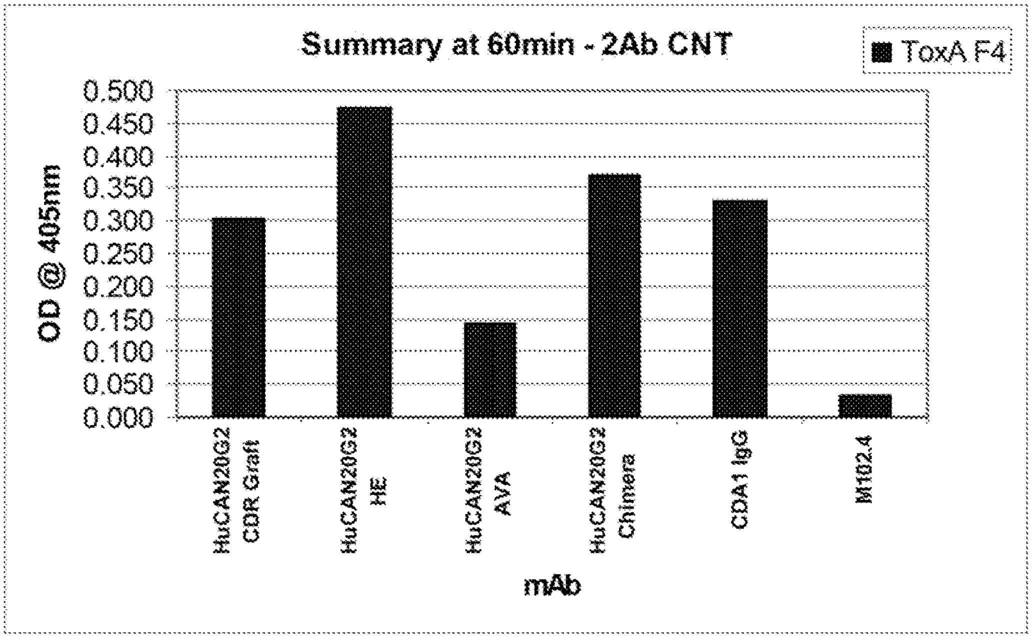

FIG. 21*d* shows an ELISA to screen transfection supernatant for expressed human Can20G2 mAbs binding to toxin A fragment 4 at 60 minutes.

Figure 22:
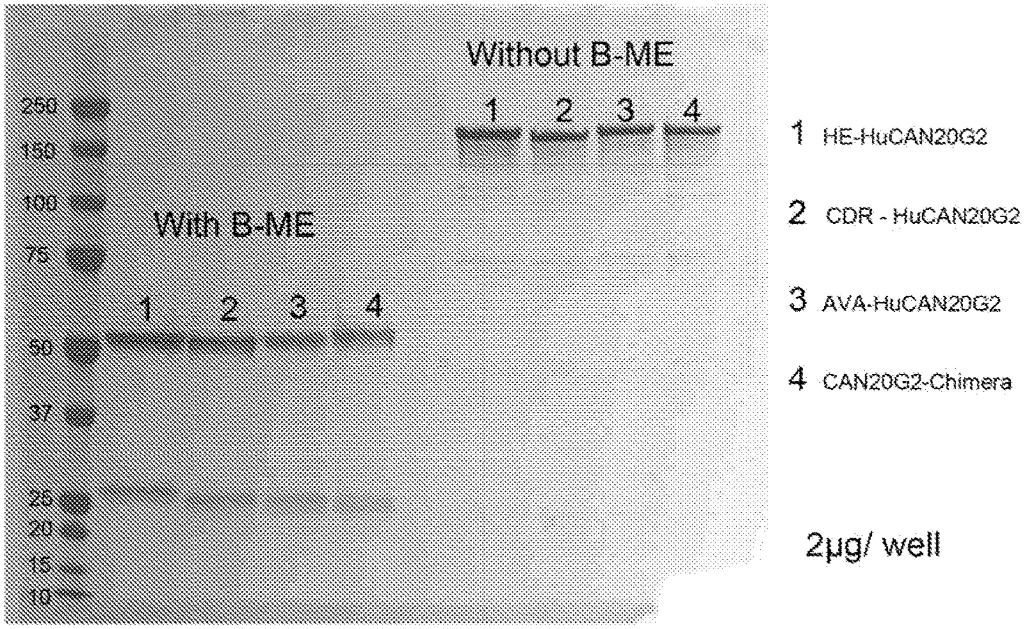

FIG. 22 shows SDS-PAGE of purified human CAN20G2 clones.

Figure 23:
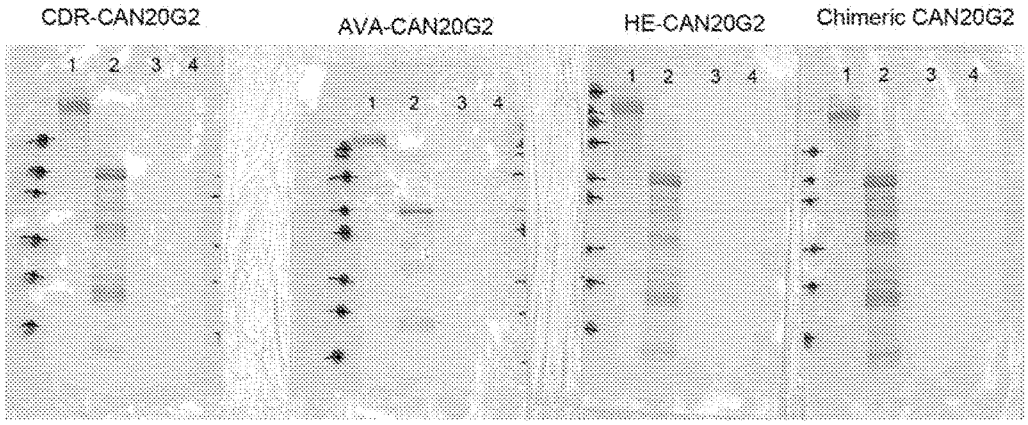

FIG. 23 shows Western blot analysis of purified human CAN20G2 clones. An SDS-page gel was run with tetanus toxoid, whole toxin A, toxin A fragment 4 and BSA. The gel was transferred to nitrocellulose membrane and probed with each of the human CAN20G2 mAbs (1 μg/ml). (Lane 1: Toxin A; Lane 2: Toxin A Fragment 4; Lane 3: tetanus toxoid; Lane 4: BSA).

Figure 24A:
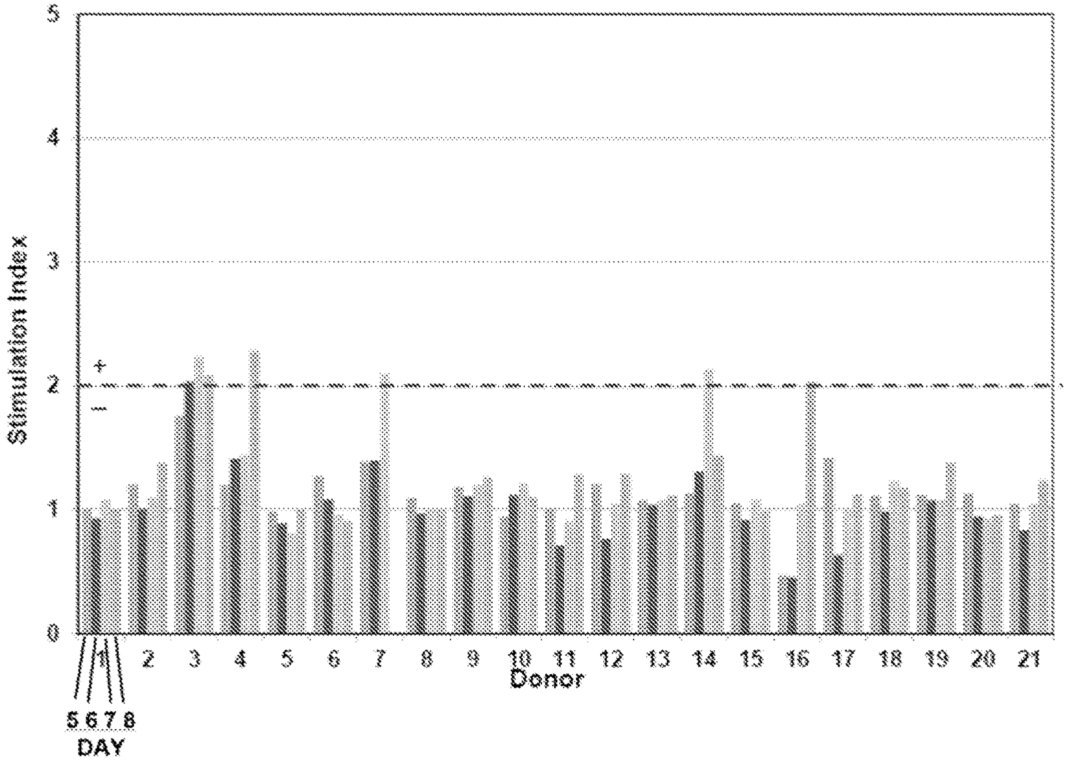
Figure 24B:
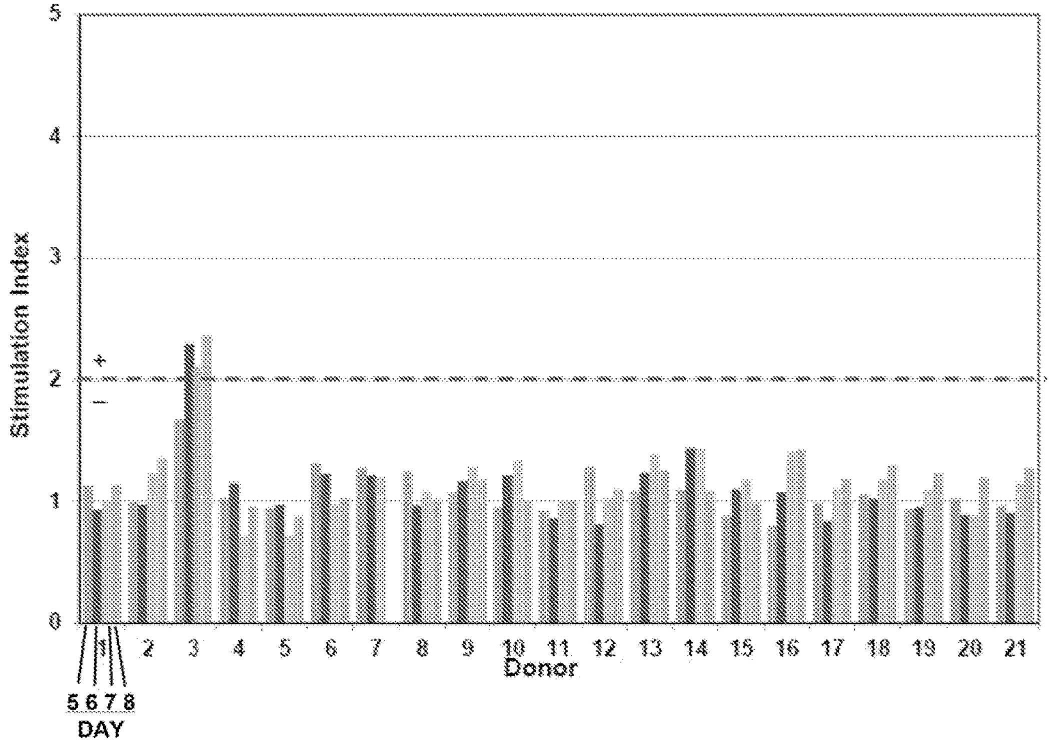

FIGS. 24*a* and 24*b* show healthy donor T cell proliferation responses to test antibodies, CDR-huCAN20G2 (FIG. 24A) and HE-huCAN20G2 (FIG. 24B), on days 5, 6, 7, and 8 after incubation. Proliferation responses with an SI≥2.00 (indicated by dotted line) that were significant ($p<0.05$) using an unpaired, two sample student's t test were considered positive. For each donor, the bars from left to right represent day 5, day 6, day 7 and day 8, respectively.

Figure 25:
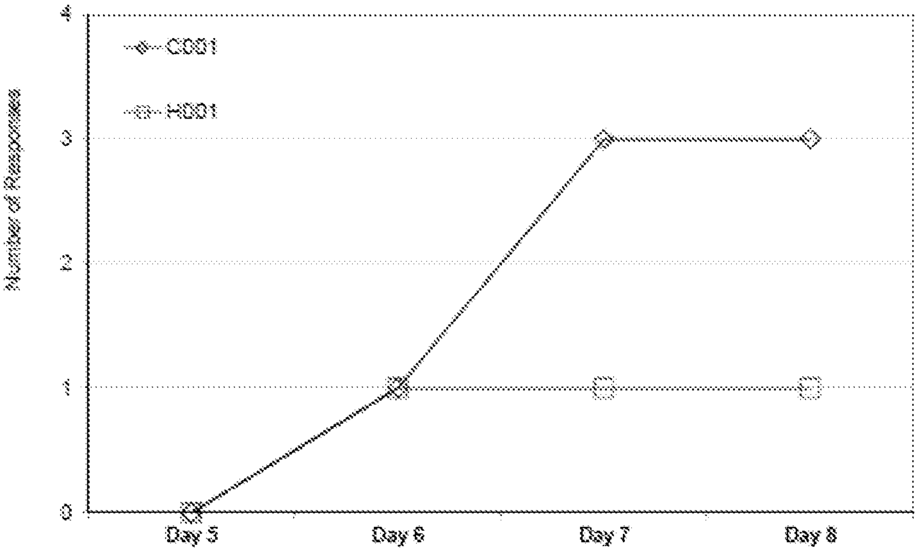

FIG. 25 shows the number of positive T cell proliferation responses to antibodies CDR-huCAN20G2 (C001) and HE-huCAN20G2 (H001) detected at four time points.

Figure 26:
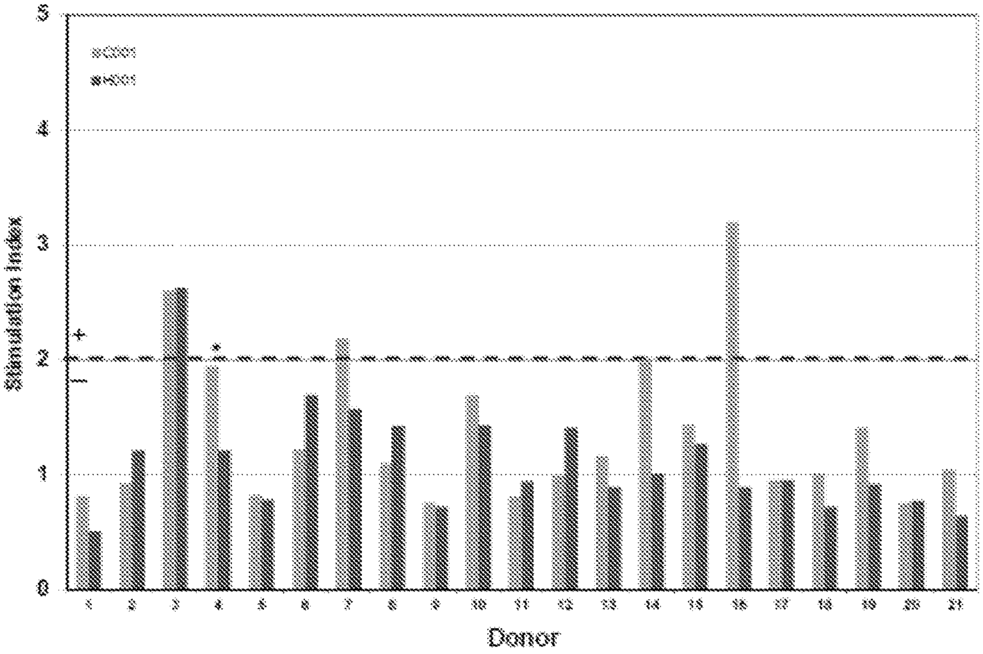

FIG. 26 shows healthy donor T cell IL-2 ELISpot responses to test antibodies, CDR-huCAN20G2 (C001) and HE-huCAN20G2 (H001). PBMCs were used to assess IL-2 secretion in response to stimulation with the two antibodies during an 8-day incubation. T cell responses with an SI≥2.00 that were significant ($p<0.05$) using an unpaired, two sample student's t test were scored positive. Borderline responses (significant $p<0.05$ with SI≥1.90) was shown (*).

Figure 27:
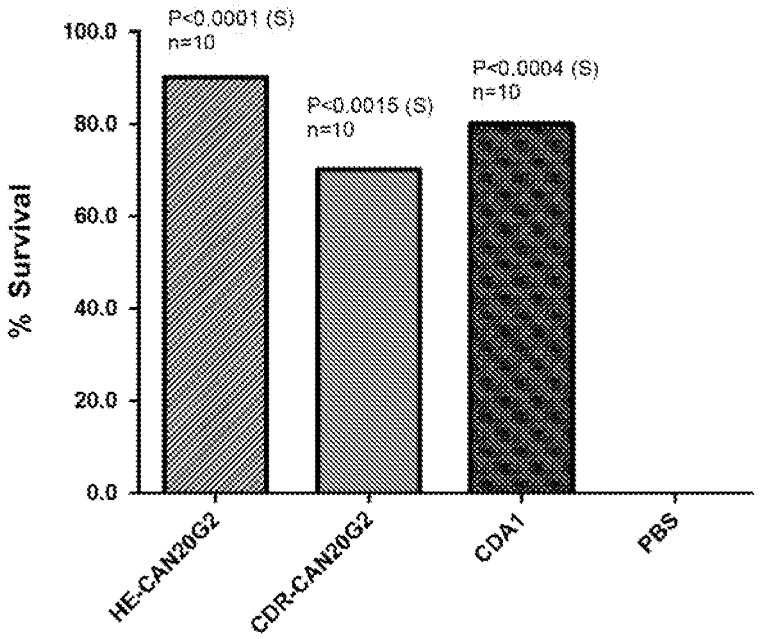

FIG. 27 shows the comparison of HE-huCAN20G2 ("HE-CAN20G2"), CDR-huCAN20G2 ("CDR-CAN20G2") and CDA1 (Merck/Medarex) anti-*C. difficile* toxin A (anti-TcdA) mAbs tested at a low dose of 0.05 mg/mouse. Efficacy of mAbs is presented as the percentages of survival compared to control animals (TcdA/PBS). *Fisher exact test for statistical significance.

Figure 28:
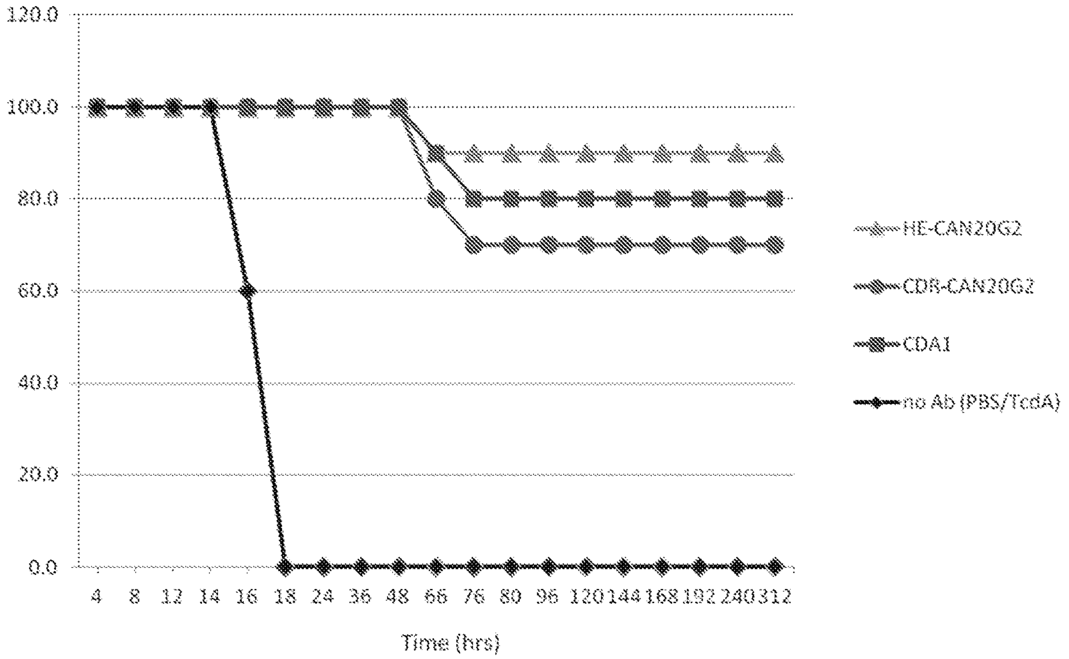

FIG. 28 shows the effect of humanized CAN20G2 mAbs, HE-huCAN20G2, CDR-huCAN20G2 in comparison with CDA1 on survival over time following TcdA challenge. The effect of mAbs at low dose of Ab (0.05 mg) or PBS alone (control) on survival related to time after TcdA challenge is depicted. The percent survival of animals in each group post TcdA challenge at the indicated time points (hrs) is shown in the graph.

Figure 29A:
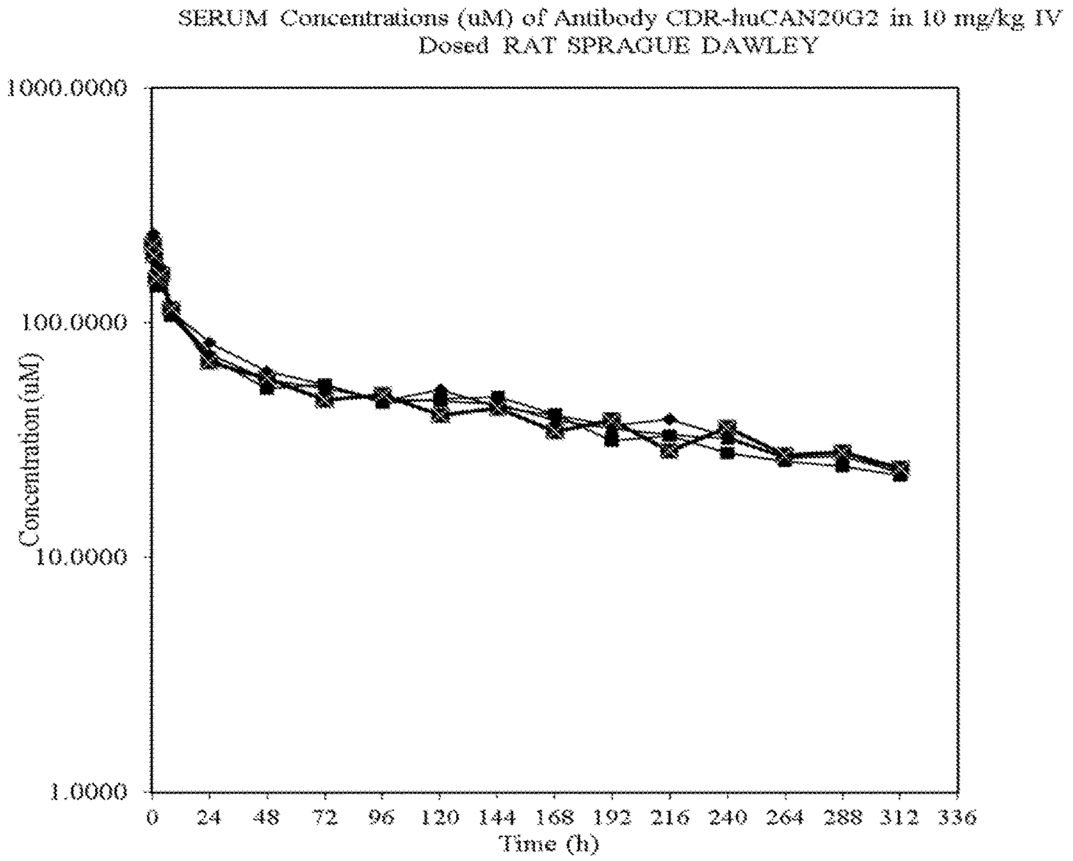
Figure 29B:
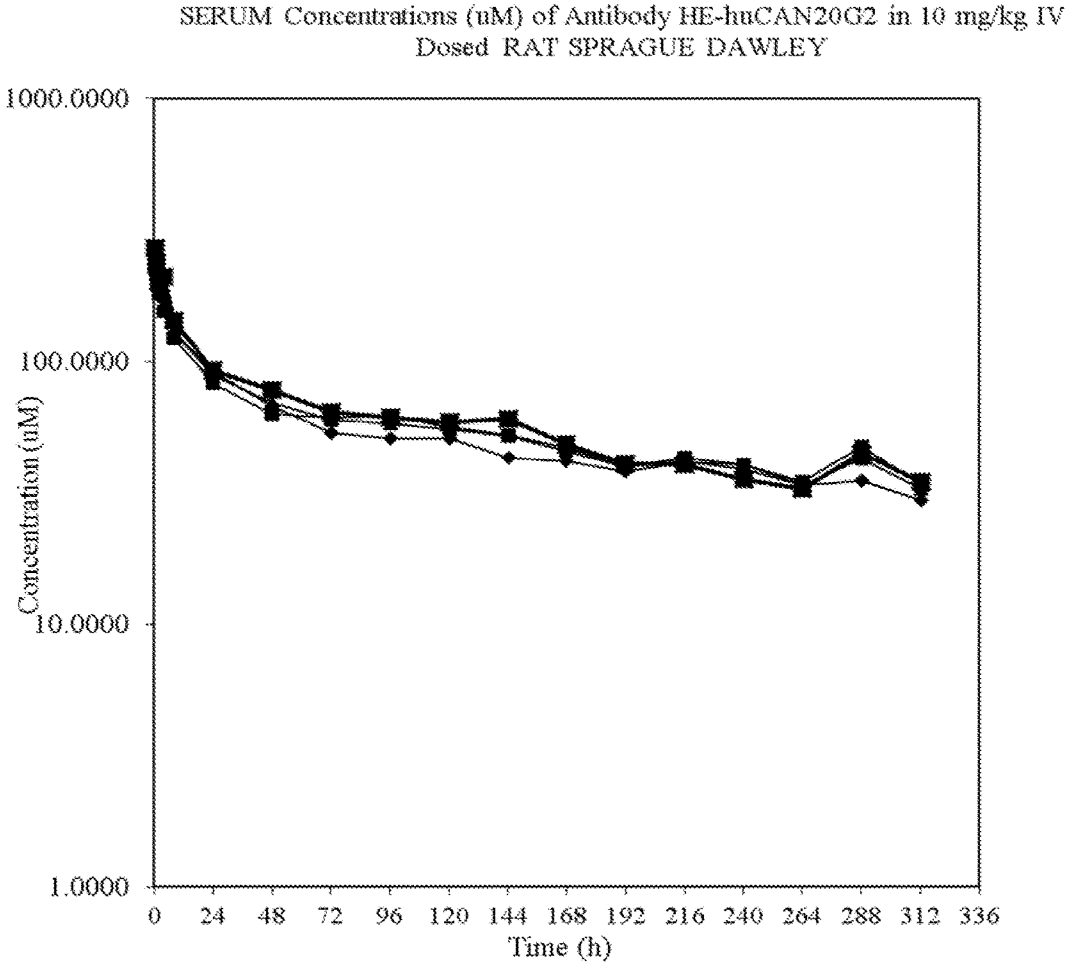

FIGS. 29*a* and 29*b* show PK study data of humanized antibodies CDR-huCAN20G2 (FIG. 29*a*) and HE-huCAN20G2 (FIG. 29*b*) in rats.

DETAILED DESCRIPTION

The present invention provides for compositions and methods for the prevention or treatment of *Clostridium*

*difficile* bacterial infection or bacterial carriage. The compositions contain antibodies (or an antigen-binding portion thereof) that recognize toxin A of *C. difficile*, including mouse monoclonal antibodies, humanized antibodies, chimeric antibodies, or antigen-binding portions of any of the foregoing. These antibodies (or antigen-binding portion thereof) can neutralize toxin A in vitro and in vivo, and/or inhibit binding of toxin A to mammalian cells. Therefore, the present antibodies or antigen-binding portion thereof can be used in passive immunization to prevent or treat *C. difficile*-associated disease (CDAD).

In one embodiment, the present antibodies or antigen-binding portions thereof provide one or more of the following effects: protect from or treat *C. difficile*-mediated colitis, antibiotic-associated colitis, pseudomembranous colitis (PMC) or other intestinal disease in a subject; protect from or treat diarrhea in a subject; and/or treat or inhibit relapse of *C. difficile*-mediated disease. When administered to a mammal, the present antibodies or antigen-binding portions thereof protect the mammal against toxin A administered in an amount that would be fatal to the mammal had the antibody or antigen-binding portion thereof not administered.

The present antibodies or antigen-binding portions thereof include antibodies produced by hybridoma clone CAN20G2, CAN20G1, CAN20G5, CAN20G8, CAN19G1, CAN19G2 or CAN19G3 described herein.

Also encompassed by the present invention are antibodies or antigen-binding portions thereof that include an antigen-binding portion of an antibody produced by hybridoma clone CAN20G2, CAN20G1, CAN20G5, CAN20G8, CAN19G1, CAN19G2 or CAN19G3.

As used herein, CAN20G1, CAN20G2, CAN20G5, CAN20G8, CAN19G1, CAN19G2 and CAN19G3 refer to the hybridoma clones or the monoclonal antibodies generated by the corresponding hybridoma clones.

The antibodies or antigen-binding portions thereof can specifically bind to an epitope within fragment 4 of toxin A, e.g., an epitope between amino acid residues 1853-2710 of toxin A. Babcock, G. J. et al., Infection and Immunity, 74: 6339-6347 (2006). In other embodiments, the antibodies or antigen-binding portions thereof specifically bind to an epitope within fragment 1 (amino acid residues 1-659), fragment 2 (amino acid residues 660-1256) or fragment 3 (amino acid residues 1257-1852) of toxin A. In other embodiments, the antibodies or antigen-binding portions thereof specifically bind an epitope within amino acid residues 1-600, 400-600, 415-540, 1-100, 100-200, 200-300, 300-400, 400-500, 500-600, 600-700, 700-800, 900-1000, 1100-1200, 1200-1300, 1300-1400, 1400-1500, 1500-1600, 1600-1700, 1800-1900, 1900-200, 2100-2200 or 2200-2300, 2300-2400, 2400-2500, 2500-2600, 2600-2710 of toxin A, or any interval, portion or range thereof.

The present antibodies, or antigen-binding portions thereof, include, but are not limited to, monoclonal antibodies, chimeric antibodies, humanized antibodies, polyclonal antibodies, recombinant antibodies, as well as antigen-binding portions of the foregoing. An antigen-binding portion of an antibody may include a portion of an antibody that specifically binds to a toxin of *C. difficile* (e.g., toxin A).

The humanized antibody of the present invention is an antibody from a non-human species where the amino acid sequence in the non-antigen binding regions (and/or the antigen-binding regions) has been altered so that the antibody more closely resembles a human antibody, and still retains its original binding ability.

Humanized antibodies can be generated by replacing sequences of the variable region that are not directly involved in antigen binding with equivalent sequences from human variable regions. Those methods include isolating, manipulating, and expressing the nucleic acid sequences that encode all or part of variable regions from at least one of a heavy or light chain. Sources of such nucleic acid are well known to those skilled in the art and, for example, may be obtained from a hybridoma producing an antibody against toxin A. The recombinant DNA encoding the humanized antibody, or fragment thereof, can then be cloned into an appropriate expression vector.

An antibody light or heavy chain variable region consists of a framework region interrupted by three hypervariable regions, referred to as complementarity determining regions (CDRs). In one embodiment, humanized antibodies are antibody molecules from non-human species having one, two or all CDRs from the non-human species and a framework region from a human immunoglobulin molecule.

The humanized antibodies of the present invention can be produced by methods known in the art. For example, once non-human (e.g., murine) antibodies are obtained, variable regions can be sequenced, and the location of the CDRs and framework residues determined. Kabat, E. A., et al. (1991) Sequences of Proteins of Immunological Interest, Fifth Edition, U.S. Department of Health and Human Services, NIH Publication No. 91-3242. Chothia, C. et al. (1987) J. Mol. Biol., 196:901-917. The light and heavy chain variable regions can, optionally, be ligated to corresponding constant regions. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in Table 1) or only some of the CDRs may be replaced. It is only necessary to keep the CDRs required for binding of the antibody to a predetermined antigen (e.g., toxin A of *C. difficile*). Morrison, S. L., 1985, Science, 229:1202-1207. Oi et al., 1986, BioTechniques, 4:214. U.S. Pat. Nos. 5,585,089; 5,225,539; 5,693,761 and 5,693,762. EP 519596. Jones et al., 1986, Nature, 321:552-525. Verhoeyan et al., 1988, Science, 239:1534. Beidler et al., 1988, J. Immunol., 141:4053-4060.

Also encompassed by the present invention are antibodies or antigen-binding portions thereof containing one, two, or all CDRs as disclosed herein, with the other regions replaced by sequences from at least one different species including, but not limited to, human, rabbits, sheep, dogs, cats, cows, horses, goats, pigs, monkeys, apes, gorillas, chimpanzees, ducks, geese, chickens, amphibians, reptiles and other animals.

A chimeric antibody is a molecule in which different portions are derived from different animal species. For example, an antibody may contain a variable region derived from a murine mAb and a human immunoglobulin constant region. Chimeric antibodies can be produced by recombinant DNA techniques. Morrison, et al., Proc Natl Acad Sci, 81:6851-6855 (1984). For example, a gene encoding a murine (or other species) monoclonal antibody molecule is digested with restriction enzymes to remove the region encoding the murine Fc, and the equivalent portion of a gene encoding a human Fc constant region is substituted. Chimeric antibodies can also be created by recombinant DNA techniques where DNA encoding murine V regions can be ligated to DNA encoding the human constant regions. Better et al., Science, 1988, 240:1041-1043. Liu et al. PNAS, 1987 84:3439-3443. Liu et al., J. Immunol., 1987, 139:3521-

3526. Sun et al. PNAS, 1987, 84:214-218. Nishimura et al., Canc. Res., 1987, 47:999-1005. Wood et al. Nature, 1985, 314:446-449. Shaw et al., J. Natl. Cancer Inst., 1988, 80:1553-1559. International Patent Publication Nos. WO1987002671 and WO 86/01533. European Patent Application Nos. 184, 187; 171,496; 125,023; and 173,494. U.S. Pat. No. 4,816,567.

The antibodies can be full-length or can include a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al., Proc. Natl. Acad. Sci. USA, 1988, 85:5879-5883.

The antibodies or antigen-binding portions thereof of the present invention may be monospecific, bi-specific or multispecific. Multispecific or bi-specific antibodies or fragments thereof may be specific for different epitopes of one target polypeptide (e.g., toxin A) or may contain antigen-binding domains specific for more than one target polypeptide (e.g., antigen-binding domains specific for toxin A and toxin B; or antigen-binding domains specific for toxin A and other antigen of *C. difficile*; or antigen-binding domains specific for toxin A and other kind of bacterium or virus). In one embodiment, a multispecific antibody or antigen-binding portion thereof comprises at least two different variable domains, wherein each variable domain is capable of specifically binding to a separate antigen or to a different epitope on the same antigen. Tuft et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for toxin A, and the other arm of the immunoglobulin is specific for a second therapeutic target or is conjugated to a therapeutic moiety such as a trypsin inhibitor.

All antibody isotypes are encompassed by the present invention, including IgG (e.g., IgG1, IgG2, IgG3, IgG4), IgM, IgA (IgA1, IgA2), IgD or IgE. The antibodies or antigen-binding portions thereof may be mammalian (e.g., mouse, human) antibodies or antigen-binding portions thereof. The light chains of the antibody may be of kappa or lambda type.

The CDRs of the present antibodies or antigen-binding portions thereof can be from a non-human or human source. The framework of the present antibodies or antigen-binding portions thereof can be human, humanized, non-human (e.g., a murine framework modified to decrease antigenicity in humans), or a synthetic framework (e.g., a consensus sequence).

In one embodiment, the present antibodies, or antigen-binding portions thereof, contain at least one heavy chain variable region and/or at least one light chain variable region. The heavy chain variable region (or light chain variable region) contains three CDRs and four framework regions (FRs), arranged from amino-terminus to carboxy-terminus in the following order: FR1, CDR1, FR2, CDR2, FR3, CDR3, FR4. Kabat, E. A., et al. Sequences of Proteins of Immunological Interest, Fifth Edition, U.S. Department of Health and Human Services, NIH Publication No. 91-3242, 1991. Chothia, C. et al., J. Mol. Biol. 196:901-917, 1987.

The present antibodies or antigen-binding portions thereof specifically bind to toxin A with a dissociation constant ($K_D$) of less than about $10^{-7}$ M, less than about $10^{-8}$ M, less than about $10^{-9}$ M, less than about $10^{-10}$ M, less than about $10^{-11}$ M, or less than about $10^{-12}$ M.

Antibodies with a variable heavy chain region and a variable light chain region that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to the variable heavy chain region and variable light chain region of the antibody produced by clone CAN20G1, CAN20G2, CAN20G5, CAN20G8, CAN19G1, CAN19G2 or CAN19G3 can also bind to toxin A.

In related embodiments, anti-toxin A antibodies or antigen-binding portions thereof include, for example, the CDRs of variable heavy chains and/or variable light chains of CAN20G1, CAN20G2, CAN20G5, CAN20G8, CAN19G1, CAN19G2 or CAN19G3. The CDRs of the variable heavy chain regions from these clones, as well as the CDRs of the variable light chain regions from these clones, are shown in Table 1.

TABLE 1

Seq ID Nos. 3-104

| Name | Chain, Region | Sequence | Seq ID No. |
|---|---|---|---|
| Fragment 4 of Toxin A | | GWQTINGKKYYFDINTGAALISYKIINGKHFYFNNDG<br>VMQLGVFKGPDGFEYFAPANTQNNNIEGQAIVYQSK<br>FLTLNGKKYYFDNDSKAVTGWRIINNEKYYFNPNNA<br>IAAVGLQVIDNNKYYFNPDTAIISKGWQTVNGSRYYF<br>DTDTAIAFNGYKTIDGKHFYFDSDCVVKIGVFSTSNG<br>FEYFAPANTYNNNIEGQAIVYQSKFLTLNGKKYYFD<br>NNSKAVTGWQTIDSKKYYFNTNTAEAATGWQTIDG<br>KKYYFNTNTAEAATGWQTIDGKKYYFNTNTAIASTG<br>YTIINGKHFYFNTDGIMQIGVFKGPNGFEYFAPANTD<br>ANNIEGQAILYQNEFLTLNGKKYYFGSDSKAVTGWR | 3 |

TABLE 1-continued

Seq ID Nos. 3-104

| Name | Chain, Region | Sequence | Seq ID No. |
|---|---|---|---|
| | | IINNKKYYFNPNNAIAAIHLCTINNDKYYFSYDGILQN<br>GYITIERNNFYFDANNESKMVTGVFKGPNGFEYFAPA<br>NTHNNNIEGQAIVYQNKFLTLNGKKYYFDNDSKAVT<br>GWQTIDGKKYYFNLNTAEAATGWQTIDGKKYYFNL<br>NTAEAATGWQTIDGKKYYFNTNTFIASTGYTSINGKH<br>FYFNTDGIMQIGVFKGPNGFEYFAPANTHNNNIEGQA<br>ILYQNKFLTLNGKKYYFGSDSKAVTGLRTIDGKKYY<br>FNTNTAVAVTGWQTINGKKYYFNTNTSIASTGYTIIS<br>GKHFYFNTDGIMQIGVFKGPDGFEYFAPANTDANNIE<br>GQAIRYQNRFLYLHDNIYYFGNNSKAATGWVTIDGN<br>RYYFEPNTAMGANGYKTIDNKNFYFRNGLPQIGVFK<br>GSNGFEYFAPANTDANNIEGQAIRYQNRFLHLLGKIY<br>YFGNNSKAVTGWQTINGKVYYFMPDTAMAAAGGLF<br>EIDGVIYFFGVDGVKAPGIYG | |
| CAN20G1 | K, variable region | QVVLTQSPAIMSASLGERVTMTCTASSSVISSYLHWY<br>QQKPGSSPKLWIYSTSTLASGVPARFSGSGSGTSYSLT<br>ISSMEAEDAATYYCLQYHRSPRTFGGGTKLEIK | 4 |
| CAN20G 1 | K, CDR1 | SSVISSY | 5 |
| CAN20G1 | K, CDR2 | STS | 6 |
| CAN20G1 | K, CDR3 | CLQYHRSPRTF | 7 |
| CAN20G1 | K, FR1 | QVVLTQSPAIMSASLGERVTMTCTAS | 8 |
| CAN20G1 | K, FR2 | LHWYQQKPGSSPKLWIY | 9 |
| CAN20G1 | K, FR3 | TLASGVPARFSGSGSGTSYSLTISSMEAEDAATYY | 10 |
| CAN20G1 | K, FR4 | GGGTKLEIK | 11 |
| CAN20G1 | H, variable region | QIQLVQSGPELKKPGETVKISCKASGYTFTNDGMNW<br>VKQAPGKGLKWMGWINTNTGEPTYVEEFKGRFAFS<br>LETSASTAYLQINNLKNEDTATYFCYVNYDYYTMDC<br>WGQGTSVTVSS | 12 |
| CAN20G1 | H, CDR1 | GYTFTNDG | 13 |
| CAN20G1 | H, CDR2 | INTNTGEP | 14 |
| CAN20G1 | H, CDR3 | CYVNYDYYTMDCW | 15 |
| CAN20G1 | H, FR1 | QIQLVQSGPELKKPGETVKISCKAS | 16 |
| CAN20G1 | H, FR2 | MNWVKQAPGKGLKWMGW | 17 |
| CAN20G1 | H, FR3 | TYVEEFKGRFAFSLETSASTAYLQINNLKNEDTATYF | 18 |
| CAN20G1 | H, FR4 | GQGTSVTVSS | 19 |
| CAN20G2 | K, variable region | QVVLTQSPAIMSASLGDRVTMTCTASSSVISTYLHWY<br>QQKPGSSPKLWIYSTSTLASGVPPRFSGSGSGTSYSLT<br>ISSMEAEDAATYYCLQYHRSPRTFGGGTKLEIK | 20 |
| CAN20G2 | K, CDR1 | SSVISTY | 21 |
| CAN20G2 | K, CDR2 | STS | 22 |

TABLE 1-continued

Seq ID Nos. 3-104

| Name | Chain, Region | Sequence | Seq ID No. |
|---|---|---|---|
| CAN20G2 | K, CDR3 | LQYHRSPRT | 23 |
| CAN20G2 | K, FR1 | QVVLTQSPAIMSASLGDRVTMTCTAS | 24 |
| CAN20G2 | K, FR2 | LHWYQQKPGSSPKLWIY | 25 |
| CAN20G2 | K, FR3 | TLASGVPPRFSGSGSGTSYSLTISSMEAEDAATYYC | 26 |
| CAN20G2 | K, FR4 | FGGGTKLEIK | 27 |
| CAN20G2 | H, variable region | QIQLVQSGPEVKKPGETVKISCKASGYTFTNQGMNW VKQAPGKGLKWMGWINTNTGEPTYTEEFKGRFAFSL ETSASTAYLQINNLKNEDTATYFCYVNYDYYTMDF WGQGTSVTVSS | 28 |
| CAN20G2 | H, CDR1 | GYTFTNQG | 29 |
| CAN20G2 | H, CDR2 | INTNTGEP | 30 |
| CAN20G2 | H, CDR3 | YVNYDYYTMDF | 31 |
| CAN20G2 | H, FR1 | QIQLVQSGPEVKKPGETVKISCKAS | 32 |
| CAN20G2 | H, FR2 | MNWVKQAPGKGLKWMGW | 33 |
| CAN20G2 | H, FR3 | TYTEEFKGRFAFSLETSASTAYLQINNLKNEDTATYF C | 34 |
| CAN20G2 | H, FR4 | WGQGTSVTVSS | 35 |
| CAN20G5 | K, variable region | QIVLTQSPAIMSASLGERVTMTCTASSSVYSTYLHWY QQKPGSSPKLWIYSTSNLASGVPARFSGSGSGTSYSL TISSMEAEDAATYYCHQYHRSPRTFGGGTKLEIK | 36 |
| CAN20G5 | K, CDR1 | SSVYSTY | 37 |
| CAN20G5 | K, CDR2 | STS | 38 |
| CAN20G5 | K, CDR3 | CHQYHRSPRTF | 39 |
| CAN20G5 | K, FR1 | QIVLTQSPAIMSASLGERVTMTCTAS | 40 |
| CAN20G5 | K, FR2 | LHWYQQKPGSSPKLWIY | 41 |
| CAN20G5 | K, FR3 | NLASGVPARFSGSGSGTSYSLTISSMEAEDAATYY | 42 |
| CAN20G5 | K, FR4 | GGGTKLEIK | 43 |
| CAN20G5 | H, variable region | QIQLVQSGPELKKPGETVKISCKASGYSFTNSGMNW VKEAPGKGLKWMGWINTNTGEPTYAEEFMGRFAFS LETSASTAYLQINNLKNEDTATYFCYVNYDYYTIDY WGQGTSVTVSS | 44 |
| CAN20G5 | H, CDR1 | GYSFTNSG | 45 |

TABLE 1-continued

Seq ID Nos. 3-104

| Name | Chain, Region | Sequence | Seq ID No. |
|---|---|---|---|
| CAN20G5 | H, CDR2 | INTNTGEP | 46 |
| CAN20G5 | H, CDR3 | CYVNYDYYTIDYW | 47 |
| CAN20G5 | H, FR1 | QIQLVQSGPELKKPGETVKISCKAS | 48 |
| CAN20G5 | H, FR2 | MNWVKEAPGKGLKWMGW | 49 |
| CAN20G5 | H, FR3 | TYAEEFMGRFAFSLETSASTAYLQINNLKNEDTATYF | 50 |
| CAN20G5 | H, FR4 | GQGTSVTVSS | 51 |
| CAN20G8 | K, variable region | QVVLTQSPAIMSASLGERVTMTCTASSSVISSYLHWY<br>QQKPGSSPKLWIYSTSILASGVPARFSGSGSGTSYSLTI<br>SSMEAEDAATYYCLQYHRSPRTFGGGTKLEIK | 52 |
| CAN20G8 | K, CDR1 | SSVISSY | 53 |
| CAN20G8 | K, CDR2 | STS | 54 |
| CAN20G8 | K, CDR3 | CLQYHRSPRTF | 55 |
| CAN20G8 | K, FR1 | QVVLTQSPAIMSASLGERVTMTCTAS | 56 |
| CAN20G8 | K, FR2 | LHWYQQKPGSSPKLWIY | 57 |
| CAN20G8 | K, FR3 | ILASGVPARFSGSGSGTSYSLTISSMEAEDAATYY | 58 |
| CAN20G8 | K, FR4 | GGGTKLEIK | 59 |
| CAN20G8 | H, variable region | QIQLVQSGPELKKPGETVKISCKASGYAFTNDGMNW<br>VKQAPGKGLKWMGWINTNTGEPTYAEEFKGRFAFS<br>LETSASTAYLQINNLKNEDTATYFCYVNYDYYTMDC<br>WGQGTSVTVSS | 60 |
| CAN20G8 | H, CDR1 | GYAFTNDG | 61 |
| CAN20G8 | H, CDR2 | INTNTGEP | 62 |
| CAN20G8 | H, CDR3 | CYVNYDYYTMDCW | 63 |
| CAN20G8 | H, FR1 | QIQLVQSGPELKKPGETVKISCKAS | 64 |
| CAN20G8 | H, FR2 | MNWVKQAPGKGLKWMGW | 65 |
| CAN20G8 | H, FR3 | TYAEEFKGRFAFSLETSASTAYLQINNLKNEDTATYF | 66 |
| CAN20G8 | H, FR4 | GQGTSVTVSS | 67 |
| CAN20G1 Kappa | | Caagttgttctcacccagtctccagcaatcatgtctgcatctctaggggaacgggtca<br>ccatgacctgcactgccagctcaagtgtaatttccagttatttgcactggtaccagcag<br>aagccaggatcctcccccaaactctggatttatagcacatccaccctggcttctggag<br>tcccagctcgcttcagtggcagtgggtctgggacctcttactctctcacaatcagcag<br>catggaggctgaagatgctgccacttattactgcctccagtatcatcgttccccacgg<br>acgttcggtggaggcaccaagctggaaatcaaacgggctgatgctgcaccaactgt | 68 |

TABLE 1-continued

| Seq ID Nos. 3-104 | | | |
|---|---|---|---|
| Name | Chain, Region | Sequence | Seq ID No. |
| | | atccatcttcccaccatccagtgagcagttaacatctggaggtgcctcagtcgtgtgc ttcttgaacaacttctaccccaaagacatcaatgtcaagtggaagattgatggcagtg aacgacaaaatggcgtcctgaacagttggactgatcaggacagcaaagacagcac aag | |
| CAN20G1 Heavy | | Cagatccagttggtgcagtctggacctgagctgaagaagcctggagagacagtca agatctcctgcaaggcttctgggtataccttcacaaacgatggaatgaactgggtga aacaggctccaggaaagggtttaaagtggatgggctggataaacaccaacactgg agagccaacatatgttgaagagttcaagggacggtttgccttctctttagaaacctctg ccagcactgcctatttgcagatcaacaacctcaaaaatgaggacacggctacatattt ctgttatgttaactacgattattatactatggactgctggggtcaaggaacctcagtcac cgtctcctcagccaaaacgacacccccatctgtctatccactggcccctggatctgct gcccaaactaactccatggtgaccctgggatgcctggtcaagggctatttccctgag ccagtgacagtgacctggaactctggatccctgtccagcggtgtgcacaccttccca gctstcctaag | 69 |
| CAN20G2 Kappa | | Caagttgttctcacccagtctccagcaatcatgtctgcatctctaggggatcggtca ccatgacctgcactgccagctcaagtgtaatttccacttacttgcactggtatcagcag aagccaggatcctcccccaaactctggatttatagcacatccaccctggcttctggag tcccacctcgcttcagtggcagtgggtctgggacctcttactctctcacaatcagcag catggaggctgaagatgctgccacttattactgcctccagtatcaccgttccccacgg acgttcggtggaggcaccaagctggaaatcaaacgggctgatgctgcaccaactgt atccatcttcccaccatccagtgagcagttaacatctggaggtgcctcagtcgtgtgc ttcttgaacaacttctaccccaaagacatcaatgtcaagtggaagattgatggcagtg aacgacaaaatggcgtcctgaacagttggactgatcaggacagcaaagacagcac aag | 70 |
| CAN20G2 Heavy | | Cagatccagttggtgcagtctggacctgaggtgaagaagcctggagagacagtca agatctcctgcaaggcttctgggtataccttcacaaaccaaggaatgaactgggtga aacaggctccaggaaagggtttaaagtggatgggctggataaacaccaacactgg agagccaacatatactgaagagttcaagggacggtttgccttctctttagaaacctct gccagcactgcctatttgcagatcaacaacctcaaaaatgaggacacggctacatat ttctgttatgttaactacgattattatactatggacttctggggtcaaggaacctcggtca ccgtctcctcagccaaaacaacagccccatcggtctatccactggcccctgtgtgtg gagatacaactggctcctcggtgactctaggatgcctggtcaagggttatttccctga gccagtgaccttgacctggaactctggatccctgtccagtggtgtgcacaccttccca gctstcctaag | 71 |
| CAN20G5 Kappa | | Caaattgttctcacccagtctccagcaatcatgtctgcttctctaggggaacgggtca ccatgacctgcactgccagctcaagtgtatattccacttacttgcactggtaccagca gaagccaggatcctcccccaaactctggatttatagcacatccaacctggcttctgga gtcccagctcgcttcagtggcagtgggtctgggacctcttactctctcacaatcagca gcatggaggctgaagatgctgccacttattactgccaccagtatcatcgttccccacg gacgttcggtggaggcaccaagctggaaatcaaacgggctgatgctgcaccaact gtatccatcttcccaccatccagtgagcagttaacatctggaggtgcctcagtcgtgt gcttcttgaacaacttctaccccaaagacatcaatgtcaagtggaagattgatggcag tgaacgacaaaatggcgtcctgaacagttggactgatcaggacagcaaagacagc acaag | 72 |
| CAN20G5 Heavy | | Cagatccagttggtacagtctggacctgagctgaagaagcctggagagacagtca agatctcctgcaaggcttctgggtattccttcacaaactctggaatgaactgggtgaa agaggctccaggaaagggtttaaagtggatgggctggataaacaccaacactgga gagccaacatatgctgaagaattcatgggacggtttgccttctctttggaaacctctgc cagcactgcctatttgcagatcaacaacctcaaaaatgaagacacggctacatatttc tgttatgttaactacgattactatactatagactactggggtcaaggaacctcagtcac cgtctcctcagccaaaacgacacccccatctgtctatccactggcccctggatctgct gcccaaactaactccatggtgaccctgggatgcctggtcaagggctatttccctgag ccagtgacagtgacctggaactctggatccctgtccagcggtgtgcacaccttccca gctstcctaag | 73 |
| CAN20G8 Kappa | | Cactggtaccagcagaagccaggatcctcccccaaactctggatttatagcacatc catcctggcttctggagtcccagctcgcttcagtggcagtgggtctgggacctcttac tctctcacaatcagcagcatggaggctgaagatgctgccacttattactgcctccagt atcatcgttccccacggacgttcggtggaggcaccaagctggaaatcaaacgggct gatgctgcaccaactgtatccatcttcccaccatccagtgagcagttaacatctggag gtgcctcagtcgtgtgcttcttgaacaacttctaccccaaagacatcaatgtcaagtgg aagattgatggcagtgaacgacaaaatggcgtcctgaacagttggactgatcagga cagcaaagacagcacaag | 74 |
| CAN20G8 Heavy | | Cagatccagttggtgcagtctggacctgagctgaagaagcctggagagacagtca agatctcctgcaaggcttctgggtatgccttcacaaacgatggaatgaactgggtga aacaggctccaggaaagggtttaaagtggatgggctggataaacaccaacactgg agagccaacatatgctgaagagttcaagggacggtttgccttctctttagaaacctct gccagcactgcctatttgcagatcaacaacctcaaaaatgaggacacggctacatat ttctgttatgttaactacgattattatactatggactgctggggtcaaggaacctcagtc | 75 |

TABLE 1-continued

Seq ID Nos. 3-104

| Name | Chain, Region | Sequence | Seq ID No. |
|---|---|---|---|
| | | accgtctcctcagccaaaacgacacccccatctgtctatccactggcccctggatct gctgcccaaactaactccatggtgaccctgggatgcctggtcaagggctatttccct gagccagtgacagtgacctggaactctggatccctgtccagcggtgtgcacaccttc ccagctstcctaag | |
| 5'mVK-Lead-1 | | GGTGCAGATTTTCAGCTTCC | 76 |
| 3'Kappa ConstRT | | GTGCTGTCTTTGCTGTCCTG | 77 |
| 5'mVH-Lead-2 | | BTNCTYYTCTKCCTGRT | 78 |
| 5'mVH-Lead-2A | | TGGSTGTGGAMCTTGCTATT | 79 |
| 3'mIG1-2C RT | | AGGASAGCTGGGAAGGTGTG | 80 |
| 5'mVK-Lead-3 | | CTWKGRSTKCTGCTKYTCTG | 81 |
| 5'mVK-Lead-3A | | CCTGTTAGGCTGTTGGTGCT | 82 |
| 5'mVH-IGHV1-Lead | | RKCARCARCTRCAGGTGTCC | 83 |
| 5'mVH-Lead-1 | | CCYWNTTTTAMAWGGTGTCCAKTGT | 84 |
| 5'mVH-Lead-3 | | GGATGGAGCTRTATCATBCTC | 85 |
| 5'mVH-Lead-4 | | GRTCTTTMTYTTHHTCCTGTCA | 86 |
| 5'mVH-Lead-5 | | VCCTTWMMTGGTATCCWGTST | 87 |
| CDR-huCAN20 G2 (FIG. 13A) | H, variable region | GCCGCCACCATGGCATGCCCTGGCTTCCTGTGGGC ACTTGTGATCTCCACCTGTCTTGAATTTTCCATGGC TCaggtgcagctggtgcaatctgggtctgagttgaagaagcctggggcctcagtg aaggtttcctgcaaggcttctGGGTATACCTTCACAAACCAAG GAAtgaattgggtgcgacaggcccctggacaagggcttgagtggatgggatgg ATAAACACCAACACTGGAGAGCCAAcgtatgcccagggctt cacaggacggtttgtcttctccttggacacctctgtcagcacggcatatctgcagatc agcagcctaaaggctgaggacactgccgtgtattactgtTATgtcaatTACGA TTATTATACTATGGACTTCtgggggcaagggaccacggtcaccgt ctcctca | 88 |
| CDR-huCAN20G2 (FIG. 13A) | H, variable region | QVQLVQSGSELKKPGASVKVSCKASGYTFTNQGMN WVRQAPGQGLEWMGWINTNTGEPTYAQGFTGRFVF SLDTSVSTAYLQISSLKAEDTAVYYCYVNYDYYTMD FWGQGTTVTVSS | 89 |
| CDR-huCAN20G2 (FIG. 13B) | K, variable region | GCCGCCACCATGGCATGCCCTGGCTTCCTGTGGGC ACTTGTGATCTCCACCTGTCTTGAATTTTCCATGGC TGacatccagatgacccagtctccatcctccctgtctgcatctgtaggagacagagt caccatcacttgccgggcaagtTCAAGTGTAATTTCCACTTACT taaattggtatcagcagaaaccagggaaagcccctaagctcctgatctatAGCA CATCCAgtttgcaaagtggggteccatcaaggttcagtggcagtggatctggg acagatttcactctcaccatcagcagtctgcaacctgaagattttgcaacttactactgt CTCCAGTATCACCGTTCCCCACGGACGttcggcggaggga ccaaggtggagatcaaa | 90 |
| CDR-huCAN20G2 (FIG. 13B) | K, variable region | DIQMTQSPSSLSASVGDRVTITCRASSSVISTYLNWYQ QKPGKAPKLLIYSTSSLQSGVPSRFSGSGSGTDFTLTIS SLQPEDFATYYCLQYHRSPRTFGGGTKVEIK | 91 |
| HE-huCAN20G2 (FIG. 14A) | H, variable region | GCCGCCACCATGGCATGCCCTGGCTTCCTGTGGGC ACTTGTGATCTCCACCTGTCTTGAATTTTCCATGGC TCAGatcCAGttgGTGcagTCTggaCCTgag**CTG**aagAAGcct | 92 |

TABLE 1-continued

Seq ID Nos. 3-104

| Name | Chain, Region | Sequence | Seq ID No. |
|---|---|---|---|
| | | GGAgagACAgtcAAGatcTCCtgcAAGgctTCTgggTATaccT<br>TCacaAACcaaGGAatgAACtggGTGaaaCAGgctCCAggaA<br>AGggtTTAaagTGGatgGGCtggATAaacACCaacACTggaG<br>AGccaACAtatACTGCCGATttcACAggaCGGtttGCCttcTC<br>TttaGAAaccTCTGTGAGCactGCCtatTTGcagATCaacTC<br>CctcAAAGCTGAGgacACGgctACAtatTTCtgtTATgtcaatta<br>cGATtatTATactATGgacTTCTGGGGTCAAGGAaccCTG<br>gtcACCgtcTCCtca | |
| HE-huCAN20G2 (FIG. 14A) | H, variable region | QIQLVQSGPELKKPGETVKISCKASGYTFTNQGMNW<br>VKQAPGKGLKWMGWINTNTGEPTYTADFTGRFAFS<br>LETSVSTAYLQINSLKAEDTATYFCYVNYDYYTMDF<br>WGQGTLVTVSS | 93 |
| HE-huCAN20G2 (FIG. 14B) | K, variable region | GCCGCCACCATGGCATGCCCTGGCTTCCTGTGGGC<br>ACTTGTGATCTCCACCTGTCTTGAATTTTCCATGGC<br>TGACgttCAGctcACCcagTCTccaAGCatcATGtctGCAtctC<br>TAgggGATcggGTCaccATGaccTGCactGCCagcTCAagtGT<br>AattTCCactTACttgCACtggTATcagCAGaagCCAggaTCCtc<br>cCCCaaaCTCtggATTtatAGCacaTCCaccCTGgctTCTggaG<br>TCccaAGCcgcTTCagtGGCagtGGGtctGGGaccGACtacTC<br>TctcACAatcAGCagcATGgagCCTgaaGATgctGCCactTAT<br>tacTGCctcCAGtatCACcgtTCCccaCGGacgTTCggtGGAgg<br>cACCaagGTGgaaATCaaa | 94 |
| HE-huCAN20G2 (FIG. 14B) | K, variable region | DVQLTQSPSIMSASLGDRVTMTCTASSSVISTYLHWY<br>QQKPGSSPKLWIYSTSTLASGVPPRFSGSGSGTDYSLT<br>ISSMEPEDAATYYCLQYHRSPRTFGGGTKVEIK | 95 |
| HE-huCAN20G2 (FIG. 15) | H | GCCGCCACCATGGCATGCCCTGGCTTCCTGTGGGC<br>ACTTGTGATCTCCACCTGTCTTGAATTTTCCATGGC<br>TCAGatcCAGttgGTGcagTCTggaCCTgagCTGaagAAGcct<br>GGAgagACAgtcAAGatcTCCtgcAAGgctTCTgggTATaccT<br>TCacaAACcaaGGAatgAACtggGTGaaaCAGgctCCAggaA<br>AGggtTTAaagTGGatgGGCtggATAaacACCaacACTggaG<br>AGccaACAtatACTGCCGATttcACAggaCGGtttGCCttcTC<br>TttaGAAaccTCTGTGAGCactGCCtatTTGcagATCaacTC<br>CctcAAAGCTGAGgacACGgctACAtatTTCtgtTATgtcaatta<br>cGATtatTATactATGgacTTCTGGGGTCAAGGAaccCTG<br>gtcACCgtcTCCtcaGGTGAGTGCGGCCGCGAGCCCAG<br>ACACTGGACGCTGAACCTCGCGGACAGTTAAGAAC<br>CCAGGGGCCTCTGCGCCCTGGGCCCAGCTCTGTCC<br>CACACCGCGGTCACATGGCACCACCTCTCTTGCAG<br>CCTCCACCAAGGGCCCATCGGTCTTCCCCCTGG<br>CACCCTCCTCCAAGAGCACCTCTGGGGGCACAG<br>CGGCCCTGGGCTGCCTGGTCAAGGACTACTTCC<br>CCGAACCGGTGACGGTGTCGTGGAACTCAGGC<br>GCCCTGACCAGCGGCGTGCACACCTTCCCGGCT<br>GTCCTACAGTCCTCAGGACTCTACTCCCTCAGC<br>AGCGTGGTGACCGTGCCCTCCAGCAGCTTGGGC<br>ACCCAGACCTACATCTGCAACGTGAATCACAAG<br>CCCAGCAACACCAAGGTGGACAAGAGAGTTGGT<br>GAGAGGCCAGCACAGGGAGGGAGGGTGTCTGCTG<br>GAAGCCAGGCTCAGCGCTCCTGCCTGGACGCATCC<br>CGGCTATGCAGTCCCAGTCCAGGGCAGCAAGGCAG<br>GCCCCGTCTGCCTCTTCACCCGGAGGCCTCTGCCC<br>GCCCCACTCATGCTCAGGGAGAGGGTCTTCTGGCT<br>TTTTCCCCAGGCTCTGGGCAGGCACGGGCTAGGTG<br>CCCCTAACCCAGGCCCTGCACACAAAGGGGCAGGT<br>GCTGGGCTCAGACCTGCCAAGAGCCATATCCGGGA<br>GGACCCTGCCCCTGACCTAAGCCCACCCCAAAGGC<br>CAAACTCTCCACTCCCTCAGCTCGGACACCTTCTCT<br>CCTCCCAGATTCCAGTAACTCCCAATCTTCTCTCTG<br>CAGAGCCCAAATCTTGTGACAAAACTCACACAT<br>GCCCACCGTGCCCAGGTAAGCCAGCCCAGGCCTC<br>GCCCTCCAGCTCAAGGCGGGACAGGTGCCCTAGAG<br>TAGCCTGCATCCAGGGACAGGCCCCAGCCGGGTGC<br>TGACACGTCCACCTCCATCTCTTCCTCAGCACCTG<br>AACTCCTGGGGGGACCGTCAGTCTTCCTCTTCC<br>CCCCAAAACCCAAGGACACCCTCATGATCTCCC<br>GGACCCCTGAGGTCACATGCGTGGTGGTGGAC<br>GTGAGCCACGAAGACCCTGAGGTCAAGTTCAAC<br>TGGTACGTGGACGGCGTGGAGGTGCATAATGCC<br>AAGACAAAGCCGCGGGAGGAGCAGTACAACAG<br>CACGTACCGTGTGGTCAGCGTCCTCACCGTCCT | 96 |

TABLE 1-continued

| Seq ID Nos. 3-104 | | | |
|---|---|---|---|
| Name | Chain, Region | Sequence | Seq ID No. |
| | | GCACCAGGACTGGCTGAATGGCAAGGAGTACAA<br>GTGCAAGGTCTCCAACAAAGCCCTCCCAGCCCC<br>CATCGAGAAAACCATCTCCAAAGCCAAAGGTGG<br>GACCCGTGGGGTGCGAGGGCCACATGGACAGAGG<br>CCGGCTCGGCCCACCCTCTGCCCTGAGAGTGACCG<br>CTGTACCAACCTCTGTCCCTACAGGGCAGCCCCG<br>AGAACCACAGGTGTACACCCTGCCCCCATCCCG<br>GGAGGAGATGACCAAGAACCAGGTCAGCCTGA<br>CCTGCCTGGTCAAAGGCTTCTATCCCAGCGACA<br>TCGCCGTGGAGTGGGAGAGCAATGGGCAGCCG<br>GAGAACAACTACAAGACCACGCCTCCCGTGCTG<br>GACTCCGACGGCTCCTTCTTCCTCTATAGCAAG<br>CTCACCGTGGACAAGAGCAGGTGGCAGCAGGG<br>GAACGTCTTCTCATGCTCCGTGATGCATGAGGC<br>TCTGCACAACCACTACACGCAGAAGAGCCTCTC<br>CCTGTCTCCGGGTAAATGATGAGCTAGC | |
| HE-huCAN20G2 (FIG. 15) | H | QIQLVQSGPELKKPGETVKISCKASGYTFTNQGMNW<br>VKQAPGKGLKWMGWINTNTGEPTYTADFTGRFAFS<br>LETSVSTAYLQINSLKAEDTATYFCYVNYDYYTMDF<br>WGQGTLVTVSSASTKGPSVFPLAPSSKSTSGGTAALG<br>CLVKDYFPEPVTVSWNSGALTSGVHTFPAVLQSSGL<br>YSLSSVVTVPSSSLGTQTYICNVNHKPSNTKVDKRVE<br>PKSCDKTHTCPPCPAPELLGGPSVFLFPPKPKDTLMIS<br>RTPEVTCVVVDVSHEDPEVKFNWYVDGVEVHNAKT<br>KPREEQYNSTYRVVSVLTVLHQDWLNGKEYKCKVS<br>NKALPAPIEKTISKAKGQPREPQVYTLPPSREEMTKN<br>QVSLTCLVKGFYPSDIAVEWESNGQPENNYKTTPPVL<br>DSDGSFFLYSKLTVDKSRWQQGNVFSCSVMHEALH<br>NHYTQKSLSLSPGK | 97 |
| HE-huCAN20G2 (FIG. 16) | K | GCCGCCACCATGGCATGCCCTGGCTTCCTGTGGGC<br>ACTTGTGATCTCCACCTGTCTTGAATTTTCCATGGC<br>TGACgttCAGctcACCcagTCTccaAGCatcATGtctGCAtctC<br>TAgggGATcggGTCaccATGaccTGCactGCCagcTCAagtGT<br>AattTCCactTACttgCACtggTATcagCAGaagCCAggcAGCt<br>ccCCCaaaCTCtggATTtatAGCacaTCCaccCTGgctTCTgga<br>GTCccaAGCcgcTTCagtGGCagtGGGtctGGGaccGACtacT<br>CTctcACAatcAGCagcATGgagCCTgaaGATgctGCCactTA<br>TtacTGCctcCAGtatCACcgtTCCccaCGGacgTTCggtGGAg<br>gcACCaagGTGgaaATCaaaCGTAAGTGCACTTTGCGG<br>CCGCTAGGAAGAAACTCAAAACATCAAGATTTTAA<br>ATACGCTTCTTGGTCTCCTTGCTATAATTATCTGGG<br>ATAAGCATGCTGTTTTCTGTCTGTCCCTAACATGCC<br>CTGTGATTATCCGCAAACAACACACCCAAGGGCAG<br>AACTTTGTTACTTAAACACCATCCTGTTTGCTTCTT<br>TCCTCAGGAACTGTGGCTGCACCATCTGTCTTCA<br>TCTTCCCGCCATCTGATGAGCAGTTGAAATCTG<br>GAACTGCCTCTGTTGTGTGCCTGCTGAATAACT<br>TCTATCCCAGAGAGGCCAAAGTACAGTGGAAGG<br>TGGATAACGCCCTCCAATCGGGTAACTCCCAGG<br>AGAGTGTCACAGAGCAGGACAGCAAGGACAGC<br>ACCTACAGCCTCAGCAGCACCCTGACGCTGAGC<br>AAAGCAGACTACGAGAAACACAAAGTCTACGCC<br>TGCGAAGTCACCCATCAGGGCCTGAGCTCGCCC<br>GTCACAAAGAGCTTCAACAGGGGAGAGTGTTGA<br>TAGTTAACG | 98 |
| HE-huCAN20G2 (FIG. 16) | K | DVQLTQSPSIMSASLGDRVTMTCTASSSVISTYLHWY<br>QQKPGSSPKLWIYSTSTLASGVPPRFSGSGSGTDYSLT<br>ISSMEPEDAATYYCLQYHRSPRTFGGGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC | 99 |
| AVA-huCAN20G2 (FIG. 18) | K | GCCGCCACCATGGCATGCCCTGGCTTCCTGTGGGC<br>ACTTGTGATCTCCACCTGTCTTGAATTTTCCATGGC<br>TGACatcCAGatgACCcagTCTccaTCCtccCTGtctGCAtctG<br>TAggaGACagaGTCaccATCactTGCAGCGCGagtTCAAG<br>TGTAATTTCCACTTACTTAaatTGGtatCAGcagAAAcca<br>GGGaaaGCCcctAAGgtgCTGatcTACAGCACATCCAGCt<br>tgcacagcGGGgtcCCAtcaAGGttcAGTggaAGTggaTCTggg<br>ACAgatTTTactctgaccATCagcAGCctgCAGcctGAAgatttcg<br>caACAtatTACtgtCTCCAGTATCACCGTTCCCCACGGA<br>CGttcggccaagggaccaaggtggaaatcaaaCGTAAGTGCACTTT | 100 |

TABLE 1-continued

Seq ID Nos. 3-104

| Name | Chain, Region | Sequence | Seq ID No. |
|---|---|---|---|
| | | GCGGCCGCTAGGAAGAAACTCAAAACATCAAGAT<br>TTTAAATACGCTTCTTGGTCTCCTTGCTATAATTAT<br>CTGGGATAAGCATGCTGTTTTCTGTCTGTCCCTAAC<br>ATGCCCTGTGATTATCCGCAAACAACACACCCAAG<br>GGCAGAACTTTGTTACTTAAACACCATCCTGTTTGC<br>TTCTTTCCTCAGGAACTGTGGCTGCACCATCTGT<br>CTTCATCTTCCCGCCATCTGATGAGCAGTTGAA<br>ATCTGGAACTGCCTCTGTTGTGTGCCTGCTGAA<br>TAACTTCTATCCCAGAGAGGCCAAAGTACAGTG<br>GAAGGTGGATAACGCCCTCCAATCGGGTAACTC<br>CCAGGAGAGTGTCACAGAGCAGGACAGCAAGG<br>ACAGCACCTACAGCCTCAGCAGCACCCTGACGC<br>TGAGCAAAGCAGACTACGAGAAACACAAAGTCT<br>ACGCCTGCGAAGTCACCCATCAGGGCCTGAGCT<br>CGCCCGTCACAAAGAGCTTCAACAGGGGAGAGT<br>GTTGATAGTTAACG | |
| Chimeric CAN20G2 (FIG. 19A) | H | GCCGCCACCATGGCATGCCCTGGCTTCCTGTGGGC<br>ACTTGTGATCTCCACCTGTCTTGAATTTTCCATGGC<br>TCAGATCCAGTTGGTGCAGTCTGGACCTGAGGTGA<br>AGAAGCCTGGAGAGACAGTCAAGATCTCCTGCAA<br>GGCTTCTGGGTATACCTTCACAAACCAAGGAATGA<br>ACTGGGTGAAACAGGCTCCAGGAAAGGGTTTAAA<br>GTGGATGGGCTGGATAAACACCAACACTGGAGAG<br>CCAACATATACTGAAGAGTTCAAGGGACGGTTTGC<br>CTTCTCTTTAGAAACCTCTGCCAGCACTGCCTATTT<br>GCAGATCAACAACCTCAAAAATGAGGACACGGCT<br>ACATATTTCTGTTATGTTAACTACGATTATTATACT<br>ATGGACTTCTGGGGTCAAGGAACCTCGGTCACCGT<br>CTCCTCAGGTGAGTGCGGCCGCGAGCCCAGACACT<br>GGACGCTGAACCTCGCGGACAGTTAAGAACCCAG<br>GGGCCTCTGCGCCCTGGGCCCAGCTCTGTCCCACA<br>CCGCGGTCACATGGCACCACCTCTCTTGCAGCCTC<br>CACCAAGGGCCCATCGGTCTTCCCCCTGGCACC<br>CTCCTCCAAGAGCACCTCTGGGGGCACAGCGGC<br>CCTGGGCTGCCTGGTCAAGGACTACTTCCCCGA<br>ACCGGTGACGGTGTCGTGGAACTCAGGCGCCCT<br>GACCAGCGGCGTGCACACCTTCCCGGCTGTCCT<br>ACAGTCCTCAGGACTCTACTCCCTCAGCAGCGT<br>GGTGACCGTGCCCTCCAGCAGCTTGGGCACCCA<br>GACCTACATCTGCAACGTGAATCACAAGCCCAG<br>CAACACCAAGGTGGACAAGAGAGTTGGTGAGAG<br>GCCAGCACAGGGAGGGAGGGTGTCTGCTGGAAGC<br>CAGGCTCAGCGCTCCTGCCTGGACGCATCCCGGCT<br>ATGCAGTCCCAGTCCAGGGCAGCAAGGCAGGCCCC<br>GTCTGCCTCTTCACCCGGAGGCCTCTGCCCGCCCC<br>ACTCATGCTCAGGGAGAGGGTCTTCTGGCTTTTTCC<br>CCAGGCTCTGGGCAGGCACGGGCTAGGTGCCCCTA<br>ACCCAGGCCCTGCACACAAAGGGGCAGGTGCTGG<br>GCTCAGACCTGCCAAGAGCCATATCCGGGAGGACC<br>CTGCCCCTGACCTAAGCCCACCCCAAAGGCCAAAC<br>TCTCCACTCCCTCAGCTCGGACACCTTCTCTCCTCC<br>CAGATTCCAGTAACTCCCAATCTTCTCTCTGCAGA<br>GCCCAAATCTTGTGACAAAACTCACACATGCCC<br>ACCGTGCCCAGGTAAGCCAGCCCAGGCCTCGCCC<br>TCCAGCTCAAGGCGGGACAGGTGCCCTAGAGTAGC<br>CTGCATCCAGGGACAGGCCCCAGCCGGGTGCTGAC<br>ACGTCCACCTCCATCTCTTCCTCAGCACCTGAACT<br>CCTGGGGGGACCGTCAGTCTTCCTCTTCCCCCC<br>AAAACCCAAGGACACCCTCATGATCTCCCGGAC<br>CCCTGAGGTCACATGCGTGGTGGTGGACGTGAG<br>CCACGAAGACCCTGAGGTCAAGTTCAACTGGTA<br>CGTGGACGGCGTGGAGGTGCATAATGCCAAGA<br>CAAAGCCGCGGGAGGAGCAGTACAACAGCACG<br>TACCGTGTGGTCAGCGTCCTCACCGTCCTGCAC<br>CAGGACTGGCTGAATGGCAAGGAGTACAAGTGC<br>AAGGTCTCCAACAAAGCCCTCCCAGCCCCCATC<br>GAGAAAACCATCTCCAAAGCCAAAGGTGGGACC<br>CGTGGGGTGCGAGGGCCACATGGACAGAGGCCGG<br>CTCGGCCCACCCTCTGCCCTGAGAGTGACCGCTGT<br>ACCAACCTCTGTCCCTACAGGGCAGCCCCGAGAA<br>CCACAGGTGTACACCCTGCCCCCATCCCGGGAG<br>GAGATGACCAAGAACCAGGTCAGCCTGACCTGC<br>CTGGTCAAAGGCTTCTATCCCAGCGACATCGCC<br>GTGGAGTGGGAGAGCAATGGGCAGCCGGAGAA | 101 |

TABLE 1-continued

| Seq ID Nos. 3-104 | | | |
|---|---|---|---|
| Name | Chain, Region | Sequence | Seq ID No. |
| | | **CAACTACAAGACCACGCCTCCCGTGCTGGACTC**<br>**CGACGGCTCCTTCTTCCTCTATAGCAAGCTCAC**<br>**CGTGGACAAGAGCAGGTGGCAGCAGGGGAACG**<br>**TCTTCTCATGCTCCGTGATGCATGAGGCTCTGC**<br>**ACAACCACTACACGCAGAAGAGCCTCTCCCTGT**<br>**CTCCGGGTAAA**TGATGA | |
| Chimeric CAN20G2 (FIG. 19A) | H | AATMACPGFLWALVISTCLEFSMAQIQLVQSGPEVK<br>KPGETVKISCKASGYTFTNQGMNWVKQAPGKGLKW<br>MGWINTNTGEPTYTEEFKGRFAFSLETSASTAYLQIN<br>NLKNEDTATYFCYVNYDYYTMDFWGQGTSVTVSSA<br>STKGPSVFPLAPSSKSTSGGTAALGCLVKDYFPEPVT<br>VSWNSGALTSGVHTFPAVLQSSGLYSLSSVVTVPSSS<br>LGTQTYICNVNHKPSNTKVDKRVEPKSCDKTHTCPP<br>CPAPELLGGPSVFLFPPKPKDTLMISRTPEVTCVVVD<br>VSHEDPEVKFNWYVDGVEVHNAKTKPREEQYNSTY<br>RVVSVLTVLHQDWLNGKEYKCKVSNKALPAPIEKTI<br>SKAKGQPREPQVYTLPPSREEMTKNQVSLTCLVKGF<br>YPSDIAVEWESNGQPENNYKTTPPVLDSDGSFFLYSK<br>LTVDKSRWQQGNVFSCSVMHEALHNHYTQKSLSLSP<br>GK | 102 |
| Chimeric CAN20G2 (FIG.19B) | K | GCCGCCACCATGGCATGCCCTGGCTTCCTGTGGGC<br>ACTTGTGATCTCCACCTGTCTTGAATTTTCCATGGC<br>TCAAGTTGTTCTCACCCAGTCTCCAGCAATCATGTC<br>TGCATCTCTAGGGGATCGGGTCACCATGACCTGCA<br>CTGCCAGCTCAAGTGTAATTTCCACTTACTTGCACT<br>GGTATCAGCAGAAGCCAGGcTCtTCCCCCAAACTCT<br>GGATTTATAGCACATCCACCCTGGCTTCTGGAGTC<br>CCACCTCGCTTCAGTGGCAGTGGGTCTGGGACCTC<br>TTACTCTCTCACAATCAGCAGCATGGAGGCTGAAG<br>ATGCTGCCACTTATTACTGCCTCCAGTATCACCGTT<br>CCCCACGGACGTTCGGTGGAGGCACCAAGCTGGAA<br>ATCAAA**C**GTAAGTGCACTTTGCGGCCGCTAGGAAG<br>AAACTCAAAACATCAAGATTTTAAATACGCTTCTT<br>GGTCTCCTTGCTATAATTATCTGGGATAAGCATGCT<br>GTTTTCTGTCTGTCCCTAACATGCCCTGTGATTATC<br>CGCAAACAACACACCCAAGGGCAGAACTTTGTTAC<br>TTAAACACCATCCTGTTTGCTTCTTTCCTCAG**GAAC**<br>**TGTGGCTGCACCATCTGTCTTCATCTTCCCGCC**<br>**ATCTGATGAGCAGTTGAAATCTGGAACTGCCTC**<br>**TGTTGTGTGCCTGCTGAATAACTTCTATCCCAG**<br>**AGAGGCCAAAGTACAGTGGAAGGTGGATAACG**<br>**CCCTCCAATCGGGTAACTCCCAGGAGAGTGTCA**<br>**CAGAGCAGGACAGCAAGGACAGCACCTACAGC**<br>**CTCAGCAGCACCCTGACGCTGAGCAAAGCAGAC**<br>**TACGAGAAACACAAAGTCTACGCCTGCGAAGTC**<br>**ACCCATCAGGGCCTGAGCTCGCCCGTCACAAAG**<br>**AGCTTCAACAGGGGAGAGTGT**TGATAG | 103 |
| Chimeric CAN20G2 (FIG.19B) | K | AATMACPGFLWALVISTCLEFSMAQVVLTQSPAIMS<br>ASLGDRVTMTCTASSSVISTYLHWYQQKPGSSPKLWI<br>YSTSTLASGVPPRFSGSGSGTSYSLTISSMEAEDAATY<br>YCLQYHRSPRTFGGGTKLEIKRTVAAPSVFIFPPSDEQ<br>LKSGTASVVCLLNNFYPREAKVQWKVDNALQSGNS<br>QESVTEQDSKDSTYSLSSTLTLSKADYEKHKVYACE<br>VTHQGLSSPVTKSFNRGEC | 104 |

In Table 1, the CDRs are IMGT numbering. H: heavy chain; K: kappa chain.

In certain embodiments, the antibodies or antigen-binding portions thereof include a variable heavy chain region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to a variable heavy chain region amino acid sequence of the antibody produced by clone CAN20G1 (SEQ ID NO: 12), CAN20G2 (SEQ ID NO: 28), CAN20G5 (SEQ ID NO: 44), or CAN20G8 (SEQ ID NO: 60).

In certain embodiments, the antibodies or antigen-binding portions thereof include a variable light chain region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to a variable light chain region amino acid sequence of the antibody produced by clone CAN20G1 (SEQ ID NO: 4), CAN20G2 (SEQ ID NO: 20), CAN20G5 (SEQ ID NO: 36), or CAN20G8 (SEQ ID NO: 52).

In certain embodiments, the antibodies or antigen-binding portions thereof each include both a variable heavy chain region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to a variable heavy chain region amino acid sequence of the antibody produced by clone CAN20G1 (SEQ ID NO: 12), CAN20G2 (SEQ ID NO: 28), CAN20G5 (SEQ ID NO: 44), or CAN20G8 (SEQ ID NO: 60), and a variable light chain region including an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to a variable light chain amino acid sequence of clone CAN20G1 (SEQ ID NO: 4), CAN20G2 (SEQ ID NO: 20), CAN20G5 (SEQ ID NO: 36), or CAN20G8 (SEQ ID NO: 52).

In various embodiments, the antibodies or antigen-binding portions thereof specifically bind to an epitope that overlaps with, or are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to, an epitope bound by an antibody produced by clone CAN20G1, CAN20G2, CAN20G5, or CAN20G8 and/or compete for binding to toxin A with an antibody produced by clone CAN20G1, CAN20G2, CAN20G5, or CAN20G8.

A variable heavy chain region of the antibodies or antigen-binding portions thereof can comprise one, two three or more complementarity determining regions (CDRs) that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the antibody produced by clone CAN20G1 (SEQ ID NOs: 13, 14, 15), CAN20G2 (SEQ ID NOs: 29, 30, 31), CAN20G5 (SEQ ID NOs: 45, 46, 47), or CAN20G8 (SEQ ID NOs: 61, 62, 63).

A variable light chain region of the antibodies or antigen-binding portions thereof can comprise one, two three or more CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable light chain region of the antibody produced by clone CAN20G1 (SEQ ID NOs: 5, 6, 7), CAN20G2 (SEQ ID NOs: 21, 22, 23), CAN20G5 (SEQ ID NOs: 37, 38, 39), or CAN20G8 (SEQ ID NOs: 53, 54, 55).

A variable heavy chain region of the antibodies or antigen-binding portions thereof can comprise one, two three or more complementarity determining regions (CDRs) that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the antibody produced by clone CAN20G1 (SEQ ID NOs: 13-15), CAN20G2 (SEQ ID NOs: 29-31), CAN20G5 (SEQ ID NOs: 45-47), or CAN20G8 (SEQ ID NOs: 61-63), and a variable light chain region of the antibodies or antigen-binding portions thereof can comprise one, two three or more CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable light chain region of the antibody produced by clone CAN20G1 (SEQ ID NOs: 5-7), CAN20G2 (SEQ ID NOs: 21-23), CAN20G5 (SEQ ID NOs: 37-39), or CAN20G8 (SEQ ID NOs: 53-55).

A variable heavy chain region of the antibodies or antigen-binding portions thereof can include three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable heavy chain region of the antibody produced by clone CAN20G1 (SEQ ID NOs: 13-15), CAN20G2 (SEQ ID NOs: 29-31), CAN20G5 (SEQ ID NOs: 45-47), or CAN20G8 (SEQ ID NOs: 61-63).

In one embodiment, a variable light chain region of the antibodies or antigen-binding portions thereof includes three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable light chain region of the antibody produced by CAN20G1 (SEQ ID NOs: 5-7), CAN20G2 (SEQ ID NOs: 21-23), CAN20G5 (SEQ ID NOs: 37-39), or CAN20G8 (SEQ ID NOs: 53-55).

In one embodiment, a variable heavy chain region of the antibodies or antigen-binding portions thereof includes three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable heavy chain region of the antibody produced by clone CAN20G1 (SEQ ID NOs: 13-15), CAN20G2 (SEQ ID NOs: 29-31), CAN20G5 (SEQ ID NOs: 45-47), or CAN20G8 (SEQ ID NOs: 61-63), and a variable light chain region of the antibodies or antigen-binding portions thereof includes one, two or three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable light chain region of the antibody produced by clone CAN20G1 (SEQ ID NOs: 5-7), CAN20G2 (SEQ ID NOs: 21-23), CAN20G5 (SEQ ID NOs: 37-39), or CAN20G8 (SEQ ID NOs: 53-55).

In certain embodiments, a variable heavy chain region of the antibodies or antigen-binding portions thereof includes three CDRs that are homologous to CDRs of a variable heavy chain region of the antibody produced by clone CAN20G1 (SEQ ID NOs: 13-15), CAN20G2 (SEQ ID NOs: 29-31), CAN20G5 (SEQ ID NOs: 45-47), or CAN20G8 (SEQ ID NOs: 61-63), and a variable light chain region of the antibodies or antigen-binding portions thereof includes three CDRs that are homologous to CDRs of a variable light chain region of the antibody produced by clone CAN20G1 (SEQ ID NOs: 5-7), CAN20G2 (SEQ ID NOs: 21-23), CAN20G5 (SEQ ID NOs: 37-39), or CAN20G8 (SEQ ID NOs: 53-55).

In certain embodiments, CDRs corresponding to the CDRs in Table 1 have sequence variations. For example, CDRs, in which 1, 2 3, 4, 5, 6, 7 or 8 residues, or less than 20%, less than 30%, or less than about 40% of total residues in the CDR, are substituted or deleted can be present in an antibody (or antigen-binding portion thereof) that binds toxin A.

In one embodiment, the antibody or antigen-binding portion thereof contains a variable light chain region and variable heavy chain region homologous to a variable light chain region and variable heavy chain region of the antibody produced by clone CAN20G1 (SEQ ID NO: 4 and SEQ ID NO:12, respectively), CAN20G2 (SEQ ID NO:20 and SEQ ID NO:28, respectively), CAN20G5 (SEQ ID NO:36 and SEQ ID NO:44, respectively), or CAN20G8 (SEQ ID NO:52 and SEQ ID NO:60, respectively).

The antibodies or antigen-binding portions thereof are peptides. The peptides may also include variants, analogs, orthologs, homologs and derivatives of peptides, that exhibit a biological activity, e.g., binding of an antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portions thereof in which specific amino acids have been substituted, deleted or added. These alternations do not have a substantial effect on the peptide's biological properties such as binding activity. For example, antibodies may have amino acid substitutions in the framework region, such as to improve binding to the antigen. In another example, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

The present peptides may be the functionally active variant of antibodies of antigen-binding portions thereof disclosed herein, e.g., with less than about 30%, about 25%, about 20%, about 15%, about 10%, about 5% or about 1% amino acid residues substituted or deleted but retain essentially the same immunological properties including, but not limited to, binding to toxin A.

The invention also encompasses a nucleic acid encoding the present antibody or antigen-binding portion thereof that specifically binds to toxin A of *C. difficile*. The nucleic acid may be expressed in a cell to produce the present antibody or antigen-binding portion thereof. The isolated nucleic acid of the present invention comprises a sequence encoding a peptide at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NOs: 4, 12, 20, 28, 36, 44, 52 or 60.

The isolated nucleic acid may comprise a sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NOs: 68, 69, 70, 71, 72, 73, 74 or 75.

The invention also features expression vectors including a nucleic acid encoding a peptide at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NOs: 4, 12, 20, 28, 36, 44, 52 or 60. The expression vector may include a nucleic acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NOs: 68, 69, 70, 71, 72, 73, 74 or 75.

Nucleic acid molecules encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al., Proc Natl Acad Sci USA, 86:10029-10033 (1989).

Anti-toxin antibodies or portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

The present nucleic acids can be expressed in various suitable cells, including prokaryotic and eukaryotic cells, e.g., bacterial cells, (e.g., *E. coli*), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant. The types of the cells are discussed above.

The present antibody or antigen-binding portion thereof can be expressed in various cells. The types of the cells are discussed above.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

The present invention provides for methods for making an antibody or antigen-binding portion thereof that specifically binds to toxin A of *C. difficile*. For example, a non-human animal is immunized with a composition that includes an inactivated toxin A, and then a specific antibody is isolated from the animal. The method can further include evaluating binding of the antibody to toxin A.

Any of a variety of *Clostridium difficile* toxin proteins, particularly toxin A, may be used in the practice of the present invention. *C. difficile* disease is mediated primarily by toxin A and toxin B. Both toxins are cytotoxic, and lethal when injected intravenously or intraperitoneally into a mouse. Toxin A is also a potent enterotoxin, as demonstrated by the induction of fluid accumulation in the mouse ligated intestinal loop diarrhea model. See, e.g., Babcock, G. J. et al., Infection and Immunity, 74: 6339-6347 (2006) and references contained therein for background.

Table 2 provides amino acid sequences of *Clostridium difficile* toxin A. Variants and fragments of the sequences provided below can also be used as an antigen to generate antibodies.

TABLE 2

| SEQ ID NO | Protein Name | Amino acid Sequence |
|---|---|---|
| 1 | Toxin A | MSLISKEELIKLAYSIRPRENEYKTILTNLDEYNKLTTNNNEN<br>KYLQLKKLNESIDVFMNKYKNSSRNRALSNLKKDILKEVILI<br>KNSNTSPVEKNLHFVWIGGEVSDIALEYIKQWADINAEYNIK<br>LWYDSEAFLVNTLKKAIVESSTTEALQLLEEEIQNPQFDNMK<br>FYKKRMEFIYDRQKRFINYYKSQINKPTVPTIDDIIKSHLVSEY<br>NRDETLLESYRTNSLRKINSNHGIDIRANSLFTEQELLNIYSQE<br>LLNRGNLAAASDIVRLLALKNFGGVYLDVDMLPGIHSDLFK<br>TIPRPSSIGLDRWEMIKLEAIMKYKKYINNYTSENFDKLDQQL<br>KDNFKLIIESKSEKSEIFSKLENLNVSDLEIKIAFALGSVINQAL<br>ISKQGSYLTNLVIEQVKNRYQFLNQHLNPAIESDNNFTDTTKI<br>FHDSLFNSATAENSMFLTKIAPYLQVGFMPEARSTISLSGPGA<br>YASAYYDFINLQENTIEKTLKASDLIEFKFPENNLSQLTEQEIN<br>SLWSFDQASAKYQFEKYVRDYTGGSLSEDNGVDFNKNTAL<br>DKNYLLNNKIPSNNVEEAGSKNYVHYIIQLQGDDISYEATCN<br>LFSKNPKNSIIIQRNMNESAKSYFLSDDGESILELNKYRIPERL<br>KNKEKVKVTFIGHGKDEFNTSEFARLSVDSLSNEISSFLDTIK<br>LDISPKNVEVNLLGCNMFSYDFNVEETYPGKLLLSIMDKITST<br>LPDVNKDSITIGANQYEVRINSEGRKELLAHSGKWINKEEAI<br>MSDLSSKEYIFFDSIDNKLKAKSKNIPGLASISEDIKTLLLDAS<br>VSPDTKFILNNLKLNIESSIGDYIYYEKLEPVKNIIHNSIDDLID<br>EFNLLENVSDELYELKKLNNLDEKYLISFEDISKNNSTYSVRF<br>INKSNGESVYVETEKEIFSKYSEHITKEISTIKNSIITDVNGNLL<br>DNIQLDHTSQVNTLNAAFFIQSLIDYSSNKDVLNDLSTSVKV<br>QLYAQLFSTGLNTIYDSIQLVNLISNAVNDTINVLPTITEGIPIV<br>STILDGINLGAAIKELLDEHDPLLKKELEAKVGVLAINMSLSI<br>AATVASIVGIGAEVTIFLLPIAGISAGIPSLVNNELILHDKATSV<br>VNYFNHLSESKEYGPLKTEDDKILVPIDDLVISEIDFNNNSIKL<br>GTCNILAMEGGSGHTVTGNIDHFFSSPYISSHIPSLSVYSAIGI<br>KTENLDFSKKIMMLPNAPSRVFWWETGAVPGLRSLENNGTK<br>LLDSIRDLYPGKFYWRFYAFFDYAITTLKPVYEDTNTKIKLD<br>KDTRNFIMPTITTDEIRNKLSYSFDGAGGTYSLLLSSYPISMNI<br>NLSKDDLWIFNIDNEVREISIENGTIKKGNLIEDVLSKIDINKN<br>KLIIGNQTIDFSGDIDNKDRYIFLTCELDDKISLIIEINLVAKSY<br>SLLLSGDKNYLISNLSNTIEKINTLGLDSKNIAYNYTDESNNK<br>YFGAISKTSQKSIIHYKKDSKNILEFYNGSTLEFNSKDFIAEDI<br>NVFMKDDINTITGKYYVDNNTDKSIDFSISLVSKNQVKVNGL<br>YLNESVYSSYLDFVKNSDGHHNTSNFMNLFLNNISFWKLFGF<br>ENINFVIDKYFTLVGKTNLGYVEFICDNNKNIDIYFGEWKTSS<br>SKSTIFSGNGRNVVVEPIYNPDTGEDISTSLDFSYEPLYGIDRY<br>INKVLIAPDLYTSLININTNYYSNEYYPEIIVLNPNTFHKKVNI<br>NLDSSSFEYKWSTEGSDFILVRYLEESNKKILQKIRIKGILSNT<br>QSFNKMSIDFKDIKKLSLGYIMSNFKSFNSENELDRDHLGFKI<br>IDNKTYYYDEDSKLVKGLININNSLFYFDPIESNLVTGWQTIN<br>GKKYYFDINTGAASTSYKIINGKHFYFNNNGVMQLGVFKGP<br>DGFEYFAPANTQNNNIEGQAIVYQSKFLTLNGKKYYFDNDS<br>KAVTGWRIINNEKYYFNPNNAIAAVGLQVIDNNKYYFNPDT<br>AIISKGWQTVNGSRYYFDTDTAIAFNGYKTIDGKHFYFDSDC<br>VVKIGVFSGSNGFEYFAPANTYNNNIEGQAIVYQSKFLTLNG<br>KKYYFDNNSKAVTGWQTIDSKKYYFNTNTAEAATGWQTID<br>GKKYYFNTNTAEAATGWQTIDGKKYYFNTNTSIASTGYTIIN<br>GKYFYFNTDGIMQIGVFKVPNGFEYFAPANTHNNNIEGQAIL<br>YQNKFLTLNGKKYYFGSDSKAITGWQTIDGKKYYFNPNNAI<br>AATHLCTINNDKYYFSYDGILQNGYITIERNNFYFDANNESK<br>MVTGVFKGPNGFEYFAPANTHNNNIEGQAIVYQNKFLTLNG<br>KKYYFDNDSKAVTGWQTIDSKKYYFNLNTAVAVTGWQTID<br>GEKYYFNLNTAEAATGWQTIDGKRYYFNTNTYIASTGYTIIN<br>GKHFYFNTDGIMQIGVFKGPDGFEYFAPANTHNNNIEGQAIL<br>YQNKFLTLNGKKYYFGSDSKAVTGLRTIDGKKYYFNTNTAV<br>AVTGWQTINGKKYYFNTNTYIASTGYTIISGKHFYFNTDGIM<br>QIGVFKGPDGFEYFAPANTDANNIEGQAIRYQNRFLYLHDNI<br>YYFGNDSKAATGWATIDGNRYYFEPNTAMGANGYKTIDNK<br>NFYFRNGLPQIGVFKGPNGFEYFAPANTDANNIDGQAIRYQN<br>RFLHLLGKIYYFGNNSKAVTGWQTINSKVYYFMPDTAMAA<br>AGGLFEIDGVIYFFGVDGVKAPGIYG |

Table 3 provides nucleic acid sequences encoding the proteins of Table 2.

TABLE 3

| SEQ ID NO | Accession Number And Gene Name | Nucleotide Sequence |
|---|---|---|
| 2 | Toxin A | atgtctttaa tatctaaaga agagttaata aaactcgcat atagcattag accaagagaa<br>aatgagtata aaactatact aactaattta gacgaatata ataagttaac tacaaacaat<br>aatgaaaata aatatttaca attaaaaaaa ctaaatgaat caattgatgt tttatgaat<br>aaatataaaa attcaagcag aaatagagca ctctctaatc taaaaaaaga tatattaaaa<br>gaagtaattc ttattaaaaa ttccaataca agtcctgtag aaaaaaattt acattttgta<br>tggataggtg gagaagtcag tgatattgct cttgaataca taaaacaatg ggctgatatt<br>aatgcagaat ataatattaa actgtggtat gatagtgaag cattcttagt caatacacta<br>aaaaaggcta tagttgaatc ttctaccact gaagcattac agctactaga ggaagagatt<br>caaaatcctc aatttgataa tatgaaattt tacaaaaaaa ggatggaatt tatatatgat<br>agacaaaaaa ggtttataaa ttattataaa tctcaaatca ataaacctac agtacctaca<br>atagatgata ttataaagtc tcatctagta tctgaatata atagagatga aactttatta<br>gaatcatata gaacaaattc tttgagaaaa ataaatagta atcatgggat agatatcagg<br>gctaatagtt tgtttacaga acaagagtta ttaaatattt atagtcagga gttgttaaat<br>cgtgggaatt tagctgcagc atctgacata gtaagattat tagccctaaa aaattttggc<br>ggagtatatt tagatgttga tatgcttcca ggtattcact ctgatttatt taaaacaata<br>cctagaccta gctctattgg actagaccgt tgggaaatga taaaattaga ggctattatg<br>aagtataaaa aatatataaa taattataca tcagaaaact ttgataaact tgatcaacaa<br>ttaaaagata attttaaact cattatagaa agtaaaagtg aaaaatctga gatattttct<br>aaattagaaa atttaaatgt atctgatctt gaaattaaaa tagctttcgc tttaggcagt<br>gttataaatc aagccttgat atcaaaacaa ggttcatatc ttactaacct agtaatagaa<br>caagtaaaaa atagatatca atttttaaac caacacctta acccagccat agagtctgac<br>aataacttca cagatactac taagattttt catgattcac tatttaattc agctaccgca<br>gaaaactcta tgtttttaac aaaaatagca ccatacttac aagtaggttt tatgccagaa<br>gctcgctcca caataagttt aagtggtcca ggagcttatg catcagctta ctatgatttc<br>ataaatttac aagaaaatac tatagaaaaa actttaaaag catcagattt aatagaattt<br>aaattcccag aaaataatct atctcaattg acagaacaag aaataaatag tctatggagc<br>tttgatcaag caagtgcaaa atatcaattt gagaaatatg taagagatta tactggtgga<br>tctctttctg aagacaatgg ggtagacttt aataaaaata ctgccctcga caaaaactat<br>ttattaaata ataaaattcc atcaaacaat gtagaagaag ctggaagtaa aaattatgtt<br>cattatatca tacagttaca aggagatgat ataagttatg aagcaacatg caatttattt<br>tctaaaaatc ctaaaaatag tattattata caacgaaata tgaatgaaag tgcaaaaagt<br>tactttttaa gtgatgatgg agaatctatt ttagaattaa ataaatatag gatacctgaa<br>agattaaaaa ataaggaaaa agtaaaagta acctttattg gacatggtaa agatgaattc<br>aacacaagcg aatttgctag attaagtgta gattcacttt ccaatgagat aagttcattt<br>ttagatacca taaaattaga tatatcacct aaaaatgtag aagtaaactt gcttggatgt<br>aatatgttta gttatgattt taatgttgaa gaaacttatc ctggtaagtt actattaagt<br>attatggaca aaattacttc cactttacct gatgtaaata aagattctat tactatagga<br>gcaaatcaat atgaagtaag aattaatagt gagggaagaa aagaacttct agctcactca<br>ggtaaatgga taaataaaga ggaagctatt atgagcgatt tatctagtaa agaatacatt<br>tttttgatt ccatagataa taagctaaaa gcaaagtcca agaatattcc aggtttagcg<br>tcaatatcag aagatataaa aacattatta cttgatgcaa gtgttagtcc tgatacaaaa<br>tttattttaa ataatcttaa gcttaatatt gaatcttcta ttggtgatta catttattat<br>gaaaaattag aacctgttaa aaatataatc cacaattcta tagatgattt aatagatgag<br>ttcaatctac ttgaaaatgt atctgatgaa ttatatgaat taaaaaaatt aaataatcta<br>gatgagaagt atttaatatc ttttgaagat atctcaaaaa ataattcaac ttattctgta<br>agatttatta acaaaagtaa tggtgaatca gtttatgtag agacagaaaa agaaattttt<br>tcaaaatata gcgaacatat tacaaaagaa ataagtacta taaagaatag tataattaca<br>gatgttaatg gtaatttatt ggataatata cagttagatc atacttctca agttaataca<br>ttaaacgcag cattctttat tcaatcatta atagattata gtagcaataa agatgtactg<br>aatgatttaa gtacctcagt taaggttcaa ctttatgctc aactatttag tacaggttta<br>aatactatat atgactctat ccaattagta aatttaatat caaatgcagt aaatgatact<br>ataaatgtac tacctacaat aacagagggg atacctattg tatctactat attagacgga<br>ataaacttag gtgcagcaat taaggaatta ctagacgaac atgacccatt actaaaaaaa<br>gaactagaag ctaaggtggg tgttttagca ataaatatgt cattatctat agctgcaacg<br>gtagcttcaa ttgttggaat aggtgctgaa gttactattt tcttattacc tatagctggt<br>atatctgcgg gaataccttc attagttaat aatgaattaa tattgcatga taaggcaact<br>tcagtggtaa actattttaa tcatttgtct gaatctaaag aatatggccc tcttaaaaca<br>gaagatgata aaattttagt tcctattgat gatttagtaa tatcagaaat agattttaat<br>aataattcga taaaactagg aacatgtaat atattagcaa tggagggggg atcaggacac<br>acagtgactg gtaatataga tcactttttc tcatctccat atataagctc tcatattcct<br>tcattatcag tttattctgc aataggtata aaaacagaaa atctagattt ttcaaaaaaa<br>ataatgatgt taccaaatgc tccttcaaga gtgttttggt gggaaactgg agcagttcca<br>ggtttaagat cattggaaaa taatgggact aaattgcttg attcaataag agatttatac<br>ccaggcaaat tttactggag attctatgcc tttttcgatt atgcaataac tacattaaaa<br>ccagtgtatg aagacactaa tactaaaatt aaactagata aagatactag aaactttata<br>atgccaacta taactactga cgaaattaga aacaaattat cttattcatt tgatggagca<br>ggaggaactt actctttatt attatcttca tatccaatat caatgaatat aaatttatct<br>aaagatgatt tatggatatt taatattgat aatgaagtaa gagaaatatc tatagaaaat<br>ggtactatta aaaaaggaaa tttaatagaa gatgttttaa gtaaaattga tataaataaa<br>aataaactta ttataggcaa tcaaacaata gatttttcag gtgatataga taacaaagat<br>agatatatat tcttgacttg tgagttagat gataaaatta gtttaataat agaaataaat<br>cttgttgcaa aatcttatag tttgttattg tctggggata aaaattattt gatatccaat |

TABLE 3-continued

| SEQ ID NO | Accession Number And Gene Name | Nucleotide Sequence |
|---|---|---|
| | | ttatctaata ctattgagaa aatcaatact ttaggcctag atagtaaaaa tatagcttac |
| | | aattacactg atgaatctaa taataaatat tttggagcta tatctaaaac aagtcaaaaa |
| | | agcataatac attataaaaa agacagtaaa aatatattag aattttataa tggcagtaca |
| | | ttagaattta acagtaaaga ctttattgct gaagatataa atgtatttat gaaagatgat |
| | | attaatacta taacaggaaa atactatgtt gataataata ctgataaaag tatagatttc |
| | | tctatttctt tagttagtaa aaatcaagta aaagtaaatg gattatattt aaatgaatcc |
| | | gtatactcat cttaccttga ttttgtgaaa aattcagatg gacaccataa tacttctaat |
| | | tttatgaatt tatttttgaa caatataagt ttctggaaat tgtttgggtt tgaaaatata |
| | | aattttgtaa tcgataaata ctttaccctt gttggtaaaa ctaatcttgg atatgtagaa |
| | | tttatttgtg acaataataa aaatatagat atatattttg gtgaatggaa aacatcgtca |
| | | tctaaaagca ctatatttag cggaaatggt agaaatgttg tagtagagcc tatatataat |
| | | cctgatacgg gtgaagatat atctacttca ctagattttt cctatgaacc tctctatgga |
| | | atagatagat atatcaataa agtattgata gcacctgatt tatatacaag tttaataaat |
| | | attaatacca attattattc aaatgagtac taccctgaga ttatagttct taacccaaat |
| | | acattccaca aaaaagtaaa tataaattta gatagttctt cttttgagta taaatggtct |
| | | acagaaggaa gtgactttat tttagttaga tacttagaag aaagtaataa aaaaatatta |
| | | caaaaaataa gaatcaaagg tatcttatct aatactcaat catttaataa aatgagtata |
| | | gattttaaag atattaaaaa actatcatta ggatatataa tgagtaattt taaatcattt |
| | | aattctgaaa atgaattaga tagagatcat ttaggattta aaataataga taataaaact |
| | | tattactatg atgaagatag taaattagtt aaaggattaa tcaatataaa taattcatta |
| | | ttctattttg atcctataga atctaactta gtaactggat ggcaaactat caatggtaaa |
| | | aaatattatt ttgatataaa tactggagca gcttcaacta gttataaaat tattaatggt |
| | | aaacactttt attttaataa taatggtgtg atgcagttag gagtatttaa aggacctgat |
| | | ggatttgagt attttgcacc tgccaatact cagaataata acatagaagg tcaggctata |
| | | gtttatcaaa gtaaattctt aactttgaat ggcaaaaaat attattttga taatgactca |
| | | aaagcagtca ctggatggag gattattaac aatgagaaat attactttaa tcctaataat |
| | | gctattgctg cagtcggatt gcaagtaatt gacaataata agtattattt caatcctgac |
| | | actgctatca tctcaaaagg ttggcagact gttaatggta gtagatacta ctttgatact |
| | | gataccgcta ttgcctttaa tggttataaa actattgatg gtaaacactt ttattttgat |
| | | agtgattgtg tagtgaaaat aggtgtgttt agtggctcta atggatttga atatttcgca |
| | | cctgctaata cttataataa taacatagaa ggtcaggcta tagtttatca aagtaaattc |
| | | ttaactttga atggtaaaaa atattacttt gataataact caaaagcagt taccggatgg |
| | | caaactattg atagtaaaaa atattacttt aatactaaca ctgctgaagc agctactgga |
| | | tggcaaacta ttgatggtaa aaagtattac tttaatacta acactgctga agcagctact |
| | | ggatggcaaa ctattgatgg taaaaaatat tactttaata ctaacacttc tatagcttca |
| | | actggttata caattattaa tggtaaatat ttttatttta atactgatgg tattatgcag |
| | | ataggagtgt ttaaagtacc taatggattt gaatactttg cacctgctaa tactcataat |
| | | aataacatag aaggtcaagc tatactttac caaaataaat tcttaacttt gaatggtaaa |
| | | aaatattact ttggtagtga ctcaaaagca attactggat ggcaaaccat tgatggtaaa |
| | | aaatattact ttaatcctaa taatgctatt gctgcgactc atctatgcac tataaataac |
| | | gacaagtatt actttagtta tgatggaatt cttcaaaatg gatatattac tattgaaaga |
| | | aataatttct attttgatgc taataatgaa tctaaaatgg taacaggagt atttaaagga |
| | | cctaatggat ttgagtattt tgcacctgct aatactcata ataataacat agaaggtcag |
| | | gctatagttt accagaataa attcttaact ttgaatggca aaaaatatta ttttgataat |
| | | gactcaaaag cagttactgg atggcaaact attgatagta aaaaatatta ctttaatctt |
| | | aacactgctg ttgcagttac tggatggcaa actattgatg gtgaaaaata ttactttaat |
| | | cttaacactg ctgaagcagc tactggatgg caaactattg atggtaaaag atactacttt |
| | | aatactaaca cttatatagc ttcaactggt tatacgatta ttaatggtaa acatttttat |
| | | tttaatactg atggtattat gcagatagga gtgtttaaag gacctgatgg atttgaatac |
| | | tttgcacctg ctaatactca taataataac atagaaggtc aagctatact ttaccaaaat |
| | | aaattcttaa ctttgaatgg taaaaaatat tactttggta gtgactcaaa agcagttacc |
| | | ggattgcgaa ctattgatgg taaaaaatat tactttaata ctaacactgc tgttgcagtt |
| | | actggatggc aaactattaa tggtaaaaaa tactacttta atactaacac ttatatagct |
| | | tcaactggtt atacaattat tagtggtaaa cattttattt ttaatactga tggtattatg |
| | | cagataggag tgtttaaagg acctgatgga tttgaatact ttgcacctgc taatacggat |
| | | gctaacaaca tagaaggtca agctatacgt tatcaaaata gattcctata tttacatgac |
| | | aatatatatt actttggcaa tgattcaaaa gcggctactg gttgggcaac tattgatggt |
| | | aatagatatt acttcgagcc taatacagct atgggtgcga atggttataa aactattgat |
| | | aataaaaatt ttcactttag aaatggttta cctcagatag gagtgtttaa aggacctaat |
| | | ggatttgaat actttgcacc tgctaatacg gatgctaaca atatagatgg tcaagctata |
| | | cgttatcaaa atagattcct acatttactt ggaaaaatat attactttgg taataactca |
| | | aaagcagtta ctggatggca aactattaat agtaaagtat attactttat gcctgatact |
| | | gctatggctg cagctggtgg acttttcgag attgatggtg ttatatattt ctttggtgtt |
| | | gatggagtaa aagcccctgg gatatatggc taa |

In one embodiment, the present invention provides for a method for making a hybridoma that expresses an antibody that specifically binds to toxin A of *C. difficile*. The method contains the following steps: immunizing an animal with a composition that includes inactivated toxin A (e.g., toxoid A); isolating splenocytes from the animal; generating hybridomas from the splenocytes; and selecting a hybridoma that produces an antibody that specifically binds to toxin A. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

Toxins can be inactivated, for example, by treatment with formaldehyde, glutaraldehyde, UDP-dialdehyde, peroxide, oxygen or by mutation (e.g., using recombinant methods).

Relyveld et al., Methods in Enzymology, 93:24, 1983. Woodrow and Levine, eds., New Generation Vaccines, Marcel Dekker, Inc., New York, 1990. Genth et al., Inf. and Immun., 68(3):1094-1101, 2000. Mutant *C. difficile* toxins with reduced toxicity can be produced using recombinant methods. U.S. Pat. Nos. 5,085,862; 5,221,618; 5,244,657; 5,332,583; 5,358,868; and 5,433,945. A full-length or fragment of the toxins or toxoids can be used as immunogens.

In one embodiment, inactivated toxin A is used to immunize mice intraperitoneally or intravenously. One or more boosts may or may not be given. The titers of the antibodies in the plasma can be monitored by, e.g., ELISA (enzyme-linked immunosorbent assay) or flow cytometry. Mice with sufficient titers of anti-toxin A antibodies are used for fusions. Mice may or may not be boosted with antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-toxin monoclonal antibodies. The antibody secreting hybridomas are replated, screened again, and if still positive for anti-toxin monoclonal antibodies, can be subcloned by limiting dilution. For example, the hybridoma clone CAN20G2 of the present invention has been subcloned. One of the subclones is CAN20G2-2-1.

Adjuvants that may be used to increase the immunogenicity of one or more of the *Clostridium difficile* toxin antigens, particularly toxin A include any compound or compounds that act to increase an immune response to peptides or combination of peptides. Non-limiting examples of adjuvants include alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid, QS21 (saponin adjuvant), MPL (Monophosphoryl Lipid A), 3DMPL (3-O-deacylated MPL), extracts from Aquilla, ISCOMS (see, e.g., Sjolander et al. (1998) J. Leukocyte Biol. 64:713; WO90/03184; WO96/11711; WO 00/48630; WO98/36772; WO00/41720; WO06/134423 and WO07/026190), LT/CT mutants, poly (D,L-lactide-co-glycolide) (PLG) microparticles, Quil A, interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The immunized animal can be any animal that is capable of producing recoverable antibodies when administered an immunogen, such as, but not limited to, rabbits, mice, rats, hamsters, goats, horses, monkeys, baboons and humans. In one aspect, the host is transgenic and produces human antibodies, e.g., a mouse expressing the human immunoglobulin gene segments. U.S. Pat. Nos. 8,236,311; 7,625,559 and 5,770,429, the disclosure of each of which is incorporated herein by reference in its entirety. Lonberg et al., Nature 368(6474): 856-859, 1994. Lonberg, N., Handbook of Experimental Pharmacology 113:49-101, 1994. Lonberg, N. and Huszar, D., Intern. Rev. Immunol., 13: 65-93, 1995. Harding, F. and Lonberg, N., Ann. N.Y. Acad. Sci., 764: 536-546, 1995.

After the host is immunized and the antibodies are produced, the antibodies are assayed to confirm that they are specific for the antigen of interest and to determine whether they exhibit any cross reactivity with other antigens. One method of conducting such assays is a sera screen assay as described in U.S. Patent Publication No. 2004/0126829. Anti-toxin antibodies can be characterized for binding to the toxin by a variety of known techniques. For example, in an ELISA, microtiter plates are coated with the toxin or toxoid antigen in PBS, and then blocked with irrelevant proteins such as bovine serum albumin (BSA) diluted in PBS. Dilutions of plasma from toxin-immunized mice are added to each well and incubated. The plates are washed and then incubated with a secondary antibody conjugated to an enzyme (e.g., alkaline phosphatase). After washing, the plates are developed with the enzyme's substrate (e.g., ABTS), and analyzed at a specific OD. In other embodiments, to determine if the selected monoclonal antibodies bind to unique epitopes, the antibody can be biotinylated which can then be detected with a streptavidin labeled probe. Anti-toxin antibodies can be tested for reactivity with the toxin by Western blotting.

Neutralization assays can also be used to measure activity of the anti-toxin antibodies. For example, in vitro neutralization assays can be used to measure the ability of an antibody to inhibit a cytopathic effect on cells in culture (see Examples 7 and 12 below). In one embodiment, the present antibody, or antigen-binding portion thereof, at a concentration ranging from about 1 μM to about 50 μM, from about 2 μM to about 40 μM, from about 3 μM to about 30 μM, from about 4 μM to about 20 μM, from about 4 μM to about 17 μM, from about 5 μM to about 15 μM, or about 10 μM neutralizes greater than about 20%, greater than about 30%, greater than about 40%, greater than about 50%, greater than about 60%, greater than about 70%, greater than about 80%, or greater than about 90% of about 150 ng/ml *C. difficile* toxin A in an in vitro neutralization assay. In vivo assays can be used to measure toxin neutralization as well. In another embodiment, in an in vivo toxin A challenge experiment (e.g., procedures as described in Examples 5, 6, and 7, as well as Babcock et al., Human Monoclonal Antibodies Directed against Toxins A and B prevent *Clostridium difficile*-Induced Mortality in Hamsters. Infection and Immunity (2006) 74(11):6339), when the antibody, or an antigen-binding portion thereof, is administered to a mammal at a dosage ranging from about 1 mg/kg body weight to about 50 mg/kg body weight, from about 2 mg/kg body weight to about 40 mg/kg body weight, from about 3 mg/kg body weight to about 30 mg/kg body weight, from about 5 mg/kg body weight to about 20 mg/kg body weight, from about 8 mg/kg body weight to about 13 mg/kg body weight, or about 10 mg/kg body weight about 24 hours before the mammal is exposed to greater than about 100 ng, or about 100 ng of *C. difficile* toxin A, the chance of survival for the mammal is greater than about 40%, greater than about 50%, greater than about 60%, greater than about 70%, greater than about 80%, or greater than about 90% within about 7 days.

Hybridomas that produce antibodies that bind, preferably with high affinity, to the toxin can than be subcloned and further characterized. One clone from each hybridoma, which retains the reactivity of the parent cells (by ELISA), can then be chosen for making a cell bank, and for antibody purification.

To purify the anti-toxin antibodies, supernatants from the cultured hybridomas can be filtered and concentrated before affinity chromatography with protein A-Sepharose (Pharmacia, Piscataway, N.J.).

Antibodies, or antigen-binding fragments, variants or derivatives thereof of the present disclosure can also be described or specified in terms of their binding affinity to an antigen. The affinity of an antibody for an antigen can be determined experimentally using any suitable method (see, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose *C. difficile* and disease associated with *C. difficile*.

The antibodies or antigen-binding portions thereof can be used on cells in culture, e.g., in vitro or ex vivo. For example, cells can be cultured in vitro in culture medium and contacted by the anti-toxin antibody or fragment thereof. The methods can be performed on cells present in a subject, as part of an in vivo (e.g., therapeutic or prophylactic) protocol. For in vivo embodiments, the contacting step is effected in a subject and includes administering an anti-toxin antibody or portion thereof to the subject under conditions effective to permit binding of the antibody, or portion thereof, to a toxin (e.g., toxin A) expressed by *C. difficile* in the subject, e.g., in the gut.

The antibody or antigen-binding portion thereof can be administered alone or in combination with another therapeutic agent, e.g., a second monoclonal or polyclonal antibody or antigen-binding portion thereof. In one example, the antibody or antigen-binding portion thereof specifically binds to *C. difficile* toxin A is combined with a antibody (monoclonal or polyclonal) or antigen-binding portion thereof specifically binds to *C. difficile* toxin B. In another example, the second agent is an antibiotic, e.g., vancomycin, bacitracin or metronidazole. The antibodies can be used in combination with probiotic agents such as *Saccharomyces boulardii*. The antibodies can also be administered in combinations with a *C. difficile* vaccine, e.g., a toxoid vaccine.

The present invention also provides compositions containing an antibody or antigen-binding portion thereof described herein, and a pharmaceutically acceptable carrier. The composition may contain an isolated nucleic acid encoding the present antibody or antigen-binding portion thereof, and a pharmaceutically acceptable carrier. Pharmaceutically acceptable carriers include any and all solvents, dispersion media, isotonic and absorption delaying agents, and the like that are physiologically compatible. In one embodiment, the composition is effective to reduce, eliminate, or prevent *Clostridium difficile* bacterial infection in a subject.

The invention also features methods of treating *C. difficile* disease in a subject by administering to the subject the present antibody or antigen-binding portion thereof in an amount effective to inhibit *C. difficile* disease. Routes of administration of the present compositions include, but are not limited to, intravenous, intramuscular, subcutaneous, oral, topical, subcutaneous, intradermal, transdermal, subdermal, parenteral, rectal, spinal, or epidermal administration.

The compositions of the present invention can be prepared as injectables, either as liquid solutions or suspensions, or as solid forms which are suitable for solution or suspension in liquid vehicles prior to injection. The composition can also be prepared in solid form, emulsified or the active ingredient encapsulated in liposome vehicles or other particulate carriers used for sustained delivery. For example, the composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the vaccine.

The present antibodies or antigen-binding portions thereof are formulated into compositions for delivery to a mammalian subject. The composition is administered alone, and/or mixed with a pharmaceutically acceptable vehicle or excipient. Suitable vehicles are, for example, water, saline, dextrose, glycerol, ethanol, or the like, and combinations thereof. In addition, the vehicle can contain minor amounts of auxiliary substances such as wetting or emulsifying agents, pH buffering agents, or adjuvants. The compositions of the present invention can also include ancillary substances, such as pharmacological agents, cytokines, or other biological response modifiers.

Furthermore, the compositions can be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Actual methods of preparing such dosage forms are known, or will be apparent, to those skilled in the art. See, e.g., Remington's Pharmaceutical Sciences, Mack Publishing Company, Easton, Pa., 21st edition.

Compositions can be administered in a single dose treatment or in multiple dose treatments on a schedule and over a time period appropriate to the age, weight and condition of the subject, the particular composition used, and the route of administration.

In one embodiment, a single dose of the composition according to the invention is administered. In other embodiments, multiple doses are administered. The frequency of administration can vary depending on any of a variety of factors, e.g., severity of the symptoms, degree of immunoprotection desired, whether the composition is used for prophylactic or curative purposes, etc. For example, in one embodiment, the composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a polypeptide according to the invention, e.g., the period of time over which the composition is administered, can vary, depending on any of a variety of factors, e.g., subject response, etc. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's").

In one aspect, a solution of the composition are dissolved in a pharmaceutically acceptable carrier, e.g., an aqueous carrier if the composition is water-soluble. Examples of aqueous solutions include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate.

Solid formulations can be used in the present invention. They can be formulated as, e.g., pills, tablets, powders or capsules. For solid compositions, conventional solid carriers can be used which include, e.g., mannitol, lactose, starch, magnesium stearate, sodium saccharin, talcum, cellulose, glucose, sucrose, magnesium carbonate, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

When administered orally, the present compositions may be protected from digestion. This can be accomplished either by complexing the antibody or antigen-binding portion thereof with a composition to render it resistant to acidic and enzymatic hydrolysis or by packaging the antibody or antigen-binding portion thereof in an appropriately resistant carrier such as a liposome. Means of protecting compounds from digestion are well known in the art. Fix, Pharm Res. 13: 1760-1764, 1996. Samanen, J. Pharm. Pharmacol. 48: 119-135, 1996. U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. Sayani, Crit. Rev. Ther. Drug Carrier Syst. 13: 85-184, 1996. For topical, transdermal administration, the agents are formulated into ointments, creams, salves, powders and gels. Transdermal delivery systems can also include, e.g., patches.

The present compositions can also be administered in sustained delivery or sustained release mechanisms. For example, biodegradeable microspheres or capsules or other biodegradeable polymer configurations capable of sustained delivery of a peptide can be included in the formulations of the invention (see, e.g., Putney, Nat. Biotechnol. 16: 153-157, 1998).

For inhalation, the present compositions can be delivered using any system known in the art, including dry powder aerosols, liquids delivery systems, air jet nebulizers, propellant systems, and the like. Patton, Biotechniques 16: 141-143, 1998. Also can be used in the present invention are product and inhalation delivery systems for polypeptide macromolecules by, e.g., Dura Pharmaceuticals (San Diego, Calif.), Aradigrn (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

Compositions or nucleic acids, polypeptides, or antibodies of the invention can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa). For a "regional effect," e.g., to focus on a specific organ, one mode of administration includes intra-arterial or intrathecal (IT) injections, e.g., to focus on a specific organ, e.g., brain and CNS (see e.g., Gurun, Anesth Analg. 85: 317-323, 1997). For example, intra-carotid artery injection can be used where it is desired to deliver a nucleic acid, peptide or polypeptide of the invention directly to the brain. Actual methods for preparing parenterally administrable compositions will be known or apparent to those skilled in the art and are described in detail. Bai, J. Neuroimmunol. 80: 65-75, 1997. Warren, J. Neurol. Sci. 152: 31-38, 1997. Tonegawa, J. Exp. Med. 186: 507-515, 1997.

In one aspect, the pharmaceutical formulations comprising compositions or nucleic acids, polypeptides, or antibodies of the invention are incorporated in lipid monolayers or bilayers, e.g., liposomes. U.S. Pat. Nos. 6,110,490; 6,096,716; 5,283,185 and 5,279,833. Aspects of the invention also provide formulations in which water soluble nucleic acids, peptides or polypeptides of the invention have been attached to the surface of the monolayer or bilayer. For example, peptides can be attached to hydrazide-PEG-(distearoylphosphatidyl) ethanolamine-containing liposomes (see, e.g., Zalipsky, Bioconjug. Chem. 6: 705-708, 1995). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla, J. Pharm. Sci. 85: 5-8, 1996), transmucosally, or orally. The invention also provides pharmaceutical preparations in which the nucleic acid, peptides and/or polypeptides of the invention are incorporated within micelles and/or liposomes (see, e.g., Suntres, J. Pharm. Pharmacol. 46: 23-28, 1994; Woodle, Pharm. Res. 9: 260-265, 1992). Liposomes and liposomal formulations can be prepared according to standard methods and are also well known in the art. Akimaru, Cytokines Mol. Ther. 1: 197-210, 1995. Alving, Immunol. Rev. 145: 5-31, 1995. Szoka, Ann. Rev. Biophys. Bioeng. 9: 467, 1980. U.S. Pat. Nos. 4,235,871; 4,501,728 and 4,837,028.

In one aspect, the compositions are prepared with carriers that will protect the peptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. In one embodiment, the dosage of such compounds lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

An exemplary, non-limiting range for a therapeutically or prophylactically effective amount of an antibody or antigen-binding portion of the invention is from about 0.001 to about 60 mg/kg body weight, about 0.01 to about 30 mg/kg body weight, about 0.01 to about 25 mg/kg body weight, about 0.5 to about 25 mg/kg body weight, about 0.1 to about 20 mg/kg body weight, about 10 to about 20 mg/kg body weight, about 0.75 to about 10 mg/kg body weight, about 1 to about 10 mg/kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight.

The composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging from about 0.01 mg to about 10 g, from about 0.1 mg to about 9 g, from about 1 mg to about 8 g, from about 1 mg to about 7 g, from about 5 mg to about 6 g, from about 10 mg to about 5 g, from about 20 mg to about 1 g, from about 50 mg to about 800 mg, from about 100 mg to about 500 mg, from about 0.01 mg to about 10 g, from about 0.05 μg to about 1.5 mg, from about 10 μg to about 1 mg protein, from about 30 μg to about 500 μg, from about 40 pg to about 300 pg, from about 0.1 μg to about 200 mg, from about 0.1 μg to about 5 from about 5 μg to about 10 μg, from about 10 μg to about 25 μg, from about 25 μg to about 50 μg, from about 50 μg to about 100 μg, from about 100 μg to about 500 from about 500 μg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

In therapeutic applications, the present compositions are administered to a subject at risk for *Clostridium difficile* bacterial infection or suffering from active infection in an amount sufficient to at least partially arrest or prevent the condition or a disease and/or its complications.

An anti-toxin antibody (e.g., monoclonal antibody) can also be used to isolate toxins by standard techniques, such as affinity chromatography or immunoprecipitation. Moreover, an anti-toxin antibody can be used to detect the toxin, e.g., to screen samples (e.g., in a stool sample) for the presence of *C. difficile*. Anti-toxin antibodies can be used diagnostically to monitor levels of the toxin in tissue as part of a clinical testing procedure, e.g., to, for example, determine the efficacy of a given treatment regimen.

The invention also provides kits containing an anti-toxin antibody or antigen-binding portion thereof. Additional components of the kits may include one or more of the following: instructions for use; other reagents, a therapeutic agent, or an agent useful for coupling an antibody to a label or therapeutic agent, or other materials for preparing the antibody for administration; pharmaceutically acceptable carriers; and devices or other materials for administration to a subject.

Various combinations of antibodies can be packaged together. For example, a kit can include antibodies that bind to toxin A and antibodies that bind to toxin B (e.g., monoclonal anti-toxin B antibodies, or polyclonal antisera reactive with toxin B). The antibodies can be mixed together, or packaged separately within the kit.

Instructions for use can include instructions for therapeutic application including suggested dosages and/or modes of administration, e.g., in a patient with a symptom of CDAD. Other instructions can include instructions on coupling of the antibody to a label or a therapeutic agent, or for purification of a conjugated antibody, e.g., from unreacted conjugation components.

The kit may or may not contain at least one nucleic acid encoding anti-toxin antibodies or fragment thereof, and instructions for expression of the nucleic acids. Other possible components of the kit include expression vectors and cells.

The present antibodies, antigen-binding portions thereof, compositions and methods can be used in all vertebrates, e.g., mammals and non-mammals, including human, mice, rats, guinea pigs, hamsters, dogs, cats, cows, horses, goats, sheep, pigs, monkeys, apes, gorillas, chimpanzees, rabbits, ducks, geese, chickens, amphibians, reptiles and other animals.

The following examples of specific aspects for carrying out the present invention are offered for illustrative purposes only, and are not intended to limit the scope of the present invention in any way.

EXAMPLES

Example 1: Hybridoma Fusion

A classical hybridoma fusion was performed. Mice receive their first immunization with toxoid A using Complete Freund's Adjuvant (CFA) and two subsequent boosters on days 28 and 48 with toxoid A and Incomplete Freund's Adjuvant (IFA). A trial bleed was performed at day 55 and the serum was tested to check for titres of anti-toxoid A antibody. If IgG titres were high enough fusions were performed. If not, mice received two more boosts with IFA and a second trial bleed was taken. Fusions were performed using 2 mice at a time. Mice were given a final push intraperitoneally (i.p.) with toxoid A in PBS three days prior to the fusion.

On the day of the fusion, mice are sacrificed and their spleens removed. Splenocytes are washed from the spleen using a syringe and needle and collected in a 50 ml tube for fusion with myeloma cells. Myelomas are an immortal tumor cell line used as fusion partners, grown in the presence of 8-azaguanine, a toxic nucleotide analog which blocks the salvage pathway. Cells grown in the presence of 8-aza survive only by incurring defective mutations in the hypoxanthine-guanine phosphoribosyl transferase (HGPRT) gene. B cells are fused with the myeloma cells using Polyethylene Glycol (PEG) 1500. Fused cells are mixed into semi-solid agarose with drug selection and plated out into petri dishes. HAT media containing Hypoxanthine, Aminopterin, and Thymidine is used for drug selection. Aminopterin is a drug which inhibits the de novo pathway for nucleotide metabolism which is absolutely required for survival/cell growth in myeloma lines defective in HGPRT, and allows selection usually within 24-48 hours.

Example 2: Hybridoma Screening

The next step is screening of the growing hybridomas. A commercial semisolid agarose within which the cells grow as "balls" of cells in the 3-D matrix was used. This facilitates the picking of these balls by hand (by visual inspection) and transferring these clonal balls into a 96 well plate containing suitable media. The cells were allowed to grow for 3-7 days and then the supernatant removed for screening and replaced with fresh media. Positive binding in ELISA (or other tests) resulted in continuing to grow the hybridomas by transferring them up into larger tissue culture vessels with increasing volume. The mAbs were isotyped using a suitable commercial isotyping kit for murine mAbs using the spent supernatant. The decision to move a clone to the next stage of selection is based on its reactivity to native toxin A using an ELISA and its survival, usually based upon serial dilutions and reactivity of at least ⅛ or 1/16 or higher, as well as IgG class; therefore the number of clones decreased throughout the selection procedure. The mAbs that underwent further characterization were: CAN20G2, CAN20G1, CAN20G5 & CAN20G8 and CAN19G1, CAN19G2, CAN19G3.

Example 3: ELISA Assay of Mouse Monoclonal Antibodies

An ELISA was used to test the binding of the toxA mAbs against whole toxin A and recombinant toxin A fragment 4 as well as to determine if they were cross-reactive to whole toxin B and toxin B fragment 4. The mAb clones were compared to CDA1 (Merck anti-toxin A mAb used as a control). The ELISA plate was coated with 100 μg/ml of Toxin fragment 4 and 400 μg/ml of whole Toxin so that the coatings were equimolar. The wells were blocked with 1% skim milk then probed with serially diluted CAN19 or CAN20 mAbs (0.1 μg/ml to 1 μg/ml) and binding was detected with a commercial goat anti-mouse IgG-HRP antibody. Negative and positive controls were also run. The chimeric human mAb 13C6 is specific to Ebolavirus GP and served as the negative control for human the Fc of CDA-1. The CDA-1 mAb and the polyclonal toxoid A antibody (pAb) served as positive controls, however, the CDA-1 mAb is human and the polyclonal is rabbit, thus, they both used a different secondary antibody making direct comparisons between them and the murine mAbs impossible. The secondary antibody control is for the murine secondary antibody. The plate was read at 405 nm after 60 min incubation with substrate. The titration data for each antibody is shown in FIG. 1.

Figure 2:
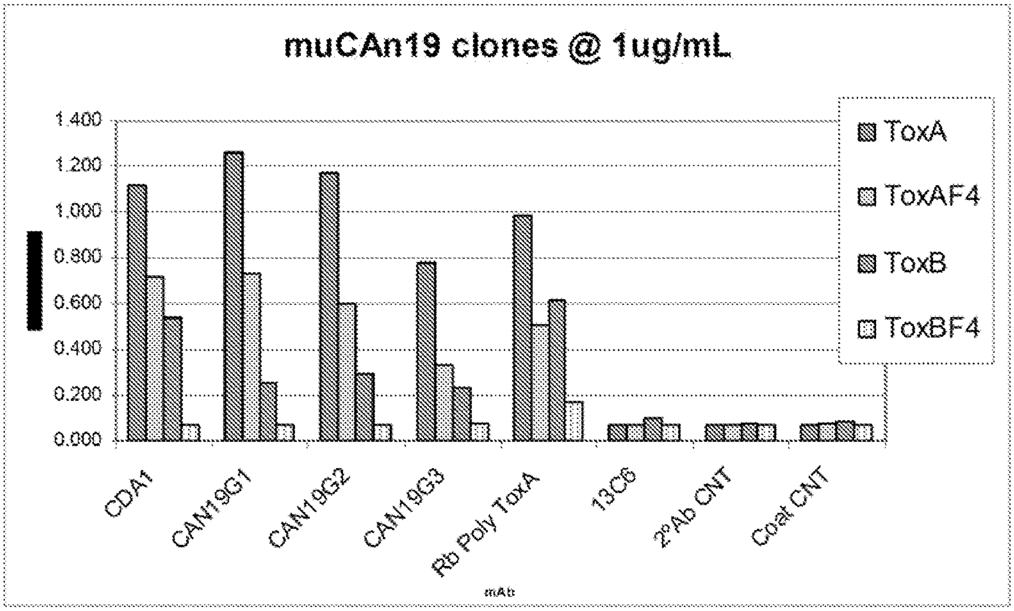
FIG. 2 is an ELISA showing the binding activity of purified 1 μg/ml CAN19 mAbs on toxin A (ToxA) and toxin A fragment 4 (ToxAF4). ToxB is toxin B; ToxBF4 is toxin B fragment 4.
Figure 3:
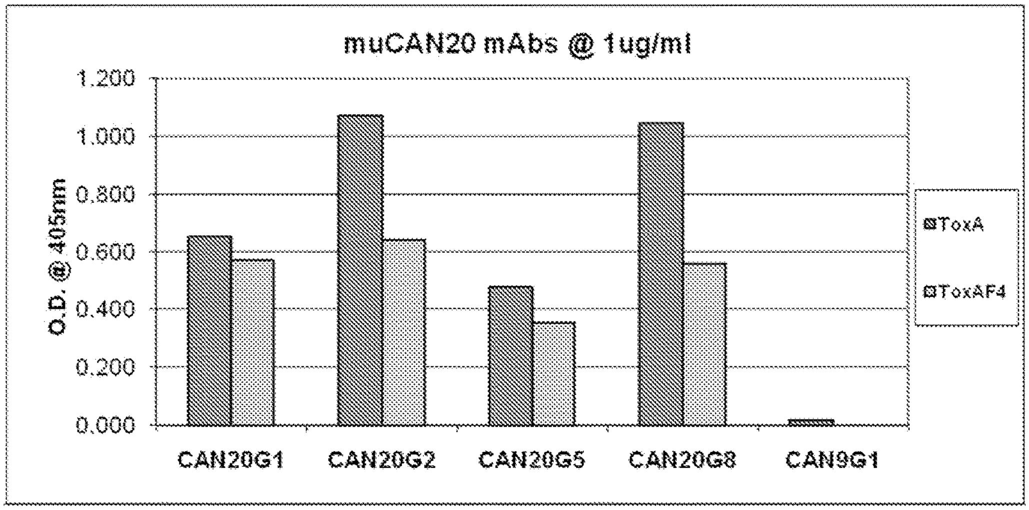
FIG. 3 is an ELISA assay showing the binding activity of purified 1 μg/ml murine CAN20 mAbs on toxin A and toxin A fragment 4.

Results:

As shown in FIGS. 2 and 3, CAN19G1 and CAN19G2 mAbs bind to whole toxin A and toxin A fragment 4 at a similar level to CDA1. The CAN19 mAbs showed little cross-reactivity to toxin B. CAN20 mAbs bind to toxin A. CAN20G2 and CAN20G5 bind to toxin A fragment 4 at a similar level to CDA1. None of CAN20 mAbs showed cross-reactivity to toxin B.

Example 4: Western Blot of Mouse Monoclonal Antibodies

A 4-12% SDS-PAGE gel was run for 1.5 hours at 200 volts with a combination of *C. difficile* proteins; whole toxin A, toxoid A (commercial), recombinant toxin fragment 4 and toxin B (whole, toxoid and fragment 4). The gel was then transferred to a nitrocellulose membrane for 45 min at 45 volts. The membrane was blocked overnight at 4° C. with 1% skim milk in 1×TBST and the next day washed with 1×TBST to remove the skim milk. The mAbs (1° Ab) were diluted in 1×TBST at a concentration of 1 μg/ml and used to probe the membrane containing the transferred products for 2 hours at room temperature (RT) on a shaker. The membranes were then washed with 1×TBST to remove unbound 1° Ab and probed with anti-mouse IgG-HRP (2° Ab) at a dilution of 1:4000 for 1 hour at RT on a shaker.

Figure 5:
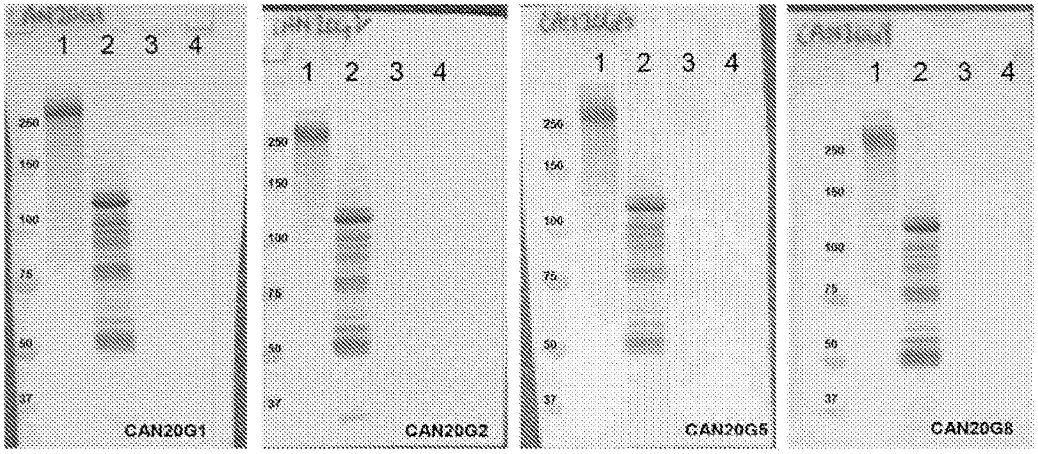
FIG. 5 shows a Western blot of Purified CAN20 clones (1 μg/ml). Blot A was probed with CAN20G1, blot B was probed with CAN20G2, blot C was probed with CAN20G5, and blot D was probed with Can20G8. (Lane 1: Toxin A (308 kDa); Lane 2: Toxin A Fragment 4 (114 kDa); Lane3: Toxin B (280 kDa); Lane4: tetanus toxoid).

Results:

As shown in FIGS. 4 and 5, all three CAN19 mAbs showed binding to whole toxin A, toxoid A and toxin A fragment 4. They all showed only weak or no cross-reactivity to toxin B or to the negative control. CAN20G1, CAN20G2, CAN20G5 and CAN20G8 mAbs all showed strong binding to whole toxin A and toxin A fragment 4. There was no cross-reactivity to toxin B or to the negative control.

Example 5: Affinity Analysis of Mouse Monoclonal Antibodies

Biolayer interferometry was used to measure the interactions between whole Toxin A and the anti-toxin A antibodies. The Octet QKe instrument (ForteBio) was equipped with Streptavidin (SA) biosensors. 40 μg/ml of biotinylated whole Toxin A was coupled to SA sensors and the toxin A mAbs, in a dilution series from 100 nM to 1.56 nM, were reacted on the toxin-coated pins for 10 minutes followed by a dissociation step in PBS for another 10 minutes. The results were then analyzed using ForteBio Data Analysis software to determine the dissociation constant ($K_D$), which is the measure used to describe the binding strength between antibody and antigen, $k_{on}$(1/Ms), the on-rate at which antibody antigen complexes form, and $k_{dis}$(1/s), the off-rate at which the antibody antigen complexes dissociate. The samples were run over two separate days. Table 4 shows affinity data for purified CAN20G versions, as well as CDA1.

TABLE 4

Affinity data for purified CAN20G versions and CDA1

| ID Name | $K_D$ (M) | $k_{on}$(1/Ms) | $k_{dis}$ (1/s) |
|---|---|---|---|
| CAN20G1 | 1.79E−09 | 1.23E+05 | 2.19E−04 |
| CAN20G2 | 4.19E−12 | 1.04E+05 | 4.35E−07 |
| CAN20G5 | 2.01E−09 | 8.38E+04 | 1.68E−04 |
| CAN20G8 | 1.65E−09 | 1.31E+05 | 2.16E−04 |
| CDA1 | 6.24E−10 | 4.80E+05 | 2.91E−04 |

Example 6: Epitope Binning of Mouse Monoclonal Antibodies

The Octet QKe is a label free real-time biosensor that uses disposable fiber-optic sensors that detect biomolecular interactions via biolayer interferometry. The epitope binning assay was performed against the previously characterized CDA1 anti-toxin A mAb to examine whether the present toxin A mAbs share a similar or a different epitope with CDA-1. Secondly, the assay was used to confirm shared single or potentially multiple epitope bins between the toxin A mAbs. The classical sandwich method was used and involves coupling the mAb to sensor, binding antigen, and then binding to another mAb. The second mAb can bind the captured Ag only if its epitope does not overlap that of the immobilized mAb.

Figure 6A:
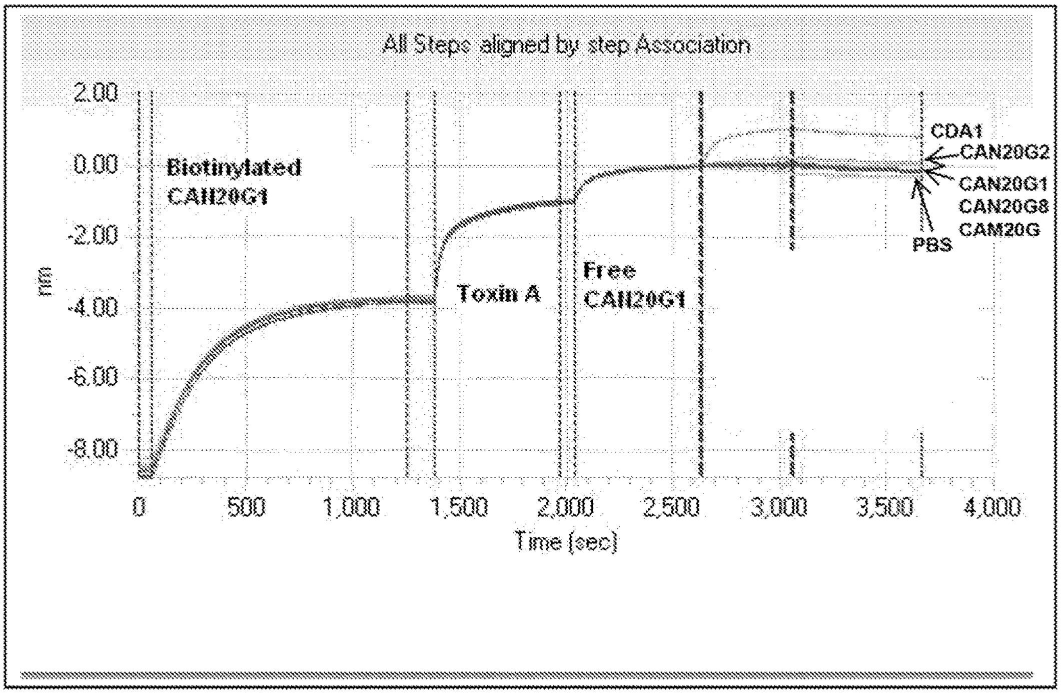
Figure 6B:
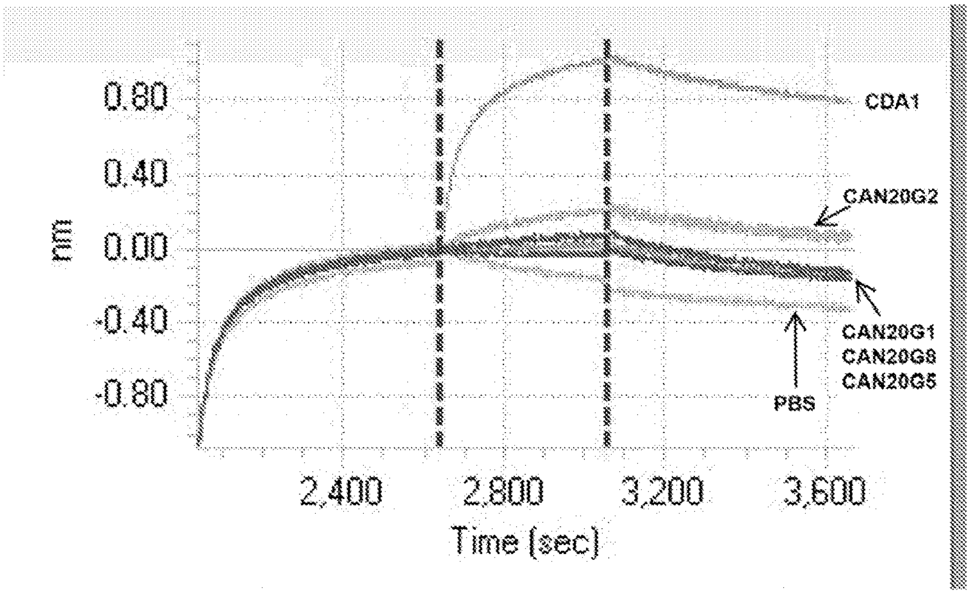

Results:

The strong nM shift in wavelength above the CAN20G1 and PBS control (a vertical increase in the binding curve) indicates more binding is able to occur and that the test antibody is binding to an exposed and distinct epitope. As shown in FIGS. 6*a* and 6*b*, the results indicate that there is an elevated shift in wavelength for the CDA1 antibody. This indicates that the CDA1 and CAN20 mAbs bind to distinct epitopes. All the CAN20 mAbs share the same epitope. There is a slight nm elevation for the CAN20G2 indicating a slight increase in binding which could be due to a somatic mutation between the known VH and VL chains of CAN20G1 and CAN20G2, different antibody epitopes or both.

Example 7: In Vitro Neutralization of Mouse Monoclonal Antibodies

The in vitro neutralization assays described herein were performed using VERO (green monkey) cells and Toxin A purchased from List Biological Laboratories. (BIAD report: *Clostridium difficile* Toxin A Monoclonal Antibody Characterization). The protocols used for xCelligence (Roche Diagnostics) and Bioassy methods are summarized below.

Cell Attachment Phase—xCelligence Method.

(1) Trypsinized cells in source flask. (2) Added 2 mL of trypsin to flask and washed cells to remove traces of media then aspirate. (3) Added 3 mL of trypsin and incubated at 37° C. for approximately 10 minutes until cells were detached. (4) Added 6 mL of assay media or growth media to flask. (4) Centrifuged at 1300 rpm for 8 minutes. (5) Aspirated supernatant and resuspended cells with 6 mL of Assay media or growth media. (6) Counted cells and calculated required cell density. (For Vero cells, $1\times10^5$ cells/mL and for T84 cells, $8\times10^5$ cells/mL.) (7) To a 96 well E-plate added 100 μL of Assay media to wells A1 thru H10 and 100 μL of T84 media to wells A11 thru H12. (8) Performed background reading on xCelligence. (9) Removed 50 μL of Assay media from wells A1-H10. (10) Added 50 μL of $1.0\times10^5$ cells/mL suspension to these wells for a final $5.0\times10^4$ cells/mL seeding density. (11) Added 100 μL of T84 $8\times10^5$ cells/mL cell suspension to A11 and A12. (12) Serially diluted 2-fold down through H11 and H12. (13) Remove 100 μL from H11 and H12. (14) Added 100 μL of T84 media to A11-H12 for a final volume 200 μL. (15) Incubated plate at room temperature for 20-30 minutes to allow cells to settle evenly. (16) Placed plate in 37° C. incubator with 5% CO2 overlay for 20-24 hours.

Cell Attachment Phase—Bioassy Method.

(1) Trypsinized cells in source flasks. (2) Pooled cells from source flasks. (3) Centrifuged cells at 1270 RPM for 8 minutes. (4) Removed supernatant and resuspended cells in assay medium. (5) Six mL of medium should be used for every flask pooled. (6) Counted cells to determine cell viability and quantity of cells required to plate at $1.0\times10^5$ cells/mL. (7) Final concentration will be $0.5\times10^5$ cells/mL when plated. (8) Added 50 μL of 10% Assay Media to wells B2-G11 of a 96 well black clear-bottom microplate. (9) Overlayed 50 μL of cells to wells B2-G11 of a 96 well flat-bottom microplate at $1.0\times10^5$ cells/mL. (10) To the outer edge wells, added 100 μL of warmed assay media. (11) Mixed on a plate shaker for a homogeneous suspension. (12) Left plate at room temperature for 20-30 minutes to allow cells to settle evenly across the wells. (13) Placed cell plates in a 37° C., 5% $CO_2$ humidified incubator for 20-24 hours.

Toxin a Preparation:

(1) Prepared Toxin A primary stock (20 μg/mL) by adding 100 μL of sterile LW to one vial (2.0 μg) of Toxin A. (2) Diluted primary stock as shown in Table 5.

TABLE 5

| TcdA Concentration (ng/mL) | Final Plating Concentration (ng/mL) | Volume of TcdA Primary Stock (20 μg/mL) | Volume of 10% Assay Medium |
|---|---|---|---|
| 60 | 20 | 12 μL | 3988 μL |

Sample Preparation:

To test potency, all the monoclonal antibodies were at a starting concentration of 30 μg/mL. Samples were prepared as shown in Table 6.

TABLE 6

| Sample (Stock concentration) | Preparation Concentration | Final Plating Concentration | Volume Sample Stock | Volume Assay Medium |
|---|---|---|---|---|
| CDA (1.556 mg/mL) | 30 μg/mL | 10 μg/mL | 28.9 μL | 1471.1 μL |
| CAN19 G1 Purified 30 μg/mL | 30 μg/mL | 10 μg/mL | 150 μL/plate | n/a |
| CAN19 G2 Purified 30 μg/mL | 30 μg/mL | 10 μg/mL | 150 μL/plate | n/a |
| CAN19 G3 Purified 30 μg/mL | 30 μg/mL | 10 μg/mL | 150 μL/plate | n/a |

Dilution Plate Preparation—xCelligence:

(1) Added assay media and 150 μL of sample to wells as shown below in Table 7. (2) Serially diluted each sample 2-fold down the column by taking 75 μL from Row A and adding to Row B, mixed 3 to five times and repeated down through to Row G. (3) Added appropriate controls to wells as shown in Table 5. (4) Overlayed sample wells with 75 μL of Toxin A. Shake on a plate shaker until homogeneous. (5) Incubated at 37° C. for 1 hour.

TABLE 7

| xCelligence Dilution Plate Layout Cell Density: 0.5e5 cells/mL | | | | | | | | | | | | |
|---|---|---|---|---|---|---|---|---|---|---|---|---|
| | CDA 1 | CDA 2 | G1 3 | G1 4 | G2 5 | G2 6 | G3 7 | G3 8 | G1 Sup 9 | G1 Sup 10 | G2 Sup 11 | G2 Sup 12 |
| A | Sample | Sample | Sample | Sample | Sample | Sample | CDA Ctl | CDA Ctl | Sample | Sample | 150 uL | 150 uL |
| B | 75 uL | 75 uL | 75 uL | 75 uL | 75 uL | 75 uL | 75 uL | 75 uL | 75 uL | 75 uL | 150 uL | 150 uL |
| C | 75 uL | 75 uL | 75 uL | 75 uL | 75 uL | 75 uL | 75 uL | 75 uL | 75 uL | 75 uL | 150 uL | 150 uL |
| D | 75 uL | 75 uL | 75 uL | 75 uL | 75 uL | 75 uL | 75 uL | 75 uL | 75 uL | 75 uL | 150 uL | 150 uL |
| E | 75 uL | 75 uL | 75 uL | 75 uL | 75 uL | 75 uL | 75 uL | 75 uL | 75 uL | 75 uL | 150 uL | 150 uL |
| F | 75 uL | 75 uL | 75 uL | 75 uL | 75 uL | 75 uL | 75 uL | 75 uL | 75 uL | 75 uL | 150 uL | 150 uL |
| G | 75 uL | 75 uL | 75 uL | 75 uL | 75 uL | 75 uL | 75 uL | 75 uL | Cell Ctl | Cell Ctl | Tox Ctl | Tox Ctl |
| H | CDA Ctl | CDA Ctl | G1 Ctl | G1 Ctl | G2 Ctl | G2 Ctl | G3 Ctl | G3 Ctl | G1 Sup Ctl | G1 Sup Ctl | G2 Sup Ctl | G2 Sup Ctl |

Cell control = 150 μL AM
Toxin control = 75 μL toxin + 75 μL AM
mAb control = 75 μL mAb + 75 μL AM
75 uL/150 uL = volume AM
Sample = 150 uL respective sample plate #1, add CDA, CAN19G1 (purified), and CAN19G1 supernatant. On plate #2 added CDA, CAN19G2 purified, and CAN19G2 supernatant. On plate #3 added CDA, CAN19G3 purified, and CAN19G3 supernatant. (2) Transferred 75 μL from column 2 to column 3. Mixed with multichannel. Repeated procedure through to column 9. (3) Remove 75 μL from column 10 leaving a final volume 100 μL. (4) Added controls (75 μL) to appropriate wells along with 75 μL of AM. (5) Overlayed sample wells with 75 μL of Toxin A.

Bioassy Method:

Added assay medium to wells as shown in Table 8. (1) Add 150 μL of sample to appropriate wells of column 2. On

TABLE 8

| Bioasssay Dilution Plate Layout Cell Density: 0.5e5 cells/mL | | | | | | |
|---|---|---|---|---|---|---|
| | | | 50 μL Serial Dilutions | | | |
| | 1 | 2 | 3 | 4 | 5 | 6 |
| A | 200 μL AM | 200 μL AM | 200 μL AM | 200 μL AM | 200 μL AM | 200 μL AM |
| B | 200 μL AM | CDA | 75 μL AM | 75 μL AM | 75 μL AM | 75 μL AM |
| C | 200 μL AM | CNJ mAb | 75 μL AM | 75 μL AM | 75 μL AM | 75 μL AM |
| D | 200 μL AM | CNJ sup | 75 μL AM | 75 μL AM | 75 μL AM | 75 μL AM |
| E | 200 μL AM | CDA | 75 μL AM | 75 μL AM | 75 μL AM | 75 μL AM |
| F | 200 μL AM | CNJ mAb | 75 μL AM | 75 μL AM | 75 μL AM | 75 μL AM |
| G | 200 μL AM | CNJ sup | 75 μL AM | 75 μL AM | 75 μL AM | 75 μL AM |
| H | 200 μL AM | 200 μL AM | 200 μL AM | 200 μL AM | 200 μL AM | 200 μL AM |

Cell control = 150 μL AM
Toxin control = 75 μL toxin + 75 μL AM
mAb control = 75 μL mAb + 75 μL AM TABLE 8-continued Bioasssay Dilution Plate Layout
Cell Density: 0.5e5 cells/mL

| | 50 μL Serial Dilutions | | | | Controls | |
|---|---|---|---|---|---|---|
| | 7 | 8 | 9 | 10 | 11 | 12 |
| A | 200 μL AM | 200 μL AM | 200 μL AM | 200 μL AM | 200 μL AM | 200 μL AM |
| B | 75 μL AM | 75 μL AM | 75 μL AM | CDA ctl | Cell | 200 μL AM |
| C | 75 μL AM | 75 μL AM | 75 μL AM | mAb Ctl | Toxin | 200 μL AM |
| D | 75 μL AM | 75 μL AM | 75 μL AM | sub Ctl | Cell | 200 μL AM |
| E | 75 μL AM | 75 μL AM | 75 μL AM | CDA ctl | Toxin | 200 μL AM |
| F | 75 μL AM | 75 μL AM | 75 μL AM | mAb Ctl | mAb | 200 μL AM |
| G | 75 μL AM | 75 μL AM | 75 μL AM | sub Ctl | pAb | 200 μL AM |
| H | 200 μL AM | 200 μL AM | 200 μL AM | 200 μL AM | 200 μL AM | 200 μL AM |

Sample Addition to Cell Plates:

(1) Following 1 hour incubation, cell plates were removed from incubator. (2) Removed 50 μL of cell suspension carefully with multichannel pipette being sure not to disturb cell monolayer. (3) Transferred 100 μL of samples from dilution plate to appropriate wells of cell plate. (4) Mixed on plate shaker for a homogeneous solution. Incubated 72 hours at 37° C. with a 5% CO2 overlay.

Data Analysis:

The xCelligence system captures data in real-time. For the purposes of comparison to the conventional bioassay methods, the final read time data is analyzed. For this, we normalized the cell index at the time point before toxin/antibody addition to the plate, using the appropriate toxin wells as baseline. This will create a baseline normalized cell index on the Y axis versus log concentration of antibody. We analyzed the data to determine potency of CAN19 mAbs in comparison to CDA. % Neutralization is calculated as follows with xCelligence:

% Neutralization=(Sample *CI* index/Antibody Control *CI* index)*100%

Neutralization is calculated as follows with Bioassay fluorescence:

% Neutralization=(Mean Sample *RFU*/Mean Toxin *RFU*)/(Mean Cell *RFU*/Mean Toxin *RFU*)*100

The procedures of this Example were also performed on CAN20 mAbs.

Results:

CAN19 mAbs were less neutralizing than CDA1. CAN20G2 is the most potent mAb in vitro and is more potent than CDA1. CAN20G3, G5 and G8 are also neutralizing.

Table 9 summarizes the $IC_{50}$ data generated for each CAN19 mAb demonstrating that the CAN19 clones are less neutralizing compared to CDA1.

TABLE 9

| Sample | IC50 | |
|---|---|---|
| CDA | 0.347 ug/mL | standard |
| 1 | 2.31 ug/mL | CAN19G1 |
| 2 | 2.17 ug/mL | CAN19G2 |
| 3 | 2.44 ug/mL | CAN19G3 |

Table 10 summarizes the $EC_{50}$ data generated for each CAN20 mAb demonstrating that CAN20G2, CAN20G3, CAN20G5, and CAN20G8 are the most neutralizing of the clones.

TABLE 10

| ID Name | Calculated anti-TcdA IgG Concentration By Biacore(μg/mL) | EC50 Value (μg/mL)[1] |
|---|---|---|
| CAN20G1 | 188.0 | 0.17 |
| CAN20G2 | 142.2 | 0.0101 |
| CAN20G3 | 5.9 | 0.076 |
| CAN20G4 | 22.8 | 0.147 |
| CAN20G5 | 87.5 | 0.13 |
| CAN20G6 | 314.2 | 0.151 |
| CAN20G7 | 134.9 | 0.158 |
| CAN20G8 | 272.4 | 0.137 |

[1]The EC50 value is the concentration of antibody which neutralizes 50% of the TcdA toxin dose.

Example 8: Mouse In Vivo Toxin Challenge

The mouse in vivo toxin challenge test was based on previous publications (Babcock et al., Human Monoclonal Antibodies Directed against Toxins A and B prevent *Clostridium difficile*-Induced Mortality in Hamsters. Infection and Immunity (2006) 74(11):6339). Swiss webster mice weighing 20-30 g were given 250 μg of mAb or controls at day 0 and allowed to rest. After 24 hrs (day 1), the mice were given a lethal dose of TcdA (100 ng). This dose kills 90-100% of animals by 24 hours in an unprotected state. The mice were observed for 7 days (days 1-7) for signs of abnormality and local and systemic disease. The mice were euthanized on Day 7. All observations were recorded and the % survival was determined for each treatment group.

Results:

As shown in FIGS. 7, 8, and 9, the study results indicate that the CAN19 and CAN20 mAbs protect mice against toxin A. There was >90% survival with CAN19G1, G2 and G3. All three CAN19 mAbs showed efficacy. All the CAN20 mAbs were efficacious. CAN20G1, G2, G5 and G8 showed 100% protection at a dose of 0.25 mg/mouse. CAN20G2 showed 100% protection at 0.125 mg/mouse. The experiment was repeated to confirm the efficacy of CAN20G2. The results confirmed the previous study. CAN20G2 showed 100% protection at the full does of 0.25 mg/mouse and 90% protection at the half dose 0.125 mg/mouse.

Example 9: muCAN20G2 V Gene Sequencing

RNA was isolated from the CAN20G2 parental hybridoma clonal cell line using the RNeasy Mini Kit. The amplification of V genes from the RNA was performed using the Qiagen OneStep RT-PCR Kit. Several combinations of primer sets were used as follows: for immunoglobulin variable region gene sequence confirmation from the hybridomas, a set of Variable region gene (V-gene) subgroup-specific oligonucleotide primers are used. These include 5'mVK-Lead-1, 3'KappaConstRT, 5'mVH-Lead-2, 5'mVH-Lead-2A, and 3'mIG1-2C RT. In order to rule out potential contamination from the known and endogenous aberrant kappa light chain V-gene mRNA (found within P3X63 myelomas) (Yuan, X. et al., J. Immunol. Methods, 294: 199-207 (2004)), the RT-PCR was also performed using non-subgroup specific primer sets, 5'mVK-Lead-1A, 5'mVK-Lead-1A, 5'mVK-Lead-3, 5'mVK-Lead-3A, 5'mVH-IGHV1-Lead, 5'mVH-Lead-1, 5'mVH-Lead-3, 5'mVH-Lead-4, and 5'mVH-Lead-5. Refer to FIG. 10 for a list of the primers and their sequences. The results of the PCR amplification reactions were determined by examining the PCR products on an analytical agarose gel, and the visualized bands at approximately 500 bp were gel isolated for cloning. The extracted DNA was directly TA cloned into the pCR2.1-TOPO vector using the low melt agarose method in the TOPO TA Cloning manual. Five colonies of each CAN20G clone reaction were sequenced in both directions using the M13 Forward and M13 Reverse primers. Sequence data was analyzed using DNAStar Lasergene software. The resulting rearranged V-gene sequences were compared to IMGT/V-Quest reference directory sets and to the NCBI immunoglobulin blast search (FIG. 11).

Example 10: Humanization of muCAN20G2

Three humanized IgG/k versions of CAN20G2 mAb have been created as well as a chimeric IgG1/k. For the humanized versions, maximum identity alignment with human germline alleles was used (from the IMGT and NCBI websites) to help to identify acceptor frameworks. All 6 CDRs were inserted. Other residues were changed or maintained due to surface exposure or involvement in folding or interchain contacts, respectively. The CDRs of the murine mAb sequence (CAN20G2) match very well with the germline CDRs of the closest human alleles. This resembles the "superhumanization" approach where CDR matching rather than total framework is used in a variation of the use of germline sequences as acceptor frameworks. In the case of Tan et al., J. Immunol. 2002, 169:1119-1125, the authors used the CDR sequences and tried to match the so called canonical classes of CDRs based upon the Chothia classification system. However, because particular CDRs are germline encoded and particular canonical conformations tend to be found in certain frameworks, the "Superhumanization" method of choosing acceptor frameworks does not in all cases result in the selection of a different candidate acceptor framework. It is empirical and remains to be tested for multiple mAb specificities. This is in part because the straight-up alignment of frameworks for identity inherently encompasses the CDRs as well in the comparison. Table 11 shows the percent humanness, at the amino acid level, of each of the humanized constructs of CAN20G2.

TABLE 11

| CONSTRUCT | PERCENT "HUMAN" |
|---|---|
| MURINE CAN20G2 | 66% |
| CHIMERIC CAN20G2 | 90% |
| HE-CAN20G2 | 91% |
| hCDR-CAN20G2 | 97% |
| AVA-CAN20G2 | 95% |

FIG. 12 shows the alignment of muCAN20G2 v-regions with the closest human germline v-region. The human germlines were used as acceptor frameworks for humanization.

CDR-huCAN20G2—CDR Grafted Only.

The best matching germline allele for both $V_H$ and Vk were used as an acceptor framework for grafting the CDRs. No other changes were made to the acceptor frameworks. FIGS. 13*a* and 13*b* show the design of the CDR-huCAN20G2 design we used. The closest matching human frameworks are IGHV7-4-1*02 and IGKV1-39*01. The CDRs (IMGT Numbering) of the muCAN20G2 were inserted into the human framework. The heavy CDR3 contained a HpaI restriction site that was altered for cloning into pcDNA3002Neo. A 5' Kozak and HAVT20 leader sequence was added for correct translation and trafficking.

HE-huCAN20G2 "Human Engineered"

This humanized version was generated using a strategy most similar to the "human engineering" strategy used by Studnicka et al (1994) used to humanize a murine mAb to CD5. Essentially, the closest human germline allele for both CAN20G2 $V_H$ and Vk were identified, individually, and designed for use as acceptor frameworks. The CAN20G2 $V_H$ has a 76% identity with the human IgVH7-4-1*02 allele. The CDRs were grafted or altered to match the CAN20G2 mAb sequences. The HE-hCAN20G2 antibodies are shown in FIGS. 14, 15, and 16. Some residues were modified or maintained as described in the legend. In this case, crystal structural inference was taken from Avastin/Bevacizumab. Avastin is a humanized monoclonal antibody that recognizes and blocks vascular endothelial growth factor A (VEGF-A) and is marketed for the treatment of advanced colorectal cancer. Avastin turns out to have highest identity with the same human germline gene as CAN20G2 VH and the crystal structure of its variable region structure has been determined.

AVA-huCAN20G2 "Avastinized"—

Alignment of the translation of the Avastin $V_H$ and Vκ/Jκ alleles with the respective humanized CAN20G2 $V_H$ and Vκ immunoglobulin variable regions is shown in FIG. 17. Many mAbs have been humanized capitalizing on the natural sequence pairing of $V_H$ and $V_L$ found in other mAbs with crystal structural data. In this case, we used the same $V_H$ as in Version 1-HE (which has high identity with Avastin $V_H$), and we used the Avastin Vk as the Light chain acceptor framework. This allowed us to exploit the known interchain contacts and modification in our design (FIG. 18).

Chimeric-huCAN20G2 Chimeric Version:

A chimeric CAN20G2 was designed as a control. Certain residues outside the CDRs are involved in the structure of the hypervariable regions. During the humanization process some of the residues may be altered. Because sequence variation within the canonical structures will modulate the conformation of the paratope, it is essential to determine whether the loss/gain in affinity/function/neutralization is due to the humanization process or the human Fc region. The CAN20G2 murine v-regions were designed onto human IgG1 and human Kappa constant regions. The construct contains Kozak, HAVT20 Leader and double stop sequences (FIGS. 19A and 19B).

Example 11: SDS Page and Western Blot Analyses of Humanized Antibodies

A large scale transfection (300 ml) was performed in HEK293F cells to obtain a large quantity of each huCAN20G2 mAb. A total of $3\times10^8$ cells were transfected with 300 μg of huCAN20G2 plasmid DNA. The supernatant was harvested by centrifugation (3000 rpm, 15 min, RT) 3 days and 7 days post-transfection. The transfected supernatant was filtered through a 0.22 μm filter. The filtered sup was purified on a Protein G column (HiTRAP HP, GE Healthcare) using the AktaPurifier FPLC. The eluted protein was buffer exchanged into D-PBS and the concentration determined by BCA assay. A range of 30-45 mg was purified from the 300 ml cultures. The purified protein was run on an SDS-page to confirm its size (FIG. 22). The purified mAb was also used to probe a membrane with whole toxin A and toxin A fragment 4 to confirm the binding characteristics of the mAbs (FIG. 23).

Example 12: In Vitro Neutralization Assay of Humanized Antibodies

An in vitro neutralization assay for *C. difficile* Toxins using CT-26 cells was performed to test the neutralization capability of the humanized mAb clones against *C. difficile* toxin A. The CT-26 cells were seeded in a 96 well plate at a concentration of 2.5-3×$10^4$ cells/100 ul/well and the plate was incubated in a $CO_2$ incubator for 4-5 hrs at 37° C. Two blank wells containing only media (no cells) were also included in the plate.

The toxin and toxin/Ab mixtures were prepared in tubes and diluted to the desired concentrations using RPMI media. The tubes were left to incubate at room temperature for 1 hour. The media was removed from the wells of the plate and each of the tubes, containing either media alone, toxin alone, or toxin/Ab mixtures, was transferred to its designated well. The plates were left to incubate for 48 hours at 37° C. and 5% $CO_2$. The WST-1 detection reagent was added to each well (10 μl of reagent/100 μl volume in the well) and incubated for 1 hour at 37° C. and 5% $CO_2$. The plate was shaken for 1 min and then read at 450 nm.

Cell Viability was Determined Based on the Cell Controls as Below:

$$\% \text{ Cell viability}=\text{Mean } OD \text{ of test/Mean } OD \text{ of cell control}\times 100.$$

Toxin neutralization is calculated by the formula as below:

$$\% \text{ Neutralization}=(\text{Sample } OD-\text{Toxin control } OD)/(\text{Cell control } OD-\text{toxin control } OD)*100$$

Results:

As shown in FIGS. 20*a* and 20*b*, the chimeric CAN20G2 and the HE-CAN20G2 are the most neutralizing at all mAb concentrations. The HE-CAN20G2 is more neutralizing at most mAb concentrations at either Toxin A concentration. The Medarex CDA IgG and the hCDR mAbs show similar modest neutralization ability and the AVA-CAN20G2 shows very little neutralization ability.

Example 13: Affinity Assay of Humanized Antibodies

Biolayer interferometry was used to measure the interactions between whole Toxin A and the humanized CAN20G2 antibodies. The Octet QKe instrument was equipped with Streptavidin (SA) biosensors. 40 μg/ml of biotinylated whole Toxin A was coupled to SA sensors and the humanized versions, in a dilution series from 100 nM to 1.56 nM, was allowed to associate with the toxin for 10 minutes followed by a dissociation step in PBS for another 10 minutes. The results were then analyzed using ForteBio Data Analysis software to determine $K_D$ (nM), the measure used to describe the binding strength between antibody and antigen, $k_{on}$(1/Ms), the rate at which antibody antigen complexes form, and $k_{dis}$(1/s), the rate at which the antibody antigen complexes dissociate.

Results:

The results from two experiments were averaged and show that the muCAN20G2 and the chCAN20G2 are within threefold indicating no loss in affinity (Table 10). In contrast, the AVA-CAN20G2 showed almost a full log loss in affinity. The CDR-huCAN20G2 showed loss in affinity nearing that of the AVA humanized version. The binding affinity of the HE-huCAN20G2 version is slightly higher than all the other humanized versions but within the acceptable threefold range showing little or no loss of affinity compared to the chimeric CAN20G2. We believe this is the optimal comparator because we cannot predict the effects of exchanging the human constant regions for the murine IgG2a constant regions and this comparison takes this into account. The three fold range comparison is considered by the ForteBio experts as insignificant variation.

TABLE 12

Affinity data for purified human CAN20G2 versions.

| | $K_D$ (M) | $k_{on}$ (1/Ms) | $k_{dis}$ (1/s) |
|---|---|---|---|
| muCAN20G2-2-1 | 1.66E−10 | 1.08E+05 | 1.80E−05 |
| chCAN20G2 | 1.72E−10 | 1.14E+05 | 1.93E−05 |
| AVA-CAN20G2 | 1.33E−09 | 5.45E+04 | 9.02E−05 |
| HE-huCAN20G2 | 3.32E−10 | 9.39E+04 | 3.14E−05 |
| CDR-huCAN20G2 | 8.00E−10 | 6.76E+04 | 5.41E−05 |

Example 14: ELISA Testing of Humanized Antibodies

A medium scale (150 ml) transfection was performed in HEK293F cells to test for expression of the huCAN20G2 mAb. A total of 1.5×$10^8$ cells were transfected with 150 μg of DNA. The supernatant was harvested by centrifugation (3000 rpm, 15 min, RT) 3 days and 7 days post-transfection. The transfected supernatant was filtered through a 0.22 μm filter. The filtered supernatant from the medium scale transfection was screened with an ELISA prior to purification. An ELISA was run to test the binding of the human mAb clones against whole toxin A and toxin A fragment 4. The human mAb clones were compared to CDA1 and the chimeric CAN20G2. The ELISA plate was coated with 100 μg/ml of Toxin A fragment 4 and 400 μg/ml of whole Toxin A so that the coats were equimolar. The coats were probed with serially diluted mAb (0.128 ng/ml to 10 μg/ml) and binding was detected with anti-human IgG-HRP antibody. The plate was read at 405 nm after 60 min incubation with substrate.

Results:

As shown in FIGS. 21 *a-d*, all three humanized versions of mAb CAN20G2, in addition to the chimeric version, bind to whole toxin A with similar intensity in ELISA. In contrast, there are clearly differences in the binding of the humanized mAbs to recombinant toxin A fragment 4, which is the domain of Tcd A to which the parental CAN20G2 is known to map and bind. This may be indicative of the functionality if this binding to fragment 4 correlates with in vitro and in vivo protection and may allow the development of domain 4 assays as a surrogate for CAN20G2 efficacy. The chimeric and HE mAbs appear to bind similarly whereas the CDR mAb binds to a lesser degree and the AVA mAb does not appear to bind to the toxin A fragment 4.

Example 15: In Vivo Challenge with Tcd A

Based on the in vitro data, the CDR and HE humanized versions of CAN20G2 were tested in vivo and compared to the chimeric version in the mouse lethal toxin challenge model (as noted in Example 8 above). Swiss Webster mice weighing 20-30 g were given 250 ug of mAb or controls at day 0 and allowed to rest. After 24 hours, the mice were administered a lethal dose of TcdA (100 ng). This dose kills 100% of animals by 24 hours in an unprotected state. The mice were observed for a period of 4 days for clinical symptoms, abnormality and local and systemic disease. All observations were recorded and the results summarized in Table 13 which shows all the antibodies tested, including the HE and CDR versions are effective at neutralizing toxin A and protecting against toxin A challenge in vivo.

TABLE 13

Effect of Can20G2 humanized MAbs against Tcd A challenge in mice.

| Groups | Treatment | N | # Survivors | # Dead/euthanized during the study |
|---|---|---|---|---|
| A | chimeric-Can20G2 | 5 | 5 | 0 |
| B | HE-Can20G2 | 5 | 5 | 0 |
| C | hCDR-Can20G2 | 5 | 5 | 0 |
| D | muCan20G2 | 5 | 5 | 0 |
| E | CDA1-1 | 5 | 5 | 0 |
| F | Rb-polyclonal | 5 | 5 | 0 |
| G | TcdA/PBS controls | 5 | 0 | 5 |
| H | PBS alone | 4 | 4 | 0 |

Example 16: Immunogenicity Analysis of Humanized Antibodies

In order to determine their immunogenicity, CDR-huCAN20G2 and HE-huCAN20G2 were tested in the EpiScreen™ (Antitope Ltd) time course T cell assays, using two markers (proliferation and IL-2 production) to measure T cell activation. Specifically, peripheral blood mononuclear cells (PBMCs) were prepared from a cohort of 21 healthy donors with representing HLA (Human Leukocyte Antigen) allotypes. Bulk cultures were established using $CD8^+$-depleted PBMCs. $CD4^+$ T cell proliferation by incorporation of [$^3$H]-Thymidine was measured at various time points after the addition of the antibodies. IL-2 secretion was also measured using ELISpot assays in parallel to the proliferation analysis.

Methods

Preparation and Selection of Donor PBMCs

Peripheral blood mononuclear cells (PBMCs) were isolated from healthy community donor buffy coats (from blood drawn within 24 hours). PBMCs were isolated from buffy coats by Lymphoprep (Axis-shield, Dundee, UK) density centrifugation and $CD8^+$ T cells were depleted using $CD8^+$ RosetteSep™ (StemCell Technologies Inc, London, UK). Donors were characterized by identifying HLA-DR haplotypes using an HLA SSP-PCR based tissue-typing kit (Biotest, Solihull, UK). T cell responses to a control antigen (Keyhole Limpet Haemocyanin (KLH), [Pierce (Perbio), Cramlington, UK]), as well as peptides derived from Influenza A and Epstein Barr viruses were also determined. PBMCs were then frozen and stored in liquid nitrogen until required.

Preparation of Antibodies

The two test antibodies were diluted in AIM-V® culture medium (Invitrogen, Paisley, UK) just before use and the final assay concentration was 0.3 mM. KLH was used as a reproducibility control and stored at −20° C. as a 10 mg/ml stock solution in water. For the studies, an aliquot of KLH was thawed before immediately diluting to 400 μm/ml in AIM-V® (final concentration 100 μm/ml). Phytohaemagglutanin (PHA, Sigma, Poole, UK) was used as a positive control in the ELISpot and a 1 mg/ml stock was stored at −20° C. before diluting to a final concentration of 2.5 μm/ml in cell cultures.

Assessment of Cell Viability

On day 7, bulk cultures (previously established for the proliferation assay) were gently resuspended and 10 ml of each sample was removed from all donors and mixed with 10 ml trypan blue. These samples were then assessed for viability using trypan blue dye exclusion with a Countess® Automated Cell Counter instrument (Invitrogen).

EpiScreen™ Time Course T Cell Proliferation Assays

PBMCs from each donor were thawed, counted and viability assessed. Cells were revived in room temperature AIM-V® culture medium, washed and resuspended in AIM-V® to 4-6×$10^6$ PBMC/ml. For each donor, bulk cultures were established in which 1 ml proliferation cell stock was added to the appropriate wells of a 24 well plate. 0.5 ml of culture medium and 0.5 ml of each diluted antibody were added to the PBMC to give a final concentration of 0.304. For each donor, a reproducibility control (cells incubated with 100 μg/ml KLH), a positive control (cells incubated with 2.5 μg/ml PHA) and a culture medium-only well were also included. Cultures were incubated for a total of 8 days at 37° C. with 5% $CO_2$. On days 5, 6, 7 and 8, the cells in each well were gently resuspended and 3×100 μl aliquots transferred to each well of a round bottomed 96 well plate. The cultures were pulsed with 0.75 μCi [$^3$H]-Thymidine (Perkin ElmerR, Beaconsfield, UK) in 100 μl AIM-VR culture medium and incubated for a further 18 hours before harvesting onto filter mats (Perkin ElmerR) using a Skatron Micro 96S-10056 cell harvester. Counts per minute (cpm) for each well were determined by Meltilex™ (Perkin ElmerR) scintillation counting on a 1450 Microbeta Wallac Trilux Liquid Scintillation Counter (Perkin ElmerR) in paralux, low background counting.

EpiScreen™ IL-2 ELISpot Assays

Homologous donors to those used in the proliferation assay were also used for the IL-2 ELISpot assay. Cells were thawed and revived as described above. ELISpot plates (Millipore, Watford, UK) were pre-wetted and coated overnight with 100 μl/well IL-2 capture antibody (R&D Systems, Abingdon, UK) in PBS. Plates were then washed 3 times in PBS, incubated overnight in blocking buffer (1% BSA in PBS) and washed in AIM-V® medium. The cell density for each donor was adjusted to 4-6×$10^6$ PBMC/ml in AIM-V® culture medium and 100 μl of cells were added to each well. 50 μl of samples and controls were added to the appropriate wells as well as 50 ml of AIMV to bring the total volume to 200 ml/well. Antibodies were tested in sextuplicate cultures and, for each donor, a negative control (AIM-V® medium alone), no cells control and a mitogen positive control (PHA at 2.5 μg/ml—used as an internal test for ELISpot function and cell viability), were also included on each plate. After an 8 day incubation period, ELISpot plates were developed by sequential washing in $dH_2O$ and PBS (×3) prior to the addition of 100 μl filtered, biotinylated detection antibody (R&D Systems) in PBS/1% BSA. Following incubation at 37° C. for 1.5 hours, plates were further washed in PBS (×3) and 100 μl filtered streptavidin-AP (R&D Systems) in PBS/1% BSA was added for 1.5 hours (incubation at room temperature). Streptavidin-AP was discarded and plates were washed in PBS (×4). 100 μl BCIP/NBT substrate (R&D Systems) was added to each well and incubated for 30 minutes at room temperature. Spot development was stopped by washing the wells and the backs of the wells three times with $dH_2O$. Dried plates were scanned on an Immunoscan® Analyser and spots per well (spw) were determined using Immunoscan® Version 4 software.

EpiScreen™ Data Analysis

For proliferation and IL-2 ELISpot assays, an empirical threshold of a stimulation index (SI) equal to or greater than 2 (SI≥2.00) has been previously established, whereby samples inducing responses above this threshold are deemed positive (borderline SIs≥1.90 are also highlighted). Extensive assay development and previous studies have shown that this is the minimum signal-to-noise threshold allowing maximum sensitivity without detecting large numbers of false positive responses or omitting subtle immunogenic events. For both proliferation (n=3) and IL-2 ELISpot data (n=6) sets, positive responses were defined by statistical and empirical thresholds as follows:

1. Significance (p<0.05) of the response by comparing cpm or spw of test wells against medium control wells using unpaired two sample student's t-test.
2. Stimulation index greater than or equal to 2 (SI≥2.00), where SI=mean of test wells (cpm or spw)/baseline (cpm or spw). Data presented in this way is indicated as SI≥2.00, p<0.05.

In addition, intra-assay variation was assessed by calculating the coefficient of variance and standard deviation (SD) of the raw data from replicate cultures.

Results & Discussion

While there is generally a good correlation between IL-2 production and proliferation after T cells have been activated, proliferation and IL-2 ELISpot assays have been interpreted independently. Inter-assay variability was assessed using KLH as a reproducibility control where the frequency of positive T cell responses against KLH were compared in two separate EpiScreen™ assays. The results show that interassay variability for KLH-specific T cell responses is within the acceptable range and consistent with previous studies (≤10%).

Assessment of Cell Viability

An initial assessment of any gross effect of the antibodies and the buffer on PBMC viability was performed for 10 donors used in the EpiScreen™ time course assays. Cell viabilities were calculated using trypan blue dye exclusion of PBMC 7 days after culture with the antibodies. It was clear that the two test antibodies and buffer formulation did not significantly affect the viability of the cells because PBMC from medium alone cultures had a mean viability similar to that of the samples and KLH treated cells (between 93-97%).

EpiScreen™ Time Course Proliferation Assay

FIG. 24 and Table 12 show the results obtained in the EpiScreen™ time course T cell proliferation assay of CD4+ T cell responses induced by the antibodies. Both test antibodies induced positive proliferation responses with SI≥2.00 (p<0.05) in one or more donors in the proliferation assay. Borderline responses SI≥1.90 (p<0.05) are also highlighted. Positive proliferation responses ranged between 5% and 24% of the donor cohort (Table 14).

TABLE 14

Summary of T cell proliferation and IL-2 ELISpot responses

| Donor | CDR-hu CAN20G2 | HE-hu CAN20G2 | Buffer | KLH |
|---|---|---|---|---|
| Donor 1 | | | | PE |
| Donor 2 | | | | PE |
| Donor 3 | PE | PE | | PE |
| Donor 4 | PE* | | | PE |
| Donor 5 | | | | PE |
| Donor 6 | | | | PE |
| Donor 7 | PE‡ | | | E |
| Donor 8 | | | | PE |
| Donor 9 | | | | PE |
| Donor 10 | | | | PE |
| Donor 11 | | | N/A | PE |
| Donor 12 | | | N/A | PE |
| Donor 13 | | | N/A | PE |
| Donor 14 | PE | | N/A | E |
| Donor 15 | | | N/A | PE |
| Donor 16 | PE | | N/A | E |
| Donor 17 | | | N/A | PE |
| Donor 18 | | | N/A | P |
| Donor 19 | | | N/A | PE |
| Donor 20 | | | N/A | PE |
| Donor 21 | | | N/A | PE |
| Proliferation % | 24 | 5 | 0 | 86 |
| ELISpot % | 24 | 5 | 0 | 95 |
| Proliferation and ELISpot % | 24 | 5 | 0 | 81 |
| Correlation % | 100 | 100 | N/A | 94 |

In Table 14, during the entire time course (days 5-8), positive T cell proliferation responses (SI≥2.00, significant p<0.05) were indicated as "P", and positive T cell IL-2 ELISpot responses (SI≥2.00, significant p<0.05) were indicated as "E". Borderline responses (significant p<0.05 with SI≥1.90) was shown as (*). No data was obtained on day 8 of the proliferation assay for donor 7 (‡). Formulation buffer was tested on donors 1-10 only donor 11-21 were not tested with the buffer (grey boxes). N/A indicated no data is available.

Antibody CDR-HuCAN20G2 was associated with the most frequent T cell proliferation response, inducing positive responses in 24% (5 donors) of the study cohort. In contrast, antibody HE-HuCAN20G2 induced fewer T cell proliferation responses with only 5% of the cohort responding positively. These results showed that the frequency of T cell proliferation responses is high for antibody CDR-HuCAN20G2 but low for HE-HuCAN20G2. No T cell proliferation responses were detected against the buffer control.

Analysis of the magnitude of T cell proliferation responses showed that although antibody CDR-HuCAN20G2 had a high frequency of response, the magnitude of responses were low (mean SI 2.13). For antibody HE-HuCAN20G2 no conclusions can be made regarding the magnitude of the T cell response due to the low number of responding donors (Table 15). Thus, the overall immunogenic potential of the antibodies was determined based on the frequency (%) of the positive T cell proliferation responses in the study cohort with CDR-HuCAN20G2 being more immunogenic than HE-HuCAN20G2.

TABLE 15

Summary of the mean magnitude (±SD) of positive T cell proliferation responses against the antibodies.

| Sample | Mean SI | +/− SD | Frequency (%) of Response |
|---|---|---|---|
| CDR-HuCAN20G2 | 2.13 | 0.09 | 24 |
| HE-HuCAN20G2 | 2.25 | 0.13 | 5 |
| KLH | 2.60 | 0.78 | 86 |

The mean SI was calculated from the average of all positive donor responses observed during the entire time course (days 5-8). The data includes borderline proliferation responses (SI≥1.90, p<0.05).

Kinetics of T Cell Responses

The overall timing of the proliferative responses can provide information as to the potential type of T cell response (naïve or recall). Maximal T cell proliferation detected on day 5 indicates that existing T cell precursor frequencies are high, whereas maximal proliferation on later days indicates a low existing T cell precursor frequency. A high immunogenic potential would be concordant with stimulation of T cells during the early phase of the time course. FIG. 25 summarizes the number of positive proliferation responses occurring against the samples on each day of the four day time course. The T cell responses against antibody CDR-HuCAN20G2 were observed mostly on days 7 and 8, suggesting that for this antibody the number of existing T cell precursors is low. Antibody HE-HuCAN20G2 induced one donor to respond and this was observed on days 6, 7 and 8. However, since only one responding donor was detected it is difficult to make a conclusion as to the number of T cell precursors for antibody HE-HUCAN20G2.

EpiScreen™ IL-2 ELISpot Assay

FIG. 26 and Table 12 show the responses obtained in the IL-2 ELISpot assay which measures IL-2 secretion by CD4+ T cells following stimulation with the two test antibodies. Similar to the proliferation assay, positive responses were recorded in donors that produced an SI≥2.00 with a significant (p<0.05) difference observed between test spw and background (untreated medium control). Borderline responses SI≥1.90 (p<0.05) are also highlighted. All samples induced positive IL-2 ELISpot responses in one or more donors and these were all significant (p<0.05) using an unpaired, two sample student's t-test. All PHA wells were positive for the presence of spots although SI values were not prepared for the ELISpot data as, after 8 days, the majority of wells contained spots too numerous to count (data not shown).

For the two test antibodies, the overall results of the IL-2 ELISpot assay were homologous to those obtained in the proliferation assay with both antibodies inducing the same frequency of T cell responses (Table 16). As in the proliferation assay, antibody CDR-HuCAN20G2 induced the most frequent T cell responses in the study cohort with 24% of donors responding positively (SI≥2.00, p<0.05), whereas antibody HE-HuCAN20G2 induced T cell responses in 5% of the study cohort. Assessment of the mean magnitude of positive (including borderline SI≥1.90, p<0.05) T cell responses against both antibodies was low (mean positive SI 2.39 for CDR-HuCAN20G2).

The frequency of T cell responses was low for HE-HuCAN20G2 which precludes making any direct correlation between strength of T cell response (magnitude) and immunogenicity. Assessment of the relative risk of immunogenicity of the test antibodies (based on the frequency of positive responses in the IL-2 ELISpot assay) showed that CDR-HuCAN20G2 was more immunogenic than HE-HuCAN20G2.

TABLE 16

Summary of the mean magnitude (±SD) of positive T cell IL-2 secretion responses against the antibodies.

| Sample | Mean SI | +/−SD | Frequency (%) of Response |
|---|---|---|---|
| CDR-HuCAN20G2 | 2.39 | 0.52 | 24 |
| HE-HuCAN20G2 | 2.63 | N/A | 5 |
| KLH | 4.13 | 1.48 | 95 |

The data includes borderline responses (SI≥1.90, p<0.05). N/A indicates no data available.

Interpretation of Results

The proliferation and IL-2 ELISpot assay data show that positive T cell responses were detected against both test antibodies in a proportion of the donors. The overall correlation between proliferation and IL-2 ELISpot assays was high (94% for KLH, Table 14) and thus, as in previous studies, responding donors were defined as those that mounted a positive response to each sample in both IL-2 ELISpot and proliferation assays. Table 14 shows a summary of positive responses against the antibodies in both proliferation and IL-2 ELISpot assays. Comparison of the data obtained from the proliferation and IL-2 ELISpot assays showed that the antibodies tested induced homologous frequencies of positive T cell responses between the assays. All donors produced a positive T cell response against PHA in the IL-2 ELISpot assay indicating that cells in the ex vivo cultures were functional (data not shown). Analysis of the combined datasets from these two assays revealed that the overall frequency and magnitude of responses was high for antibody CDR-HuCAN20G2 with 24% of donors responding in both proliferation and ELISpot assays and low for antibody HE-HuCAN20G2 with 5% of donors responding.

Conclusion

The overall correlation between proliferation and IL-2 ELISpot assay was high, responding donors were defined as those that mounted a positive response to each sample in both assays. Analysis of the combined datasets from two assays reveals that overall response was high for antibody CDR-huCAN20G2 with 24% of donors responding in both assays and low for antibody HE-huCAN20G2 with 5% of donors responding. Previous EpiScreen™ T cell assays with a range of biologics have showed a clear correlation between the percentage of donor T cell responses in the assay and the level of immunogenicity observed in clinic, whereas the protein therapeutics that induced >10% positive response are associated with risk of immunogenicity in the clinic. The current study results showed that, in comparison with other protein therapeutics tested in EpiScreen™ assays, antibody CDR-huCAN20G2 would be considered as having a risk of clinical immunogenicity. In contrast, antibody HE-huCAN20G2 would be considered as having a low risk of clinical immunogenicity.

Example 17: In Vivo Efficacy of Humanized CAN20G2 mAbs Against Toxin A Challenge The in vivo protective efficacy of the two humanized CAN20G2 anti-TcdA mAbs, HE-CAN20G2 and CDR- CAN20G2 were evaluated in the mouse lethal toxin challenge model (as noted in Example 8 above) by testing a low dose of antibody. Swiss Webster mice weighing 20-30 g were given 50 ug of mAb or controls at day 0 and allowed to rest. After 24 hrs, the mice were given a lethal dose of TcdA (100 ng). This dose kills 90-100% of animals by 24 hours in an unprotected state. The mice were observed for a period of 14 days for clinical symptoms, abnormality and local and systemic disease. All observations were recorded and the % survival was determined for each treatment group.

Results

As shown in FIGS. 27 and 28, both humanized CAN20G2 mAbs were efficacious in protecting against toxin A in vivo challenge. HE-CAN20G2 conferred better in vivo protection compared to CDA1 and CDR-CAN20G2. At the low dose of 0.05 mg/mouse, HE-CAN20G2 recipient mice had a higher survival rate (90%) compared to those treated with CDA1 (80%) and CDR-CAN20G2 (70%) against TcdA lethal challenge.

Example 18: Pharmacokinetic Analysis of Humanized Antibodies

Pharmacokinetic studies were conducted for CDR-huCAN20G2 and HE-huCAN20G2 in hamster model and rat model. In hamster study, Golden Syrian hamsters were injected intraperitoneally with 50 mg/kg of CDR-huCAN20G2. Blood samples were collected at 2 h, 24 h, 48 h, 72 h, 96 h, 168 h, 240 h and 336 h post-injection. Control samples were collected from test animal 5 days before injection and sentinel group at different time points. The blood samples were centrifuged at 8000 rpm for 10 minutes to obtain sera. In rat study, two groups of Sprague-Dawley rats were instrumented with a femoral vein catheter (FVC) for intravenous dosing and a jugular vein catheter (JVC) for blood collection. Two antibodies, CDR-huCAN20G2 and HE-huCAN20G2, were injected to each group of rats at 10 mg/kg dose level via single IV bolus followed by 0.5 mL saline flush. Blood samples were collected at pre-dose, 0.083, 1, 2, 4, 8, 24, 48, 72, 96, 120, 144, 168, 192, 216, 240, 264, 288 and 312 hours post-dose from the JVC. Whole blood (300 μL) samples were centrifuged at 2200×g for 10 minutes to isolate sera.

The antibody concentration in the sera was determined via ELISA. 96-well ELISA plate were coated overnight with goat anti-human IgG, affinity purified and monkey serum adsorbed (Novus Biologicals) at 1 μg/mL. Plates were washed with PBS-T and blocked with blocking buffer. The antibody reference standard was diluted in 1% pooled naïve hamster serum to generate a standard curve with a range of 0.098-100 ng/mL. Diluted test samples and standards were incubated 1.5 hours at room temperature. Plates were washed and incubated with HRP-goat anti-human IgG, affinity purified and monkey serum adsorbed (Novus Biologicals), developed with TMB peroxidase substrate system (R&D systems) and stopped with TMB peroxidase stop solution (R&D system). Plates were read on a SpectraMax plate reader at 450 nm. Antibody concentration in each animal at different time points as calculated using the standard curves.

Results:

For hamster PK study, noncompartmental pharmacokinetic analysis was performed using SAS Version 9.2 for Windows, the data are shown in Table 17. As indicated, CDR-huCAN20G2 demonstrated a terminal half life around 6 days with 50 mg/kg administration dose, which ensured antibody retention in future efficacy studies.

For rat PK study, noncompartmental pharmacokinetic analysis was performed using Watson, version 7.2.0.02 and the data are illustrated in Table 18 and FIGS. 29A and 29B. As indicated, the PK profiles of the two monoclonal antibodies are very similar. Comparable levels of exposure were exhibited and metabolism was close to the same rate.

TABLE 17

PK Study of Humanized Antibodies in Hamsters

| mAb | Cmax (μg/mL) | Tmax (hour) | $AUC_{(0-t)}$ (μg * hour/mL) | t½ Half-life (hour) |
|---|---|---|---|---|
| CDR-huCAN20G2 50 mg/kg | 244.9 | 24 | 36777.5 | 166.44 |

TABLE 18

PK Study of Humanized Antibodies in Rats

| mAb | $AUC_{(0-x)}$ μg * hour/mL | $Cl_{(0-x)}$ mL/kg/hr | $Vd_{ss(0-x)}$ mL/kg | t½ Half-life (hour) |
|---|---|---|---|---|
| CDR-huCAN20G2 10 mg/kg | 14533 | 0.689 | 81.8 | 170 |
| HE-huCAN20G2 10 mg/kg | 17500 | 0.573 | 70.2 | 209 |

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. An isolated monoclonal antibody, or an antigen-binding portion thereof comprising a heavy chain variable region and a light chain variable region, wherein the heavy chain variable region comprises three complementarity determining regions (CDRs), CDR1, CDR2, and CDR3, having the amino acid sequences set forth in SEQ ID NOs: 45, 46, and 47, respectively and wherein the light chain variable region comprises three CDRs, CDR1, CDR2, and CDR3, having the amino acid sequences set forth in SEQ ID NOs: 37, 38, and 39, respectively, and wherein the antibody or antigen-binding portion thereof specifically binds to *Clostridium difficile* (*C. difficile*) toxin A.

2. The antibody or antigen-binding portion thereof of claim 1, wherein the heavy chain variable region comprises the amino acid sequence SEQ ID NO: 44 and wherein the light chain variable region comprises the amino acid sequence SEQ ID NO:36.

3. The antibody or antigen-binding portion thereof of claim 1, wherein the dissociation constant ($K_D$) of the antibody, or antigen-binding portion thereof, is less than about $1\times10^{-11}$M.

4. The antibody or antigen-binding portion thereof of claim 1, wherein the antibody, or antigen-binding portion thereof, is humanized or chimeric.

5. The antibody or antigen-binding portion thereof of claim 1, wherein the antibody, or antigen-binding portion thereof, is selected from the group consisting of: (a) an scFv; (b) a Fab fragment; (c) an F(ab')2; and (d) a disulfide linked Fv.

6. The antibody or antigen-binding portion thereof of claim 1, wherein the antibody, or antigen-binding portion thereof, comprises at least one constant domain selected from the group consisting of: a) an IgG constant domain; and (b) an IgA constant domain.

7. The antibody or antigen-binding portion thereof of claim 1, wherein the antibody, or antigen-binding portion thereof, binds to fragment 4 of *C. difficile* toxin A.

8. The antibody or antigen-binding portion thereof of claim 1, wherein, in an in vivo toxin A challenge experiment, when the antibody, or an antigen-binding portion thereof, is administered to a mammal at a dosage ranging from about 8 mg/kg body weight to about 13 mg/kg body weight about 24 hours before the mammal is exposed to greater than about 100 ng of *C. difficile* toxin A, the chance of survival for the mammal is greater than about 80% within about 7 days.

9. The antibody or antigen-binding portion thereof of claim 1, wherein the antibody, or antigen-binding portion thereof, at a concentration ranging from about 4 μM to about 17 μM, neutralizes greater than about 40% of about 150 ng/ml *C. difficile* toxin A in an in vitro neutralization assay.

10. The antibody or antigen-binding portion thereof of claim 1, and at least one pharmaceutically acceptable carrier.

11. A method of treating *C. difficile*-associated disease comprising administering to a subject an effective amount of the antibody, or antigen-binding portion thereof, of claim 1.

12. The method of claim 11, wherein the antibody, or antigen-binding portion thereof, is administered intravenously, subcutaneously, intramuscularly or transdermally.

13. The method of claim 11, further comprising the step of administering to the subject a second agent.

14. The method of claim 13, wherein the second agent is a different antibody or fragment thereof.

15. The method of claim 13, wherein the second agent is an antibiotic.

16. The method of claim 15, wherein the antibiotic is vancomycin, metronidazole, or fidaxomicin.

* * * * *

UNITED STATES PATENT AND TRADEMARK OFFICE

CERTIFICATE OF CORRECTION

PATENT NO. : 9,994,630 B2
APPLICATION NO. : 15/338990
DATED : June 12, 2018
INVENTOR(S) : Jody Berry et al.

It is certified that error appears in the above-identified patent and that said Letters Patent is hereby corrected as shown below:

On the Title Page

Item (63), Line 1, delete “Continuation” and replace with -- Division --.

Signed and Sealed this
Twenty-first Day of August, 2018

Andrei Iancu
*Director of the United States Patent and Trademark Office*

SEQUENCE LISTING

```
<160> NUMBER OF SEQ ID NOS: 104

<210> SEQ ID NO 1
<211> LENGTH: 2710
<212> TYPE: PRT
<213> ORGANISM: Clostridium difficile
```

<400> SEQUENCE: 1

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Asn
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Leu Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Pro Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
```

```
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asp Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830
```

-continued

```
Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu  Asn Thr Ile Tyr Asp  Ser Ile Gln
        995                 1000                1005

Leu Val  Asn Leu Ile Ser Asn  Ala Val Asn Asp Thr  Ile Asn Val
    1010                 1015                 1020

Leu Pro  Thr Ile Thr Glu Gly  Ile Pro Ile Val Ser  Thr Ile Leu
    1025                 1030                 1035

Asp Gly  Ile Asn Leu Gly Ala  Ala Ile Lys Glu Leu  Leu Asp Glu
    1040                 1045                 1050

His Asp  Pro Leu Leu Lys Lys  Glu Leu Glu Ala Lys  Val Gly Val
    1055                 1060                 1065

Leu Ala  Ile Asn Met Ser Leu  Ser Ile Ala Ala Thr  Val Ala Ser
    1070                 1075                 1080

Ile Val  Gly Ile Gly Ala Glu  Val Thr Ile Phe Leu  Leu Pro Ile
    1085                 1090                 1095

Ala Gly  Ile Ser Ala Gly Ile  Pro Ser Leu Val Asn  Asn Glu Leu
    1100                 1105                 1110

Ile Leu  His Asp Lys Ala Thr  Ser Val Val Asn Tyr  Phe Asn His
    1115                 1120                 1125

Leu Ser  Glu Ser Lys Glu Tyr  Gly Pro Leu Lys Thr  Glu Asp Asp
    1130                 1135                 1140

Lys Ile  Leu Val Pro Ile Asp  Asp Leu Val Ile Ser  Glu Ile Asp
    1145                 1150                 1155

Phe Asn  Asn Asn Ser Ile Lys  Leu Gly Thr Cys Asn  Ile Leu Ala
    1160                 1165                 1170

Met Glu  Gly Gly Ser Gly His  Thr Val Thr Gly Asn  Ile Asp His
    1175                 1180                 1185

Phe Phe  Ser Ser Pro Tyr Ile  Ser Ser His Ile Pro  Ser Leu Ser
    1190                 1195                 1200

Val Tyr  Ser Ala Ile Gly Ile  Lys Thr Glu Asn Leu  Asp Phe Ser
    1205                 1210                 1215

Lys Lys  Ile Met Met Leu Pro  Asn Ala Pro Ser Arg  Val Phe Trp
    1220                 1225                 1230
```

-continued

```
Trp Glu  Thr Gly Ala Val Pro  Gly Leu Arg Ser Leu  Glu Asn Asn
    1235                 1240                 1245

Gly Thr  Lys Leu Leu Asp Ser  Ile Arg Asp Leu Tyr  Pro Gly Lys
    1250                 1255                 1260

Phe Tyr  Trp Arg Phe Tyr Ala  Phe Phe Asp Tyr Ala  Ile Thr Thr
    1265                 1270                 1275

Leu Lys  Pro Val Tyr Glu Asp  Thr Asn Thr Lys Ile  Lys Leu Asp
    1280                 1285                 1290

Lys Asp  Thr Arg Asn Phe Ile  Met Pro Thr Ile Thr  Thr Asp Glu
    1295                 1300                 1305

Ile Arg  Asn Lys Leu Ser Tyr  Ser Phe Asp Gly Ala  Gly Gly Thr
    1310                 1315                 1320

Tyr Ser  Leu Leu Leu Ser Ser  Tyr Pro Ile Ser Met  Asn Ile Asn
    1325                 1330                 1335

Leu Ser  Lys Asp Asp Leu Trp  Ile Phe Asn Ile Asp  Asn Glu Val
    1340                 1345                 1350

Arg Glu  Ile Ser Ile Glu Asn  Gly Thr Ile Lys Lys  Gly Asn Leu
    1355                 1360                 1365

Ile Glu  Asp Val Leu Ser Lys  Ile Asp Ile Asn Lys  Asn Lys Leu
    1370                 1375                 1380

Ile Ile  Gly Asn Gln Thr Ile  Asp Phe Ser Gly Asp  Ile Asp Asn
    1385                 1390                 1395

Lys Asp  Arg Tyr Ile Phe Leu  Thr Cys Glu Leu Asp  Asp Lys Ile
    1400                 1405                 1410

Ser Leu  Ile Ile Glu Ile Asn  Leu Val Ala Lys Ser  Tyr Ser Leu
    1415                 1420                 1425

Leu Leu  Ser Gly Asp Lys Asn  Tyr Leu Ile Ser Asn  Leu Ser Asn
    1430                 1435                 1440

Thr Ile  Glu Lys Ile Asn Thr  Leu Gly Leu Asp Ser  Lys Asn Ile
    1445                 1450                 1455

Ala Tyr  Asn Tyr Thr Asp Glu  Ser Asn Asn Lys Tyr  Phe Gly Ala
    1460                 1465                 1470

Ile Ser  Lys Thr Ser Gln Lys  Ser Ile Ile His Tyr  Lys Lys Asp
    1475                 1480                 1485

Ser Lys  Asn Ile Leu Glu Phe  Tyr Asn Gly Ser Thr  Leu Glu Phe
    1490                 1495                 1500

Asn Ser  Lys Asp Phe Ile Ala  Glu Asp Ile Asn Val  Phe Met Lys
    1505                 1510                 1515

Asp Asp  Ile Asn Thr Ile Thr  Gly Lys Tyr Tyr Val  Asp Asn Asn
    1520                 1525                 1530

Thr Asp  Lys Ser Ile Asp Phe  Ser Ile Ser Leu Val  Ser Lys Asn
    1535                 1540                 1545

Gln Val  Lys Val Asn Gly Leu  Tyr Leu Asn Glu Ser  Val Tyr Ser
    1550                 1555                 1560

Ser Tyr  Leu Asp Phe Val Lys  Asn Ser Asp Gly His  His Asn Thr
    1565                 1570                 1575

Ser Asn  Phe Met Asn Leu Phe  Leu Asn Asn Ile Ser  Phe Trp Lys
    1580                 1585                 1590

Leu Phe  Gly Phe Glu Asn Ile  Asn Phe Val Ile Asp  Lys Tyr Phe
    1595                 1600                 1605

Thr Leu  Val Gly Lys Thr Asn  Leu Gly Tyr Val Glu  Phe Ile Cys
    1610                 1615                 1620

Asp Asn  Asn Lys Asn Ile Asp  Ile Tyr Phe Gly Glu  Trp Lys Thr
```

```
    1625                1630                1635

Ser Ser  Ser Lys Ser Thr Ile  Phe Ser Gly Asn Gly  Arg Asn Val
    1640                1645                1650

Val Val  Glu Pro Ile Tyr Asn  Pro Asp Thr Gly Glu  Asp Ile Ser
    1655                1660                1665

Thr Ser  Leu Asp Phe Ser Tyr  Glu Pro Leu Tyr Gly  Ile Asp Arg
    1670                1675                1680

Tyr Ile  Asn Lys Val Leu Ile  Ala Pro Asp Leu Tyr  Thr Ser Leu
    1685                1690                1695

Ile Asn  Ile Asn Thr Asn Tyr  Tyr Ser Asn Glu Tyr  Tyr Pro Glu
    1700                1705                1710

Ile Ile  Val Leu Asn Pro Asn  Thr Phe His Lys Lys  Val Asn Ile
    1715                1720                1725

Asn Leu  Asp Ser Ser Ser Phe  Glu Tyr Lys Trp Ser  Thr Glu Gly
    1730                1735                1740

Ser Asp  Phe Ile Leu Val Arg  Tyr Leu Glu Glu Ser  Asn Lys Lys
    1745                1750                1755

Ile Leu  Gln Lys Ile Arg Ile  Lys Gly Ile Leu Ser  Asn Thr Gln
    1760                1765                1770

Ser Phe  Asn Lys Met Ser Ile  Asp Phe Lys Asp Ile  Lys Lys Leu
    1775                1780                1785

Ser Leu  Gly Tyr Ile Met Ser  Asn Phe Lys Ser Phe  Asn Ser Glu
    1790                1795                1800

Asn Glu  Leu Asp Arg Asp His  Leu Gly Phe Lys Ile  Ile Asp Asn
    1805                1810                1815

Lys Thr  Tyr Tyr Tyr Asp Glu  Asp Ser Lys Leu Val  Lys Gly Leu
    1820                1825                1830

Ile Asn  Ile Asn Asn Ser Leu  Phe Tyr Phe Asp Pro  Ile Glu Ser
    1835                1840                1845

Asn Leu  Val Thr Gly Trp Gln  Thr Ile Asn Gly Lys  Lys Tyr Tyr
    1850                1855                1860

Phe Asp  Ile Asn Thr Gly Ala  Ala Ser Thr Ser Tyr  Lys Ile Ile
    1865                1870                1875

Asn Gly  Lys His Phe Tyr Phe  Asn Asn Asn Gly Val  Met Gln Leu
    1880                1885                1890

Gly Val  Phe Lys Gly Pro Asp  Gly Phe Glu Tyr Phe  Ala Pro Ala
    1895                1900                1905

Asn Thr  Gln Asn Asn Asn Ile  Glu Gly Gln Ala Ile  Val Tyr Gln
    1910                1915                1920

Ser Lys  Phe Leu Thr Leu Asn  Gly Lys Lys Tyr Tyr  Phe Asp Asn
    1925                1930                1935

Asp Ser  Lys Ala Val Thr Gly  Trp Arg Ile Ile Asn  Asn Glu Lys
    1940                1945                1950

Tyr Tyr  Phe Asn Pro Asn Asn  Ala Ile Ala Ala Val  Gly Leu Gln
    1955                1960                1965

Val Ile  Asp Asn Asn Lys Tyr  Tyr Phe Asn Pro Asp  Thr Ala Ile
    1970                1975                1980

Ile Ser  Lys Gly Trp Gln Thr  Val Asn Gly Ser Arg  Tyr Tyr Phe
    1985                1990                1995

Asp Thr  Asp Thr Ala Ile Ala  Phe Asn Gly Tyr Lys  Thr Ile Asp
    2000                2005                2010

Gly Lys  His Phe Tyr Phe Asp  Ser Asp Cys Val Val  Lys Ile Gly
    2015                2020                2025
```

-continued

```
Val Phe  Ser Gly Ser Asn Gly  Phe Glu Tyr Phe Ala  Pro Ala Asn
    2030                 2035                 2040

Thr Tyr  Asn Asn Asn Ile Glu  Gly Gln Ala Ile Val  Tyr Gln Ser
    2045                 2050                 2055

Lys Phe  Leu Thr Leu Asn Gly  Lys Lys Tyr Tyr Phe  Asp Asn Asn
    2060                 2065                 2070

Ser Lys  Ala Val Thr Gly Trp  Gln Thr Ile Asp Ser  Lys Lys Tyr
    2075                 2080                 2085

Tyr Phe  Asn Thr Asn Thr Ala  Glu Ala Ala Thr Gly  Trp Gln Thr
    2090                 2095                 2100

Ile Asp  Gly Lys Lys Tyr Tyr  Phe Asn Thr Asn Thr  Ala Glu Ala
    2105                 2110                 2115

Ala Thr  Gly Trp Gln Thr Ile  Asp Gly Lys Lys Tyr  Tyr Phe Asn
    2120                 2125                 2130

Thr Asn  Thr Ser Ile Ala Ser  Thr Gly Tyr Thr Ile  Ile Asn Gly
    2135                 2140                 2145

Lys Tyr  Phe Tyr Phe Asn Thr  Asp Gly Ile Met Gln  Ile Gly Val
    2150                 2155                 2160

Phe Lys  Val Pro Asn Gly Phe  Glu Tyr Phe Ala Pro  Ala Asn Thr
    2165                 2170                 2175

His Asn  Asn Asn Ile Glu Gly  Gln Ala Ile Leu Tyr  Gln Asn Lys
    2180                 2185                 2190

Phe Leu  Thr Leu Asn Gly Lys  Lys Tyr Tyr Phe Gly  Ser Asp Ser
    2195                 2200                 2205

Lys Ala  Ile Thr Gly Trp Gln  Thr Ile Asp Gly Lys  Lys Tyr Tyr
    2210                 2215                 2220

Phe Asn  Pro Asn Asn Ala Ile  Ala Ala Thr His Leu  Cys Thr Ile
    2225                 2230                 2235

Asn Asn  Asp Lys Tyr Tyr Phe  Ser Tyr Asp Gly Ile  Leu Gln Asn
    2240                 2245                 2250

Gly Tyr  Ile Thr Ile Glu Arg  Asn Asn Phe Tyr Phe  Asp Ala Asn
    2255                 2260                 2265

Asn Glu  Ser Lys Met Val Thr  Gly Val Phe Lys Gly  Pro Asn Gly
    2270                 2275                 2280

Phe Glu  Tyr Phe Ala Pro Ala  Asn Thr His Asn Asn  Asn Ile Glu
    2285                 2290                 2295

Gly Gln  Ala Ile Val Tyr Gln  Asn Lys Phe Leu Thr  Leu Asn Gly
    2300                 2305                 2310

Lys Lys  Tyr Tyr Phe Asp Asn  Asp Ser Lys Ala Val  Thr Gly Trp
    2315                 2320                 2325

Gln Thr  Ile Asp Ser Lys Lys  Tyr Tyr Phe Asn Leu  Asn Thr Ala
    2330                 2335                 2340

Val Ala  Val Thr Gly Trp Gln  Thr Ile Asp Gly Glu  Lys Tyr Tyr
    2345                 2350                 2355

Phe Asn  Leu Asn Thr Ala Glu  Ala Ala Thr Gly Trp  Gln Thr Ile
    2360                 2365                 2370

Asp Gly  Lys Arg Tyr Tyr Phe  Asn Thr Asn Thr Tyr  Ile Ala Ser
    2375                 2380                 2385

Thr Gly  Tyr Thr Ile Ile Asn  Gly Lys His Phe Tyr  Phe Asn Thr
    2390                 2395                 2400

Asp Gly  Ile Met Gln Ile Gly  Val Phe Lys Gly Pro  Asp Gly Phe
    2405                 2410                 2415
```

-continued

```
Glu Tyr Phe Ala Pro Ala Asn Thr His Asn Asn Asn Ile Glu Gly
    2420                2425                2430

Gln Ala Ile Leu Tyr Gln Asn Lys Phe Leu Thr Leu Asn Gly Lys
    2435                2440                2445

Lys Tyr Tyr Phe Gly Ser Asp Ser Lys Ala Val Thr Gly Leu Arg
    2450                2455                2460

Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Tyr Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
    2540                2545                2550

Arg Phe Leu Tyr Leu His Asp Asn Ile Tyr Tyr Phe Gly Asn Asp
    2555                2560                2565

Ser Lys Ala Ala Thr Gly Trp Ala Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Pro Asn Gly Phe Glu Tyr Phe Ala Pro Ala
    2615                2620                2625

Asn Thr Asp Ala Asn Asn Ile Asp Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Ser Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
    2690                2695                2700

Lys Ala Pro Gly Ile Tyr Gly
    2705                2710
```

<210> SEQ ID NO 2
<211> LENGTH: 8133
<212> TYPE: DNA
<213> ORGANISM: Clostridium difficile

<400> SEQUENCE: 2

```
atgtctttaa tatctaaaga agagttaata aaactcgcat atagcattag accaagagaa     60

aatgagtata aaactatact aactaattta gacgaatata ataagttaac tacaaacaat    120

aatgaaaata aatatttaca attaaaaaaa ctaaatgaat caattgatgt ttttatgaat    180

aaatataaaa attcaagcag aaatagagca ctctctaatc taaaaaaaga tatattaaaa    240

gaagtaattc ttattaaaaa ttccaataca agtcctgtag aaaaaaattt acattttgta    300

tggataggtg gagaagtcag tgatattgct cttgaataca taaaacaatg ggctgatatt    360
```

```
aatgcagaat ataatattaa actgtggtat gatagtgaag cattcttagt caatacacta    420
aaaaaggcta tagttgaatc ttctaccact gaagcattac agctactaga ggaagagatt    480
caaaatcctc aatttgataa tatgaaattt tacaaaaaaa ggatggaatt tatatatgat    540
agacaaaaaa ggtttataaa ttattataaa tctcaaatca ataaacctac agtacctaca    600
atagatgata ttataaagtc tcatctagta tctgaatata atagagatga aactttatta    660
gaatcatata gaacaaattc tttgagaaaa ataaatagta atcatgggat agatatcagg    720
gctaatagtt tgtttacaga acaagagtta ttaaatattt atagtcagga gttgttaaat    780
cgtgggaatt tagctgcagc atctgacata gtaagattat tagccctaaa aaattttggc    840
ggagtatatt tagatgttga tatgcttcca ggtattcact ctgatttatt taaaacaata    900
cctagaccta gctctattgg actagaccgt tgggaaatga taaaattaga ggctattatg    960
aagtataaaa aatatataaa taattataca tcagaaaact ttgataaact tgatcaacaa   1020
ttaaaagata attttaaact cattatagaa agtaaaagtg aaaaatctga gatattttct   1080
aaattagaaa atttaaatgt atctgatctt gaaattaaaa tagctttcgc tttaggcagt   1140
gttataaatc aagccttgat atcaaaacaa ggttcatatc ttactaacct agtaatagaa   1200
caagtaaaaa atagatatca atttttaaac caacacctta acccagccat agagtctgac   1260
aataacttca cagatactac taagattttt catgattcac tatttaattc agctaccgca   1320
gaaaactcta tgtttttaac aaaaatagca ccatacttac aagtaggttt tatgccagaa   1380
gctcgctcca caataagttt aagtggtcca ggagcttatg catcagctta ctatgatttc   1440
ataaatttac aagaaaatac tatagaaaaa actttaaaag catcagattt aatagaattt   1500
aaattcccag aaaataatct atctcaattg acagaacaag aaataaatag tctatggagc   1560
tttgatcaag caagtgcaaa atatcaattt gagaaatatg taagagatta tactggtgga   1620
tctctttctg aagacaatgg ggtagacttt aataaaaata ctgccctcga caaaaactat   1680
ttattaaata ataaaattcc atcaaacaat gtagaagaag ctggaagtaa aaattatgtt   1740
cattatatca tacagttaca aggagatgat ataagttatg aagcaacatg caatttattt   1800
tctaaaaatc ctaaaaatag tattattata caacgaaata tgaatgaaag tgcaaaaagt   1860
tacttttttaa gtgatgatgg agaatctatt ttagaattaa ataaatatag gatacctgaa   1920
agattaaaaa ataaggaaaa agtaaaagta acctttattg gacatggtaa agatgaattc   1980
aacacaagcg aatttgctag attaagtgta gattcacttt ccaatgagat aagttcattt   2040
ttagatacca taaaattaga tatatcacct aaaaatgtag aagtaaactt gcttggatgt   2100
aatatgttta gttatgattt taatgttgaa gaaacttatc ctggtaagtt actattaagt   2160
attatggaca aaattacttc cactttacct gatgtaaata aagattctat tactatagga   2220
gcaaatcaat atgaagtaag aattaatagt gagggaagaa aagaacttct agctcactca   2280
ggtaaatgga taaataaaga ggaagctatt atgagcgatt tatctagtaa agaatacatt   2340
ttttttgatt ccatagataa taagctaaaa gcaaagtcca agaatattcc aggtttagcg   2400
tcaatatcag aagatataaa aacattatta cttgatgcaa gtgttagtcc tgatacaaaa   2460
tttattttaa ataatcttaa gcttaatatt gaatcttcta ttggtgatta catttattat   2520
gaaaaattag aacctgttaa aaatataatc cacaattcta tagatgattt aatagatgag   2580
ttcaatctac ttgaaaatgt atctgatgaa ttatatgaat taaaaaaatt aaataatcta   2640
gatgagaagt atttaatatc ttttgaagat atctcaaaaa ataattcaac ttattctgta   2700
```

-continued

```
agatttatta acaaaagtaa tggtgaatca gtttatgtag agacagaaaa agaaattttt   2760
tcaaaatata gcgaacatat tacaaaagaa ataagtacta taaagaatag tataattaca   2820
gatgttaatg gtaatttatt ggataatata cagttagatc atacttctca agttaataca   2880
ttaaacgcag cattctttat tcaatcatta atagattata gtagcaataa agatgtactg   2940
aatgatttaa gtacctcagt taaggttcaa ctttatgctc aactatttag tacaggttta   3000
aatactatat atgactctat ccaattagta aatttaatat caaatgcagt aaatgatact   3060
ataaatgtac tacctacaat aacagagggg atacctattg tatctactat attagacgga   3120
ataaacttag gtgcagcaat taaggaatta ctagacgaac atgacccatt actaaaaaaa   3180
gaactagaag ctaaggtggg tgttttagca ataaatatgt cattatctat agctgcaacg   3240
gtagcttcaa ttgttggaat aggtgctgaa gttactattt tcttattacc tatagctggt   3300
atatctgcgg gaataccttc attagttaat aatgaattaa tattgcatga taaggcaact   3360
tcagtggtaa actattttaa tcatttgtct gaatctaaag aatatggccc tcttaaaaca   3420
gaagatgata aaattttagt tcctattgat gatttagtaa tatcagaaat agattttaat   3480
aataattcga taaaactagg aacatgtaat atattagcaa tggagggggg atcaggacac   3540
acagtgactg gtaatataga tcactttttc tcatctccat atataagctc tcatattcct   3600
tcattatcag tttattctgc aataggtata aaaacagaaa atctagattt ttcaaaaaaa   3660
ataatgatgt taccaaatgc tccttcaaga gtgttttggt gggaaactgg agcagttcca   3720
ggtttaagat cattggaaaa taatgggact aaattgcttg attcaataag agatttatac   3780
ccaggcaaat tttactggag attctatgcc tttttcgatt atgcaataac tacattaaaa   3840
ccagtgtatg aagacactaa tactaaaatt aaactagata aagatactag aaactttata   3900
atgccaacta taactactga cgaaattaga aacaaattat cttattcatt tgatggagca   3960
ggaggaactt actctttatt attatcttca tatccaatat caatgaatat aaatttatct   4020
aaagatgatt tatggatatt taatattgat aatgaagtaa gagaaatatc tatagaaaat   4080
ggtactatta aaaaaggaaa tttaatagaa gatgttttaa gtaaaattga tataaataaa   4140
aataaactta ttataggcaa tcaaacaata gatttttcag gtgatataga taacaaagat   4200
agatatatat tcttgacttg tgagttagat gataaaatta gtttaataat agaaataaat   4260
cttgttgcaa aatcttatag tttgttattg tctggggata aaaattattt gatatccaat   4320
ttatctaata ctattgagaa aatcaatact ttaggcctag atagtaaaaa tatagcttac   4380
aattacactg atgaatctaa taataaatat tttggagcta tatctaaaac aagtcaaaaa   4440
agcataatac attataaaaa agacagtaaa aatatattag aattttataa tggcagtaca   4500
ttagaattta acagtaaaga ctttattgct gaagatataa atgtatttat gaaagatgat   4560
attaatacta taacaggaaa atactatgtt gataataata ctgataaaag tatagatttc   4620
tctatttctt tagttagtaa aaatcaagta aaagtaaatg gattatattt aaatgaatcc   4680
gtatactcat cttaccttga ttttgtgaaa aattcagatg gacaccataa tacttctaat   4740
tttatgaatt tatttttgaa caatataagt ttctggaaat tgtttgggtt tgaaaatata   4800
aattttgtaa tcgataaata ctttaccctt gttggtaaaa ctaatcttgg atatgtagaa   4860
tttatttgtg acaataataa aaatatagat atatattttg gtgaatggaa aacatcgtca   4920
tctaaaagca ctatatttag cggaaatggt agaaatgttg tagtagagcc tatatataat   4980
cctgatacgg gtgaagatat atctacttca ctagattttt cctatgaacc tctctatgga   5040
atagatagat atatcaataa agtattgata gcacctgatt tatatacaag tttaataaat   5100
```

```
attaatacca attattattc aaatgagtac taccctgaga ttatagttct taacccaaat   5160
acattccaca aaaaagtaaa tataaattta gatagttctt cttttgagta taaatggtct   5220
acagaaggaa gtgactttat tttagttaga tacttagaag aaagtaataa aaaaatatta   5280
caaaaaataa gaatcaaagg tatcttatct aatactcaat catttaataa aatgagtata   5340
gattttaaag atattaaaaa actatcatta ggatatataa tgagtaattt taaatcattt   5400
aattctgaaa atgaattaga tagagatcat ttaggattta aaataataga taataaaact   5460
tattactatg atgaagatag taaattagtt aaaggattaa tcaatataaa taattcatta   5520
ttctattttg atcctataga atctaactta gtaactggat ggcaaactat caatggtaaa   5580
aaatattatt ttgatataaa tactggagca gcttcaacta gttataaaat tattaatggt   5640
aaacactttt attttaataa taatggtgtg atgcagttag gagtatttaa aggacctgat   5700
ggatttgagt attttgcacc tgccaatact cagaataata acatagaagg tcaggctata   5760
gtttatcaaa gtaaattctt aactttgaat ggcaaaaaat attattttga taatgactca   5820
aaagcagtca ctggatggag gattattaac aatgagaaat attactttaa tcctaataat   5880
gctattgctg cagtcggatt gcaagtaatt gacaataata agtattattt caatcctgac   5940
actgctatca tctcaaaagg ttggcagact gttaatggta gtagatacta ctttgatact   6000
gataccgcta ttgcctttaa tggttataaa actattgatg gtaaacactt ttattttgat   6060
agtgattgtg tagtgaaaat aggtgtgttt agtggctcta atggatttga atatttcgca   6120
cctgctaata cttataataa taacatagaa ggtcaggcta tagtttatca aagtaaattc   6180
ttaactttga atggtaaaaa atattacttt gataataact caaaagcagt taccggatgg   6240
caaactattg atagtaaaaa atattacttt aatactaaca ctgctgaagc agctactgga   6300
tggcaaacta ttgatggtaa aaagtattac tttaatacta acactgctga agcagctact   6360
ggatggcaaa ctattgatgg taaaaaatat tactttaata ctaacacttc tatagcttca   6420
actggttata caattattaa tggtaaatat ttttatttta atactgatgg tattatgcag   6480
ataggagtgt ttaaagtacc taatggattt gaatactttg cacctgctaa tactcataat   6540
aataacatag aaggtcaagc tatactttac caaaataaat tcttaacttt gaatggtaaa   6600
aaatattact ttggtagtga ctcaaaagca attactggat ggcaaaccat tgatggtaaa   6660
aaatattact ttaatcctaa taatgctatt gctgcgactc atctatgcac tataaataac   6720
gacaagtatt actttagtta tgatggaatt cttcaaaatg gatatattac tattgaaaga   6780
aataatttct attttgatgc taataatgaa tctaaaatgg taacaggagt atttaaagga   6840
cctaatggat ttgagtattt tgcacctgct aatactcata ataataacat agaaggtcag   6900
gctatagttt accagaataa attcttaact ttgaatggca aaaaatatta ttttgataat   6960
gactcaaaag cagttactgg atggcaaact attgatagta aaaaatatta ctttaatctt   7020
aacactgctg ttgcagttac tggatggcaa actattgatg gtgaaaaata ttactttaat   7080
cttaacactg ctgaagcagc tactggatgg caaactattg atggtaaaag atactacttt   7140
aatactaaca cttatatagc ttcaactggt tatacgatta ttaatggtaa acatttttat   7200
tttaatactg atggtattat gcagatagga gtgtttaaag gacctgatgg atttgaatac   7260
tttgcacctg ctaatactca taataataac atagaaggtc aagctatact ttaccaaaat   7320
aaattcttaa ctttgaatgg taaaaaatat tactttggta gtgactcaaa agcagttacc   7380
ggattgcgaa ctattgatgg taaaaaatat tactttaata ctaacactgc tgttgcagtt   7440
```

```
actggatggc aaactattaa tggtaaaaaa tactacttta atactaacac ttatatagct   7500

tcaactggtt atacaattat tagtggtaaa catttttatt ttaatactga tggtattatg   7560

cagataggag tgtttaaagg acctgatgga tttgaatact ttgcacctgc taatacggat   7620

gctaacaaca tagaaggtca agctatacgt tatcaaaata gattcctata tttacatgac   7680

aatatatatt actttggcaa tgattcaaaa gcggctactg gttgggcaac tattgatggt   7740

aatagatatt acttcgagcc taatacagct atgggtgcga atggttataa aactattgat   7800

aataaaaatt tttactttag aaatggttta cctcagatag gagtgtttaa aggacctaat   7860

ggatttgaat actttgcacc tgctaatacg gatgctaaca atatagatgg tcaagctata   7920

cgttatcaaa atagattcct acatttactt ggaaaaatat attactttgg taataactca   7980

aaagcagtta ctggatggca aactattaat agtaaagtat attactttat gcctgatact   8040

gctatggctg cagctggtgg acttttcgag attgatggtg ttatatattt ctttggtgtt   8100

gatggagtaa aagcccctgg gatatatggc taa                                8133
```

<210> SEQ ID NO 3
<211> LENGTH: 858
<212> TYPE: PRT
<213> ORGANISM: Clostridium difficile

<400> SEQUENCE: 3

```
Gly Trp Gln Thr Ile Asn Gly Lys Lys Tyr Tyr Phe Asp Ile Asn Thr
1               5                   10                  15

Gly Ala Ala Leu Ile Ser Tyr Lys Ile Ile Asn Gly Lys His Phe Tyr
            20                  25                  30

Phe Asn Asn Asp Gly Val Met Gln Leu Gly Val Phe Lys Gly Pro Asp
        35                  40                  45

Gly Phe Glu Tyr Phe Ala Pro Ala Asn Thr Gln Asn Asn Asn Ile Glu
    50                  55                  60

Gly Gln Ala Ile Val Tyr Gln Ser Lys Phe Leu Thr Leu Asn Gly Lys
65                  70                  75                  80

Lys Tyr Tyr Phe Asp Asn Asp Ser Lys Ala Val Thr Gly Trp Arg Ile
                85                  90                  95

Ile Asn Asn Glu Lys Tyr Tyr Phe Asn Pro Asn Asn Ala Ile Ala Ala
            100                 105                 110

Val Gly Leu Gln Val Ile Asp Asn Asn Lys Tyr Tyr Phe Asn Pro Asp
        115                 120                 125

Thr Ala Ile Ile Ser Lys Gly Trp Gln Thr Val Asn Gly Ser Arg Tyr
    130                 135                 140

Tyr Phe Asp Thr Asp Thr Ala Ile Ala Phe Asn Gly Tyr Lys Thr Ile
145                 150                 155                 160

Asp Gly Lys His Phe Tyr Phe Asp Ser Asp Cys Val Val Lys Ile Gly
                165                 170                 175

Val Phe Ser Thr Ser Asn Gly Phe Glu Tyr Phe Ala Pro Ala Asn Thr
            180                 185                 190

Tyr Asn Asn Asn Ile Glu Gly Gln Ala Ile Val Tyr Gln Ser Lys Phe
        195                 200                 205

Leu Thr Leu Asn Gly Lys Lys Tyr Tyr Phe Asp Asn Asn Ser Lys Ala
    210                 215                 220

Val Thr Gly Trp Gln Thr Ile Asp Ser Lys Lys Tyr Tyr Phe Asn Thr
225                 230                 235                 240

Asn Thr Ala Glu Ala Ala Thr Gly Trp Gln Thr Ile Asp Gly Lys Lys
                245                 250                 255
```

-continued

```
Tyr Tyr Phe Asn Thr Asn Thr Ala Glu Ala Ala Thr Gly Trp Gln Thr
            260                 265                 270

Ile Asp Gly Lys Lys Tyr Tyr Phe Asn Thr Asn Thr Ala Ile Ala Ser
        275                 280                 285

Thr Gly Tyr Thr Ile Ile Asn Gly Lys His Phe Tyr Phe Asn Thr Asp
    290                 295                 300

Gly Ile Met Gln Ile Gly Val Phe Lys Gly Pro Asn Gly Phe Glu Tyr
305                 310                 315                 320

Phe Ala Pro Ala Asn Thr Asp Ala Asn Asn Ile Glu Gly Gln Ala Ile
                325                 330                 335

Leu Tyr Gln Asn Glu Phe Leu Thr Leu Asn Gly Lys Lys Tyr Tyr Phe
            340                 345                 350

Gly Ser Asp Ser Lys Ala Val Thr Gly Trp Arg Ile Ile Asn Asn Lys
        355                 360                 365

Lys Tyr Tyr Phe Asn Pro Asn Asn Ala Ile Ala Ala Ile His Leu Cys
    370                 375                 380

Thr Ile Asn Asn Asp Lys Tyr Tyr Phe Ser Tyr Asp Gly Ile Leu Gln
385                 390                 395                 400

Asn Gly Tyr Ile Thr Ile Glu Arg Asn Asn Phe Tyr Phe Asp Ala Asn
                405                 410                 415

Asn Glu Ser Lys Met Val Thr Gly Val Phe Lys Gly Pro Asn Gly Phe
            420                 425                 430

Glu Tyr Phe Ala Pro Ala Asn Thr His Asn Asn Asn Ile Glu Gly Gln
        435                 440                 445

Ala Ile Val Tyr Gln Asn Lys Phe Leu Thr Leu Asn Gly Lys Lys Tyr
    450                 455                 460

Tyr Phe Asp Asn Asp Ser Lys Ala Val Thr Gly Trp Gln Thr Ile Asp
465                 470                 475                 480

Gly Lys Lys Tyr Tyr Phe Asn Leu Asn Thr Ala Glu Ala Ala Thr Gly
                485                 490                 495

Trp Gln Thr Ile Asp Gly Lys Lys Tyr Tyr Phe Asn Leu Asn Thr Ala
            500                 505                 510

Glu Ala Ala Thr Gly Trp Gln Thr Ile Asp Gly Lys Lys Tyr Tyr Phe
        515                 520                 525

Asn Thr Asn Thr Phe Ile Ala Ser Thr Gly Tyr Thr Ser Ile Asn Gly
    530                 535                 540

Lys His Phe Tyr Phe Asn Thr Asp Gly Ile Met Gln Ile Gly Val Phe
545                 550                 555                 560

Lys Gly Pro Asn Gly Phe Glu Tyr Phe Ala Pro Ala Asn Thr His Asn
                565                 570                 575

Asn Asn Ile Glu Gly Gln Ala Ile Leu Tyr Gln Asn Lys Phe Leu Thr
            580                 585                 590

Leu Asn Gly Lys Lys Tyr Tyr Phe Gly Ser Asp Ser Lys Ala Val Thr
        595                 600                 605

Gly Leu Arg Thr Ile Asp Gly Lys Lys Tyr Tyr Phe Asn Thr Asn Thr
    610                 615                 620

Ala Val Ala Val Thr Gly Trp Gln Thr Ile Asn Gly Lys Lys Tyr Tyr
625                 630                 635                 640

Phe Asn Thr Asn Thr Ser Ile Ala Ser Thr Gly Tyr Thr Ile Ile Ser
                645                 650                 655

Gly Lys His Phe Tyr Phe Asn Thr Asp Gly Ile Met Gln Ile Gly Val
            660                 665                 670
```

```
Phe Lys Gly Pro Asp Gly Phe Glu Tyr Phe Ala Pro Ala Asn Thr Asp
        675                 680                 685

Ala Asn Asn Ile Glu Gly Gln Ala Ile Arg Tyr Gln Asn Arg Phe Leu
    690                 695                 700

Tyr Leu His Asp Asn Ile Tyr Tyr Phe Gly Asn Asn Ser Lys Ala Ala
705                 710                 715                 720

Thr Gly Trp Val Thr Ile Asp Gly Asn Arg Tyr Tyr Phe Glu Pro Asn
                725                 730                 735

Thr Ala Met Gly Ala Asn Gly Tyr Lys Thr Ile Asp Asn Lys Asn Phe
            740                 745                 750

Tyr Phe Arg Asn Gly Leu Pro Gln Ile Gly Val Phe Lys Gly Ser Asn
        755                 760                 765

Gly Phe Glu Tyr Phe Ala Pro Ala Asn Thr Asp Ala Asn Asn Ile Glu
    770                 775                 780

Gly Gln Ala Ile Arg Tyr Gln Asn Arg Phe Leu His Leu Leu Gly Lys
785                 790                 795                 800

Ile Tyr Tyr Phe Gly Asn Asn Ser Lys Ala Val Thr Gly Trp Gln Thr
                805                 810                 815

Ile Asn Gly Lys Val Tyr Tyr Phe Met Pro Asp Thr Ala Met Ala Ala
            820                 825                 830

Ala Gly Gly Leu Phe Glu Ile Asp Gly Val Ile Tyr Phe Phe Gly Val
        835                 840                 845

Asp Gly Val Lys Ala Pro Gly Ile Tyr Gly
    850                 855
```

<210> SEQ ID NO 4
<211> LENGTH: 108
<212> TYPE: PRT
<213> ORGANISM: Mouse

<400> SEQUENCE: 4

```
Gln Val Val Leu Thr Gln Ser Pro Ala Ile Met Ser Ala Ser Leu Gly
1               5                   10                  15

Glu Arg Val Thr Met Thr Cys Thr Ala Ser Ser Ser Val Ile Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Thr Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Leu Gln Tyr His Arg Ser Pro
                85                  90                  95

Arg Thr Phe Gly Gly Gly Thr Lys Leu Glu Ile Lys
            100                 105
```

<210> SEQ ID NO 5
<211> LENGTH: 7
<212> TYPE: PRT
<213> ORGANISM: Mouse

<400> SEQUENCE: 5

```
Ser Ser Val Ile Ser Ser Tyr
1               5
```

<210> SEQ ID NO 6
<211> LENGTH: 3

<212> TYPE: PRT
<213> ORGANISM: Mouse

<400> SEQUENCE: 6

Ser Thr Ser
1

<210> SEQ ID NO 7
<211> LENGTH: 11
<212> TYPE: PRT
<213> ORGANISM: Mouse

<400> SEQUENCE: 7

Cys Leu Gln Tyr His Arg Ser Pro Arg Thr Phe
1               5                   10

<210> SEQ ID NO 8
<211> LENGTH: 26
<212> TYPE: PRT
<213> ORGANISM: Mouse

<400> SEQUENCE: 8

Gln Val Val Leu Thr Gln Ser Pro Ala Ile Met Ser Ala Ser Leu Gly
1               5                   10                  15

Glu Arg Val Thr Met Thr Cys Thr Ala Ser
            20                  25

<210> SEQ ID NO 9
<211> LENGTH: 17
<212> TYPE: PRT
<213> ORGANISM: Mouse

<400> SEQUENCE: 9

Leu His Trp Tyr Gln Gln Lys Pro Gly Ser Ser Pro Lys Leu Trp Ile
1               5                   10                  15

Tyr

<210> SEQ ID NO 10
<211> LENGTH: 35
<212> TYPE: PRT
<213> ORGANISM: Mouse

<400> SEQUENCE: 10

Thr Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr
        35

<210> SEQ ID NO 11
<211> LENGTH: 9
<212> TYPE: PRT
<213> ORGANISM: Mouse

<400> SEQUENCE: 11

Gly Gly Gly Thr Lys Leu Glu Ile Lys
1               5

<210> SEQ ID NO 12
<211> LENGTH: 118
<212> TYPE: PRT
<213> ORGANISM: Mouse

<400> SEQUENCE: 12

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Asp
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Val Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Tyr Val Asn Tyr Asp Tyr Tyr Thr Met Asp Cys Trp Gly Gln Gly Thr
            100                 105                 110

Ser Val Thr Val Ser Ser
        115

<210> SEQ ID NO 13
<211> LENGTH: 8
<212> TYPE: PRT
<213> ORGANISM: Mouse

<400> SEQUENCE: 13

Gly Tyr Thr Phe Thr Asn Asp Gly
1               5

<210> SEQ ID NO 14
<211> LENGTH: 8
<212> TYPE: PRT
<213> ORGANISM: Mouse

<400> SEQUENCE: 14

Ile Asn Thr Asn Thr Gly Glu Pro
1               5

<210> SEQ ID NO 15
<211> LENGTH: 13
<212> TYPE: PRT
<213> ORGANISM: Mouse

<400> SEQUENCE: 15

Cys Tyr Val Asn Tyr Asp Tyr Tyr Thr Met Asp Cys Trp
1               5                   10

<210> SEQ ID NO 16
<211> LENGTH: 25
<212> TYPE: PRT
<213> ORGANISM: Mouse

<400> SEQUENCE: 16

Gln Ile Gln Leu Val Gln Ser Gly Pro Glu Leu Lys Lys Pro Gly Glu
1               5                   10                  15

Thr Val Lys Ile Ser Cys Lys Ala Ser
            20                  25

<210> SEQ ID NO 17
<211> LENGTH: 17
<212> TYPE: PRT
<213> ORGANISM: Mouse

```
<400> SEQUENCE: 17

Met Asn Trp Val Lys Gln Ala Pro Gly Lys Gly Leu Lys Trp Met Gly
1               5                   10                  15

Trp


<210> SEQ ID NO 18
<211> LENGTH: 37
<212> TYPE: PRT
<213> ORGANISM: Mouse

<400> SEQUENCE: 18

Thr Tyr Val Glu Glu Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe
        35


<210> SEQ ID NO 19
<211> LENGTH: 10
<212> TYPE: PRT
<213> ORGANISM: Mouse

<400> SEQUENCE: 19

Gly Gln Gly Thr Ser Val Thr Val Ser Ser
1               5                   10


<210> SEQ ID NO 20
<211> LENGTH: 108
<212> TYPE: PRT
<213> ORGANISM: Mouse

<400> SEQUENCE: 20

Gln Val Val Leu Thr Gln Ser Pro Ala Ile Met Ser Ala Ser Leu Gly
1               5                   10                  15

Asp Arg Val Thr Met Thr Cys Thr Ala Ser Ser Ser Val Ile Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Thr Leu Ala Ser Gly Val Pro Pro Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Leu Gln Tyr His Arg Ser Pro
                85                  90                  95

Arg Thr Phe Gly Gly Gly Thr Lys Leu Glu Ile Lys
            100                 105


<210> SEQ ID NO 21
<211> LENGTH: 7
<212> TYPE: PRT
<213> ORGANISM: Mouse

<400> SEQUENCE: 21

Ser Ser Val Ile Ser Thr Tyr
1               5


<210> SEQ ID NO 22
<211> LENGTH: 3
```

<212> TYPE: PRT
<213> ORGANISM: Mouse

<400> SEQUENCE: 22

Ser Thr Ser
1

<210> SEQ ID NO 23
<211> LENGTH: 9
<212> TYPE: PRT
<213> ORGANISM: Mouse

<400> SEQUENCE: 23

Leu Gln Tyr His Arg Ser Pro Arg Thr
1               5

<210> SEQ ID NO 24
<211> LENGTH: 26
<212> TYPE: PRT
<213> ORGANISM: Mouse

<400> SEQUENCE: 24

Gln Val Val Leu Thr Gln Ser Pro Ala Ile Met Ser Ala Ser Leu Gly
1               5                   10                  15

Asp Arg Val Thr Met Thr Cys Thr Ala Ser
            20                  25

<210> SEQ ID NO 25
<211> LENGTH: 17
<212> TYPE: PRT
<213> ORGANISM: Mouse

<400> SEQUENCE: 25

Leu His Trp Tyr Gln Gln Lys Pro Gly Ser Ser Pro Lys Leu Trp Ile
1               5                   10                  15

Tyr

<210> SEQ ID NO 26
<211> LENGTH: 36
<212> TYPE: PRT
<213> ORGANISM: Mouse

<400> SEQUENCE: 26

Thr Leu Ala Ser Gly Val Pro Pro Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35

<210> SEQ ID NO 27
<211> LENGTH: 10
<212> TYPE: PRT
<213> ORGANISM: Mouse

<400> SEQUENCE: 27

Phe Gly Gly Gly Thr Lys Leu Glu Ile Lys
1               5                   10

<210> SEQ ID NO 28
<211> LENGTH: 118
<212> TYPE: PRT
<213> ORGANISM: Mouse

<400> SEQUENCE: 28

```
Gln Ile Gln Leu Val Gln Ser Gly Pro Glu Val Lys Lys Pro Gly Glu
1               5                   10                  15

Thr Val Lys Ile Ser Cys Lys Ala Ser Gly Tyr Thr Phe Thr Asn Gln
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Thr Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Tyr Val Asn Tyr Asp Tyr Tyr Thr Met Asp Phe Trp Gly Gln Gly Thr
            100                 105                 110

Ser Val Thr Val Ser Ser
        115
```

<210> SEQ ID NO 29
<211> LENGTH: 8
<212> TYPE: PRT
<213> ORGANISM: Mouse

<400> SEQUENCE: 29

```
Gly Tyr Thr Phe Thr Asn Gln Gly
1               5
```

<210> SEQ ID NO 30
<211> LENGTH: 8
<212> TYPE: PRT
<213> ORGANISM: Mouse

<400> SEQUENCE: 30

```
Ile Asn Thr Asn Thr Gly Glu Pro
1               5
```

<210> SEQ ID NO 31
<211> LENGTH: 11
<212> TYPE: PRT
<213> ORGANISM: Mouse

<400> SEQUENCE: 31

```
Tyr Val Asn Tyr Asp Tyr Tyr Thr Met Asp Phe
1               5                   10
```

<210> SEQ ID NO 32
<211> LENGTH: 25
<212> TYPE: PRT
<213> ORGANISM: Mouse

<400> SEQUENCE: 32

```
Gln Ile Gln Leu Val Gln Ser Gly Pro Glu Val Lys Lys Pro Gly Glu
1               5                   10                  15

Thr Val Lys Ile Ser Cys Lys Ala Ser
            20                  25
```

<210> SEQ ID NO 33
<211> LENGTH: 17
<212> TYPE: PRT
<213> ORGANISM: Mouse

<400> SEQUENCE: 33

Met Asn Trp Val Lys Gln Ala Pro Gly Lys Gly Leu Lys Trp Met Gly
1               5                   10                  15

Trp

<210> SEQ ID NO 34
<211> LENGTH: 38
<212> TYPE: PRT
<213> ORGANISM: Mouse

<400> SEQUENCE: 34

Thr Tyr Thr Glu Glu Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe Cys
        35

<210> SEQ ID NO 35
<211> LENGTH: 11
<212> TYPE: PRT
<213> ORGANISM: Mouse

<400> SEQUENCE: 35

Trp Gly Gln Gly Thr Ser Val Thr Val Ser Ser
1               5                   10

<210> SEQ ID NO 36
<211> LENGTH: 108
<212> TYPE: PRT
<213> ORGANISM: Mouse

<400> SEQUENCE: 36

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Tyr Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys
            100                 105

<210> SEQ ID NO 37
<211> LENGTH: 7
<212> TYPE: PRT
<213> ORGANISM: Mouse

<400> SEQUENCE: 37

Ser Ser Val Tyr Ser Thr Tyr
1               5

<210> SEQ ID NO 38
<211> LENGTH: 3

<212> TYPE: PRT
<213> ORGANISM: Mouse

<400> SEQUENCE: 38

Ser Thr Ser
1

<210> SEQ ID NO 39
<211> LENGTH: 11
<212> TYPE: PRT
<213> ORGANISM: Mouse

<400> SEQUENCE: 39

Cys His Gln Tyr His Arg Ser Pro Arg Thr Phe
1 5 10

<210> SEQ ID NO 40
<211> LENGTH: 26
<212> TYPE: PRT
<213> ORGANISM: Mouse

<400> SEQUENCE: 40

Gln Ile Val Leu Thr Gln Ser Pro Ala Ile Met Ser Ala Ser Leu Gly
1 5 10 15

Glu Arg Val Thr Met Thr Cys Thr Ala Ser
20 25

<210> SEQ ID NO 41
<211> LENGTH: 17
<212> TYPE: PRT
<213> ORGANISM: Mouse

<400> SEQUENCE: 41

Leu His Trp Tyr Gln Gln Lys Pro Gly Ser Ser Pro Lys Leu Trp Ile
1 5 10 15

Tyr

<210> SEQ ID NO 42
<211> LENGTH: 35
<212> TYPE: PRT
<213> ORGANISM: Mouse

<400> SEQUENCE: 42

Asn Leu Ala Ser Gly Val Pro Ala Arg Phe Ser Gly Ser Gly Ser Gly
1 5 10 15

Thr Ser Tyr Ser Leu Thr Ile Ser Ser Met Glu Ala Glu Asp Ala Ala
20 25 30

Thr Tyr Tyr
35

<210> SEQ ID NO 43
<211> LENGTH: 9
<212> TYPE: PRT
<213> ORGANISM: Mouse

<400> SEQUENCE: 43

Gly Gly Gly Thr Lys Leu Glu Ile Lys
1 5

<210> SEQ ID NO 44
<211> LENGTH: 118
<212> TYPE: PRT
<213> ORGANISM: Mouse

<400> SEQUENCE: 44

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Ser Phe Thr Asn Ser
20 25 30

Gly Met Asn Trp Val Lys Glu Ala Pro Gly Lys Gly Leu Lys Trp Met
35 40 45

Gly Trp Ile Asn Thr Asn Thr Gly Glu Pro Thr Tyr Ala Glu Glu Phe
50 55 60

Met Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Tyr Val Asn Tyr Asp Tyr Tyr Thr Ile Asp Tyr Trp Gly Gln Gly Thr
100 105 110

Ser Val Thr Val Ser Ser
115

<210> SEQ ID NO 45
<211> LENGTH: 8
<212> TYPE: PRT
<213> ORGANISM: Mouse

<400> SEQUENCE: 45

Gly Tyr Ser Phe Thr Asn Ser Gly
1 5

<210> SEQ ID NO 46
<211> LENGTH: 8
<212> TYPE: PRT
<213> ORGANISM: Mouse

<400> SEQUENCE: 46

Ile Asn Thr Asn Thr Gly Glu Pro
1 5

<210> SEQ ID NO 47
<211> LENGTH: 13
<212> TYPE: PRT
<213> ORGANISM: Mouse

<400> SEQUENCE: 47

Cys Tyr Val Asn Tyr Asp Tyr Tyr Thr Ile Asp Tyr Trp
1 5 10

<210> SEQ ID NO 48
<211> LENGTH: 25
<212> TYPE: PRT
<213> ORGANISM: Mouse

<400> SEQUENCE: 48

Gln Ile Gln Leu Val Gln Ser Gly Pro Glu Leu Lys Lys Pro Gly Glu
1 5 10 15

Thr Val Lys Ile Ser Cys Lys Ala Ser
20 25

<210> SEQ ID NO 49
<211> LENGTH: 17
<212> TYPE: PRT
<213> ORGANISM: Mouse

<400> SEQUENCE: 49

Met Asn Trp Val Lys Glu Ala Pro Gly Lys Gly Leu Lys Trp Met Gly
1               5                   10                  15

Trp

<210> SEQ ID NO 50
<211> LENGTH: 37
<212> TYPE: PRT
<213> ORGANISM: Mouse

<400> SEQUENCE: 50

Thr Tyr Ala Glu Glu Phe Met Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe
        35

<210> SEQ ID NO 51
<211> LENGTH: 10
<212> TYPE: PRT
<213> ORGANISM: Mouse

<400> SEQUENCE: 51

Gly Gln Gly Thr Ser Val Thr Val Ser Ser
1               5                   10

<210> SEQ ID NO 52
<211> LENGTH: 108
<212> TYPE: PRT
<213> ORGANISM: Mouse

<400> SEQUENCE: 52

Gln Val Val Leu Thr Gln Ser Pro Ala Ile Met Ser Ala Ser Leu Gly
1               5                   10                  15

Glu Arg Val Thr Met Thr Cys Thr Ala Ser Ser Ser Val Ile Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Ile Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Leu Gln Tyr His Arg Ser Pro
                85                  90                  95

Arg Thr Phe Gly Gly Gly Thr Lys Leu Glu Ile Lys
            100                 105

<210> SEQ ID NO 53
<211> LENGTH: 7
<212> TYPE: PRT
<213> ORGANISM: Mouse

<400> SEQUENCE: 53

Ser Ser Val Ile Ser Ser Tyr
1               5

<210> SEQ ID NO 54
<211> LENGTH: 3

-continued

```
<212> TYPE: PRT
<213> ORGANISM: Mouse

<400> SEQUENCE: 54

Ser Thr Ser
1


<210> SEQ ID NO 55
<211> LENGTH: 11
<212> TYPE: PRT
<213> ORGANISM: Mouse

<400> SEQUENCE: 55

Cys Leu Gln Tyr His Arg Ser Pro Arg Thr Phe
1               5                   10


<210> SEQ ID NO 56
<211> LENGTH: 26
<212> TYPE: PRT
<213> ORGANISM: Mouse

<400> SEQUENCE: 56

Gln Val Val Leu Thr Gln Ser Pro Ala Ile Met Ser Ala Ser Leu Gly
1               5                   10                  15

Glu Arg Val Thr Met Thr Cys Thr Ala Ser
            20                  25


<210> SEQ ID NO 57
<211> LENGTH: 17
<212> TYPE: PRT
<213> ORGANISM: Mouse

<400> SEQUENCE: 57

Leu His Trp Tyr Gln Gln Lys Pro Gly Ser Ser Pro Lys Leu Trp Ile
1               5                   10                  15

Tyr


<210> SEQ ID NO 58
<211> LENGTH: 35
<212> TYPE: PRT
<213> ORGANISM: Mouse

<400> SEQUENCE: 58

Ile Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr
        35


<210> SEQ ID NO 59
<211> LENGTH: 9
<212> TYPE: PRT
<213> ORGANISM: Mouse

<400> SEQUENCE: 59

Gly Gly Gly Thr Lys Leu Glu Ile Lys
1               5


<210> SEQ ID NO 60
<211> LENGTH: 118
<212> TYPE: PRT
<213> ORGANISM: Mouse
```

<400> SEQUENCE: 60

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Ala Phe Thr Asn Asp
20 25 30

Gly Met Asn Trp Val Lys Gln Ala Pro Gly Lys Gly Leu Lys Trp Met
35 40 45

Gly Trp Ile Asn Thr Asn Thr Gly Glu Pro Thr Tyr Ala Glu Glu Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Tyr Val Asn Tyr Asp Tyr Tyr Thr Met Asp Cys Trp Gly Gln Gly Thr
100 105 110

Ser Val Thr Val Ser Ser
115

<210> SEQ ID NO 61
<211> LENGTH: 8
<212> TYPE: PRT
<213> ORGANISM: Mouse

<400> SEQUENCE: 61

Gly Tyr Ala Phe Thr Asn Asp Gly
1 5

<210> SEQ ID NO 62
<211> LENGTH: 8
<212> TYPE: PRT
<213> ORGANISM: Mouse

<400> SEQUENCE: 62

Ile Asn Thr Asn Thr Gly Glu Pro
1 5

<210> SEQ ID NO 63
<211> LENGTH: 13
<212> TYPE: PRT
<213> ORGANISM: Mouse

<400> SEQUENCE: 63

Cys Tyr Val Asn Tyr Asp Tyr Tyr Thr Met Asp Cys Trp
1 5 10

<210> SEQ ID NO 64
<211> LENGTH: 25
<212> TYPE: PRT
<213> ORGANISM: Mouse

<400> SEQUENCE: 64

Gln Ile Gln Leu Val Gln Ser Gly Pro Glu Leu Lys Lys Pro Gly Glu
1 5 10 15

Thr Val Lys Ile Ser Cys Lys Ala Ser
20 25

<210> SEQ ID NO 65
<211> LENGTH: 17
<212> TYPE: PRT
<213> ORGANISM: Mouse

<400> SEQUENCE: 65

Met Asn Trp Val Lys Gln Ala Pro Gly Lys Gly Leu Lys Trp Met Gly
1               5                   10                  15

Trp

<210> SEQ ID NO 66
<211> LENGTH: 37
<212> TYPE: PRT
<213> ORGANISM: Mouse

<400> SEQUENCE: 66

Thr Tyr Ala Glu Glu Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe
        35

<210> SEQ ID NO 67
<211> LENGTH: 10
<212> TYPE: PRT
<213> ORGANISM: Mouse

<400> SEQUENCE: 67

Gly Gln Gly Thr Ser Val Thr Val Ser Ser
1               5                   10

<210> SEQ ID NO 68
<211> LENGTH: 521
<212> TYPE: DNA
<213> ORGANISM: Mouse

<400> SEQUENCE: 68
caagttgttc tcacccagtc tccagcaatc atgtctgcat ctctagggga acgggtcacc 60
atgacctgca ctgccagctc aagtgtaatt tccagttatt tgcactggta ccagcagaag 120
ccaggatcct cccccaaact ctggatttat agcacatcca ccctggcttc tggagtccca 180
gctcgcttca gtggcagtgg gtctgggacc tcttactctc tcacaatcag cagcatggag 240
gctgaagatg ctgccactta ttactgcctc cagtatcatc gttccccacg gacgttcggt 300
ggaggcacca agctggaaat caaacgggct gatgctgcac caactgtatc catcttccca 360
ccatccagtg agcagttaac atctggaggt gcctcagtcg tgtgcttctt gaacaacttc 420
taccccaaag acatcaatgt caagtggaag attgatggca gtgaacgaca aaatggcgtc 480
ctgaacagtt ggactgatca ggacagcaaa gacagcacaa g 521

<210> SEQ ID NO 69
<211> LENGTH: 527
<212> TYPE: DNA
<213> ORGANISM: Mouse

<400> SEQUENCE: 69
cagatccagt tggtgcagtc tggacctgag ctgaagaagc ctggagagac agtcaagatc 60
tcctgcaagg cttctgggta taccttcaca aacgatggaa tgaactgggt gaaacaggct 120
ccaggaaagg gtttaaagtg gatgggctgg ataaacacca acactggaga gccaacatat 180
gttgaagagt tcaagggacg gtttgccttc tctttagaaa cctctgccag cactgcctat 240
ttgcagatca acaacctcaa aatgaggac acggctacat atttctgtta tgttaactac 300
gattattata ctatggactg ctggggtcaa ggaacctcag tcaccgtctc ctcagccaaa 360
acgacacccc catctgtcta tccactggcc cctggatctg ctgcccaaac taactccatg 420
gtgaccctgg gatgcctggt caagggctat ttccctgagc cagtgacagt gacctggaac 480
tctggatccc tgtccagcgg tgtgcacacc ttcccagcts tcctaag 527

<210> SEQ ID NO 70
<211> LENGTH: 521
<212> TYPE: DNA
<213> ORGANISM: Mouse

<400> SEQUENCE: 70
caagttgttc tcacccagtc tccagcaatc atgtctgcat ctctagggga tcgggtcacc 60
atgacctgca ctgccagctc aagtgtaatt tccacttact tgcactggta tcagcagaag 120
ccaggatcct cccccaaact ctggatttat agcacatcca ccctggcttc tggagtccca 180
cctcgcttca gtggcagtgg gtctgggacc tcttactctc tcacaatcag cagcatggag 240
gctgaagatg ctgccactta ttactgcctc cagtatcacc gttccccacg gacgttcggt 300
ggaggcacca agctggaaat caaacgggct gatgctgcac caactgtatc catcttccca 360
ccatccagtg agcagttaac atctggaggt gcctcagtcg tgtgcttctt gaacaacttc 420
taccccaaag acatcaatgt caagtggaag attgatggca gtgaacgaca aaatggcgtc 480
ctgaacagtt ggactgatca ggacagcaaa gacagcacaa g 521

<210> SEQ ID NO 71
<211> LENGTH: 527
<212> TYPE: DNA
<213> ORGANISM: Mouse

<400> SEQUENCE: 71
cagatccagt tggtgcagtc tggacctgag gtgaagaagc ctggagagac agtcaagatc 60
tcctgcaagg cttctgggta taccttcaca aaccaaggaa tgaactgggt gaaacaggct 120
ccaggaaagg gtttaaagtg gatgggctgg ataaacacca acactggaga gccaacatat 180
actgaagagt tcaagggacg gtttgccttc tctttagaaa cctctgccag cactgcctat 240
ttgcagatca acaacctcaa aaatgaggac acggctacat atttctgtta tgttaactac 300
gattattata ctatggactt ctggggtcaa ggaacctcgg tcaccgtctc ctcagccaaa 360
acaacagccc catcggtcta tccactggcc cctgtgtgtg gagatacaac tggctcctcg 420
gtgactctag gatgcctggt caagggttat ttccctgagc cagtgacctt gacctggaac 480
tctggatccc tgtccagtgg tgtgcacacc ttcccagcts tcctaag 527

<210> SEQ ID NO 72
<211> LENGTH: 521
<212> TYPE: DNA
<213> ORGANISM: Mouse

<400> SEQUENCE: 72
caaattgttc tcacccagtc tccagcaatc atgtctgctt ctctagggga acgggtcacc 60
atgacctgca ctgccagctc aagtgtatat tccacttact tgcactggta ccagcagaag 120
ccaggatcct cccccaaact ctggatttat agcacatcca acctggcttc tggagtccca 180
gctcgcttca gtggcagtgg gtctgggacc tcttactctc tcacaatcag cagcatggag 240
gctgaagatg ctgccactta ttactgccac cagtatcatc gttccccacg gacgttcggt 300

```
ggaggcacca agctggaaat caaacgggct gatgctgcac caactgtatc catcttccca    360

ccatccagtg agcagttaac atctggaggt gcctcagtcg tgtgcttctt gaacaacttc    420

taccccaaag acatcaatgt caagtggaag attgatggca gtgaacgaca aaatggcgtc    480

ctgaacagtt ggactgatca ggacagcaaa gacagcacaa g                        521
```

<210> SEQ ID NO 73
<211> LENGTH: 527
<212> TYPE: DNA
<213> ORGANISM: Mouse

<400> SEQUENCE: 73

```
cagatccagt tggtacagtc tggacctgag ctgaagaagc ctggagagac agtcaagatc     60

tcctgcaagg cttctgggta ttccttcaca aactctggaa tgaactgggt gaaagaggct    120

ccaggaaagg gtttaaagtg gatgggctgg ataaacacca acactggaga gccaacatat    180

gctgaagaat tcatgggacg gtttgccttc tctttggaaa cctctgccag cactgcctat    240

ttgcagatca acaacctcaa aaatgaagac acggctacat atttctgtta tgttaactac    300

gattactata ctatagacta ctggggtcaa ggaacctcag tcaccgtctc ctcagccaaa    360

acgacacccc catctgtcta tccactggcc cctggatctg ctgcccaaac taactccatg    420

gtgaccctgg gatgcctggt caagggctat ttccctgagc cagtgacagt gacctggaac    480

tctggatccc tgtccagcgg tgtgcacacc ttcccagcts tcctaag                  527
```

<210> SEQ ID NO 74
<211> LENGTH: 419
<212> TYPE: DNA
<213> ORGANISM: Mouse

<400> SEQUENCE: 74

```
cactggtacc agcagaagcc aggatcctcc cccaaactct ggatttatag cacatccatc     60

ctggcttctg gagtcccagc tcgcttcagt ggcagtgggt ctgggacctc ttactctctc    120

acaatcagca gcatggaggc tgaagatgct gccacttatt actgcctcca gtatcatcgt    180

tccccacgga cgttcggtgg aggcaccaag ctggaaatca aacgggctga tgctgcacca    240

actgtatcca tcttcccacc atccagtgag cagttaacat ctggaggtgc ctcagtcgtg    300

tgcttcttga acaacttcta ccccaaagac atcaatgtca agtggaagat tgatggcagt    360

gaacgacaaa atggcgtcct gaacagttgg actgatcagg acagcaaaga cagcacaag     419
```

<210> SEQ ID NO 75
<211> LENGTH: 527
<212> TYPE: DNA
<213> ORGANISM: Mouse

<400> SEQUENCE: 75

```
cagatccagt tggtgcagtc tggacctgag ctgaagaagc ctggagagac agtcaagatc     60

tcctgcaagg cttctgggta tgccttcaca aacgatggaa tgaactgggt gaaacaggct    120

ccaggaaagg gtttaaagtg gatgggctgg ataaacacca acactggaga gccaacatat    180

gctgaagagt tcaagggacg gtttgccttc tctttagaaa cctctgccag cactgcctat    240

ttgcagatca acaacctcaa aaatgaggac acggctacat atttctgtta tgttaactac    300

gattattata ctatggactg ctggggtcaa ggaacctcag tcaccgtctc ctcagccaaa    360

acgacacccc catctgtcta tccactggcc cctggatctg ctgcccaaac taactccatg    420

gtgaccctgg gatgcctggt caagggctat ttccctgagc cagtgacagt gacctggaac    480
```

tctggatccc tgtccagcgg tgtgcacacc ttcccagcts tcctaag 527

<210> SEQ ID NO 76
<211> LENGTH: 20
<212> TYPE: DNA
<213> ORGANISM: Artificial Sequence
<220> FEATURE:
<223> OTHER INFORMATION: synthetic primer

<400> SEQUENCE: 76
ggtgcagatt ttcagcttcc 20

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
gtgctgtctt tgctgtcctg 20

<210> SEQ ID NO 78
<211> LENGTH: 17
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (1)..(1)
<223> OTHER INFORMATION: b = c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: variation
<222> LOCATION: (6)..(7)
<223> OTHER INFORMATION: y = c or t
<220> FEATURE:
<221> NAME/KEY: variation
<222> LOCATION: (11)..(11)
<223> OTHER INFORMATION: k = g or t
<220> FEATURE:
<221> NAME/KEY: variation
<222> LOCATION: (16)..(16)
<223> OTHER INFORMATION: r = a or g

<400> SEQUENCE: 78
btnctyytct kcctgrt 17

<210> SEQ ID NO 79
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (4)..(4)
<223> OTHER INFORMATION: s = c or g
<220> FEATURE:
<221> NAME/KEY: variation
<222> LOCATION: (11)..(11)
<223> OTHER INFORMATION: m = a or c

<400> SEQUENCE: 79
tggstgtgga mcttgctatt 20

<210> SEQ ID NO 80
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (5)..(5)
<223> OTHER INFORMATION: s = c or g

<400> SEQUENCE: 80
aggasagctg ggaaggtgtg 20

<210> SEQ ID NO 81
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (3)..(3)
<223> OTHER INFORMATION: w = a or t
<220> FEATURE:
<221> NAME/KEY: variation
<222> LOCATION: (4)..(4)
<223> OTHER INFORMATION: k = g or t
<220> FEATURE:
<221> NAME/KEY: variation
<222> LOCATION: (6)..(6)
<223> OTHER INFORMATION: r = a or g
<220> FEATURE:
<221> NAME/KEY: variation
<222> LOCATION: (7)..(7)
<223> OTHER INFORMATION: s = c or g
<220> FEATURE:
<221> NAME/KEY: variation
<222> LOCATION: (9)..(9)
<223> OTHER INFORMATION: k = g or t
<220> FEATURE:
<221> NAME/KEY: variation
<222> LOCATION: (15)..(15)
<223> OTHER INFORMATION: k = g or t
<220> FEATURE:
<221> NAME/KEY: variation
<222> LOCATION: (16)..(16)
<223> OTHER INFORMATION: y = c or t

<400> SEQUENCE: 81
ctwkgrstkc tgctkytctg 20

<210> SEQ ID NO 82
<211> LENGTH: 20
<212> TYPE: DNA
<213> ORGANISM: Artificial Sequence
<220> FEATURE:
<223> OTHER INFORMATION: synthetic primer

<400> SEQUENCE: 82
cctgttaggc tgttggtgct 20

<210> SEQ ID NO 83
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (1)..(1)
<223> OTHER INFORMATION: r = a or g
<220> FEATURE:
<221> NAME/KEY: variation
<222> LOCATION: (2)..(2)
<223> OTHER INFORMATION: k = g or t
<220> FEATURE:
<221> NAME/KEY: variation
<222> LOCATION: (5)..(5)
<223> OTHER INFORMATION: r = a or g
<220> FEATURE:
<221> NAME/KEY: variation
<222> LOCATION: (8)..(8)
<223> OTHER INFORMATION: r = a or g
<220> FEATURE:
<221> NAME/KEY: variation
<222> LOCATION: (11)..(11)
<223> OTHER INFORMATION: r = a or g

<400> SEQUENCE: 83
rkcarcarct rcaggtgtcc 20

<210> SEQ ID NO 84
<211> LENGTH: 25
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (3)..(3)
<223> OTHER INFORMATION: y = c or t
<220> FEATURE:
<221> NAME/KEY: variation
<222> LOCATION: (4)..(4)
<223> OTHER INFORMATION: w = a or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: variation
<222> LOCATION: (11)..(11)
<223> OTHER INFORMATION: m = a or c
<220> FEATURE:
<221> NAME/KEY: variation
<222> LOCATION: (13)..(13)
<223> OTHER INFORMATION: w = a or t
<220> FEATURE:
<221> NAME/KEY: variation
<222> LOCATION: (22)..(22)
<223> OTHER INFORMATION: k = g or t

<400> SEQUENCE: 84
ccywntttta mawggtgtcc aktgt 25

<210> SEQ ID NO 85
<211> LENGTH: 21
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (11)..(11)
<223> OTHER INFORMATION: r = a or g
<220> FEATURE:
<221> NAME/KEY: variation
<222> LOCATION: (18)..(18)
<223> OTHER INFORMATION: b = c, g, or t

<400> SEQUENCE: 85
ggatggagct rtatcatbct c 21

<210> SEQ ID NO 86

<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (2)..(2)
<223> OTHER INFORMATION: r = a or g
<220> FEATURE:
<221> NAME/KEY: variation
<222> LOCATION: (8)..(8)
<223> OTHER INFORMATION: m = a or c
<220> FEATURE:
<221> NAME/KEY: variation
<222> LOCATION: (10)..(10)
<223> OTHER INFORMATION: y = c or t
<220> FEATURE:
<221> NAME/KEY: variation
<222> LOCATION: (13)..(14)
<223> OTHER INFORMATION: h = a, c, or t

<400> SEQUENCE: 86
grtctttmty tthhtcctgt ca 22

<210> SEQ ID NO 87
<211> LENGTH: 21
<212> TYPE: DNA
<213> ORGANISM: Artificial Sequence
<220> FEATURE:
<223> OTHER INFORMATION: synthetic primer
<220> FEATURE:
<221> NAME/KEY: variation
<222> LOCATION: (1)..(1)
<223> OTHER INFORMATION: v = a, c, or g
<220> FEATURE:
<221> NAME/KEY: variation
<222> LOCATION: (6)..(6)
<223> OTHER INFORMATION: w = a or t
<220> FEATURE:
<221> NAME/KEY: variation
<222> LOCATION: (7)..(8)
<223> OTHER INFORMATION: m = a or c
<220> FEATURE:
<221> NAME/KEY: variation
<222> LOCATION: (17)..(17)
<223> OTHER INFORMATION: w = a or t
<220> FEATURE:
<221> NAME/KEY: variation
<222> LOCATION: (20)..(20)
<223> OTHER INFORMATION: s = c or g

<400> SEQUENCE: 87
vccttwmmtg gtatccwgts t 21

<210> SEQ ID NO 88
<211> LENGTH: 426
<212> TYPE: DNA
<213> ORGANISM: Artificial Sequence
<220> FEATURE:
<223> OTHER INFORMATION: human-mouse sequence

<400> SEQUENCE: 88
gccgccacca tggcatgccc tggcttcctg tgggcacttg tgatctccac ctgtcttgaa 60
ttttccatgg ctcaggtgca gctggtgcaa tctgggtctg agttgaagaa gcctggggcc 120
tcagtgaagg tttcctgcaa ggcttctggg tataccttca caaaccaagg aatgaattgg 180
gtgcgacagg cccctggaca agggcttgag tggatgggat ggataaacac caacactgga 240
gagccaacgt atgcccaggg cttcacagga cggtttgtct tctccttgga cacctctgtc 300
agcacggcat atctgcagat cagcagccta aaggctgagg acactgccgt gtattactgt 360

```
tatgtcaatt acgattatta tactatggac ttctgggggc aagggaccac ggtcaccgtc    420

tcctca                                                               426


<210> SEQ ID NO 89
<211> LENGTH: 118
<212> TYPE: PRT
<213> ORGANISM: Artificial Sequence
<220> FEATURE:
<223> OTHER INFORMATION: human-mouse sequence

<400> SEQUENCE: 89

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Gln
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Tyr Val Asn Tyr Asp Tyr Tyr Thr Met Asp Phe Trp Gly Gln Gly Thr
            100                 105                 110

Thr Val Thr Val Ser Ser
        115


<210> SEQ ID NO 90
<211> LENGTH: 396
<212> TYPE: DNA
<213> ORGANISM: Artificial Sequence
<220> FEATURE:
<223> OTHER INFORMATION: human-mouse sequence

<400> SEQUENCE: 90

gccgccacca tggcatgccc tggcttcctg tgggcacttg tgatctccac ctgtcttgaa     60

ttttccatgg ctgacatcca gatgacccag tctccatcct ccctgtctgc atctgtagga    120

gacagagtca ccatcacttg ccgggcaagt tcaagtgtaa tttccactta cttaaattgg    180

tatcagcaga aaccagggaa agcccctaag ctcctgatct atagcacatc cagtttgcaa    240

agtggggtcc catcaaggtt cagtggcagt ggatctggga cagatttcac tctcaccatc    300

agcagtctgc aacctgaaga ttttgcaact tactactgtc tccagtatca ccgttcccca    360

cggacgttcg gcggagggac caaggtggag atcaaa                              396


<210> SEQ ID NO 91
<211> LENGTH: 108
<212> TYPE: PRT
<213> ORGANISM: Artificial Sequence
<220> FEATURE:
<223> OTHER INFORMATION: human-mouse sequence

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ile Ser Thr
            20                  25                  30
```

-continued

```
Tyr Leu Asn Trp Tyr Gln Gln Lys Pro Gly Lys Ala Pro Lys Leu Leu
        35                  40                  45

Ile Tyr Ser Thr Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gln Tyr His Arg Ser Pro
                85                  90                  95

Arg Thr Phe Gly Gly Gly Thr Lys Val Glu Ile Lys
            100                 105
```

<210> SEQ ID NO 92
<211> LENGTH: 426
<212> TYPE: DNA
<213> ORGANISM: Artificial Sequence
<220> FEATURE:
<223> OTHER INFORMATION: human-mouse sequence

<400> SEQUENCE: 92

```
gccgccacca tggcatgccc tggcttcctg tgggcacttg tgatctccac ctgtcttgaa     60

ttttccatgg ctcagatcca gttggtgcag tctggacctg agctgaagaa gcctggagag    120

acagtcaaga tctcctgcaa ggcttctggg tataccttca caaaccaagg aatgaactgg    180

gtgaaacagg ctccaggaaa gggtttaaag tggatgggct ggataaacac caacactgga    240

gagccaacat atactgccga tttcacagga cggtttgcct tctctttaga aacctctgtg    300

agcactgcct atttgcagat caactccctc aaagctgagg acacggctac atatttctgt    360

tatgtcaatt acgattatta tactatggac ttctggggtc aaggaaccct ggtcaccgtc    420

tcctca                                                               426
```

<210> SEQ ID NO 93
<211> LENGTH: 118
<212> TYPE: PRT
<213> ORGANISM: Artificial Sequence
<220> FEATURE:
<223> OTHER INFORMATION: human-mouse sequence

<400> SEQUENCE: 93

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Gln
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Thr Ala Asp Phe
    50                  55                  60

Thr Gly Arg Phe Ala Phe Ser Leu Glu Thr Ser Val Ser Thr Ala Tyr
65                  70                  75                  80

Leu Gln Ile Asn Ser Leu Lys Ala Glu Asp Thr Ala Thr Tyr Phe Cys
                85                  90                  95

Tyr Val Asn Tyr Asp Tyr Tyr Thr Met Asp Phe Trp Gly Gln Gly Thr
            100                 105                 110

Leu Val Thr Val Ser Ser
        115
```

<210> SEQ ID NO 94
<211> LENGTH: 396
<212> TYPE: DNA

<213> ORGANISM: Artificial Sequence
<220> FEATURE:
<223> OTHER INFORMATION: human-mouse sequence

<400> SEQUENCE: 94
gccgccacca tggcatgccc tggcttcctg tgggcacttg tgatctccac ctgtcttgaa 60
ttttccatgg ctgacgttca gctcacccag tctccaagca tcatgtctgc atctctaggg 120
gatcgggtca ccatgacctg cactgccagc tcaagtgtaa tttccactta cttgcactgg 180
tatcagcaga agccaggatc ctcccccaaa ctctggattt atagcacatc caccctggct 240
tctggagtcc caagccgctt cagtggcagt gggtctggga ccgactactc tctcacaatc 300
agcagcatgg agcctgaaga tgctgccact tattactgcc tccagtatca ccgttcccca 360
cggacgttcg gtggaggcac caaggtggaa atcaaa 396

<210> SEQ ID NO 95
<211> LENGTH: 108
<212> TYPE: PRT
<213> ORGANISM: Artificial Sequence
<220> FEATURE:
<223> OTHER INFORMATION: human-mouse sequence

<400> SEQUENCE: 95

Asp Val Gln Leu Thr Gln Ser Pro Ser Ile Met Ser Ala Ser Leu Gly
1               5                   10                  15

Asp Arg Val Thr Met Thr Cys Thr Ala Ser Ser Ser Val Ile Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Thr Leu Ala Ser Gly Val Pro Pro Arg Phe Ser
    50                  55                  60

Gly Ser Gly Ser Gly Thr Asp Tyr Ser Leu Thr Ile Ser Ser Met Glu
65                  70                  75                  80

Pro Glu Asp Ala Ala Thr Tyr Tyr Cys Leu Gln Tyr His Arg Ser Pro
                85                  90                  95

Arg Thr Phe Gly Gly Gly Thr Lys Val Glu Ile Lys
            100                 105

<210> SEQ ID NO 96
<211> LENGTH: 2161
<212> TYPE: DNA
<213> ORGANISM: Artificial Sequence
<220> FEATURE:
<223> OTHER INFORMATION: human-mouse sequence

<400> SEQUENCE: 96
gccgccacca tggcatgccc tggcttcctg tgggcacttg tgatctccac ctgtcttgaa 60
ttttccatgg ctcagatcca gttggtgcag tctggacctg agctgaagaa gcctggagag 120
acagtcaaga tctcctgcaa ggcttctggg tataccttca caaaccaagg aatgaactgg 180
gtgaaacagg ctccaggaaa gggtttaaag tggatgggct ggataaacac caacactgga 240
gagccaacat atactgccga tttcacagga cggtttgcct tctctttaga aacctctgtg 300
agcactgcct atttgcagat caactccctc aaagctgagg acacggctac atatttctgt 360
tatgtcaatt acgattatta tactatggac ttctggggtc aaggaaccct ggtcaccgtc 420
tcctcaggtg agtgcggccg cgagcccaga cactggacgc tgaacctcgc ggacagttaa 480
gaacccaggg gcctctgcgc cctgggccca gctctgtccc acaccgcggt cacatggcac 540

-continued

```
cacctctctt gcagcctcca ccaagggccc atcggtcttc cccctggcac cctcctccaa    600

gagcacctct gggggcacag cggccctggg ctgcctggtc aaggactact tccccgaacc    660

ggtgacggtg tcgtggaact caggcgccct gaccagcggc gtgcacacct tcccggctgt    720

cctacagtcc tcaggactct actccctcag cagcgtggtg accgtgccct ccagcagctt    780

gggcacccag acctacatct gcaacgtgaa tcacaagccc agcaacacca aggtggacaa    840

gagagttggt gagaggccag cacagggagg gagggtgtct gctggaagcc aggctcagcg    900

ctcctgcctg gacgcatccc ggctatgcag tcccagtcca gggcagcaag gcaggccccg    960

tctgcctctt cacccggagg cctctgcccg ccccactcat gctcagggag agggtcttct   1020

ggctttttcc ccaggctctg ggcaggcacg ggctaggtgc ccctaaccca ggccctgcac   1080

acaaaggggc aggtgctggg ctcagacctg ccaagagcca tatccgggag gaccctgccc   1140

ctgacctaag cccaccccaa aggccaaact ctccactccc tcagctcgga caccttctct   1200

cctcccagat tccagtaact cccaatcttc tctctgcaga gcccaaatct tgtgacaaaa   1260

ctcacacatg cccaccgtgc ccaggtaagc cagcccaggc ctcgccctcc agctcaaggc   1320

gggacaggtg ccctagagta gcctgcatcc agggacaggc cccagccggg tgctgacacg   1380

tccacctcca tctcttcctc agcacctgaa ctcctggggg gaccgtcagt cttcctcttc   1440

cccccaaaac ccaaggacac cctcatgatc tcccggaccc ctgaggtcac atgcgtggtg   1500

gtggacgtga gccacgaaga ccctgaggtc aagttcaact ggtacgtgga cggcgtggag   1560

gtgcataatg ccaagacaaa gccgcgggag gagcagtaca acagcacgta ccgtgtggtc   1620

agcgtcctca ccgtcctgca ccaggactgg ctgaatggca aggagtacaa gtgcaaggtc   1680

tccaacaaag ccctcccagc ccccatcgag aaaaccatct ccaaagccaa aggtgggacc   1740

cgtggggtgc gagggccaca tggacagagg ccggctcggc ccaccctctg ccctgagagt   1800

gaccgctgta ccaacctctg tccctacagg gcagccccga gaaccacagg tgtacaccct   1860

gcccccatcc cgggaggaga tgaccaagaa ccaggtcagc ctgacctgcc tggtcaaagg   1920

cttctatccc agcgacatcg ccgtggagtg ggagagcaat gggcagccgg agaacaacta   1980

caagaccacg cctcccgtgc tggactccga cggctccttc ttcctctata gcaagctcac   2040

cgtggacaag agcaggtggc agcaggggaa cgtcttctca tgctccgtga tgcatgaggc   2100

tctgcacaac cactacacgc agaagagcct ctccctgtct ccgggtaaat gatgagctag   2160

c                                                                   2161
```

<210> SEQ ID NO 97
<211> LENGTH: 448
<212> TYPE: PRT
<213> ORGANISM: Artificial Sequence
<220> FEATURE:
<223> OTHER INFORMATION: human-mouse sequence

<400> SEQUENCE: 97

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Gln
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Thr Ala Asp Phe
    50                  55                  60

Thr Gly Arg Phe Ala Phe Ser Leu Glu Thr Ser Val Ser Thr Ala Tyr
```

-continued

```
65                  70                  75                  80

Leu Gln Ile Asn Ser Leu Lys Ala Glu Asp Thr Ala Thr Tyr Phe Cys
                85                  90                  95

Tyr Val Asn Tyr Asp Tyr Tyr Thr Met Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 98
<211> LENGTH: 931
<212> TYPE: DNA
<213> ORGANISM: Artificial Sequence
<220> FEATURE:
<223> OTHER INFORMATION: human-mouse sequence

<400> SEQUENCE: 98

```
gccgccacca tggcatgccc tggcttcctg tgggcacttg tgatctccac ctgtcttgaa     60
ttttccatgg ctgacgttca gctcacccag tctccaagca tcatgtctgc atctctaggg    120
gatcgggtca ccatgacctg cactgccagc tcaagtgtaa tttccactta cttgcactgg    180
tatcagcaga agccaggcag ctcccccaaa ctctggattt atagcacatc caccctggct    240
tctggagtcc caagccgctt cagtggcagt gggtctggga ccgactactc tctcacaatc    300
agcagcatgg agcctgaaga tgctgccact tattactgcc tccagtatca ccgttcccca    360
cggacgttcg gtggaggcac caaggtggaa atcaaacgta agtgcacttt gcggccgcta    420
ggaagaaact caaaacatca agattttaaa tacgcttctt ggtctccttg ctataattat    480
ctgggataag catgctgttt tctgtctgtc cctaacatgc cctgtgatta tccgcaaaca    540
acacacccaa gggcagaact ttgttactta aacaccatcc tgtttgcttc tttcctcagg    600
aactgtggct gcaccatctg tcttcatctt cccgccatct gatgagcagt tgaaatctgg    660
aactgcctct gttgtgtgcc tgctgaataa cttctatccc agagaggcca aagtacagtg    720
gaaggtggat aacgccctcc aatcgggtaa ctcccaggag agtgtcacag agcaggacag    780
caaggacagc acctacagcc tcagcagcac cctgacgctg agcaaagcag actacgagaa    840
acacaaagtc tacgcctgcg aagtcaccca tcagggcctg agctcgcccg tcacaaagag    900
cttcaacagg ggagagtgtt gatagttaac g                                   931
```

<210> SEQ ID NO 99
<211> LENGTH: 215
<212> TYPE: PRT
<213> ORGANISM: Artificial Sequence
<220> FEATURE:
<223> OTHER INFORMATION: human-mouse sequence

<400> SEQUENCE: 99

```
Asp Val Gln Leu Thr Gln Ser Pro Ser Ile Met Ser Ala Ser Leu Gly
1               5                   10                  15

Asp Arg Val Thr Met Thr Cys Thr Ala Ser Ser Ser Val Ile Ser Thr
            20                  25                  30

Tyr Leu His Trp Tyr Gln Gln Lys Pro Gly Ser Ser Pro Lys Leu Trp
        35                  40                  45

Ile Tyr Ser Thr Ser Thr Leu Ala Ser Gly Val Pro Pro Arg Phe Ser
    50                  55                  60

Gly Ser Gly Ser Gly Thr Asp Tyr Ser Leu Thr Ile Ser Ser Met Glu
65                  70                  75                  80

Pro Glu Asp Ala Ala Thr Tyr Tyr Cys Leu Gln Tyr His Arg Ser Pro
                85                  90                  95

Arg Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 100
<211> LENGTH: 931
<212> TYPE: DNA
<213> ORGANISM: Artificial Sequence
<220> FEATURE:
<223> OTHER INFORMATION: human-mouse sequence

<400> SEQUENCE: 100

```
gccgccacca tggcatgccc tggcttcctg tgggcacttg tgatctccac ctgtcttgaa     60

ttttccatgg ctgacatcca gatgacccag tctccatcct ccctgtctgc atctgtagga    120

gacagagtca ccatcacttg cagcgcgagt tcaagtgtaa tttccactta cttaaattgg    180

tatcagcaga aaccagggaa agcccctaag gtgctgatct acagcacatc cagcttgcac    240

agcggggtcc catcaaggtt cagtggaagt ggatctggga cagattttac tctgaccatc    300

agcagcctgc agcctgaaga tttcgcaaca tattactgtc tccagtatca ccgttcccca    360

cggacgttcg gccaagggac caaggtggaa atcaaacgta agtgcacttt gcggccgcta    420

ggaagaaact caaaacatca agattttaaa tacgcttctt ggtctccttg ctataattat    480

ctgggataag catgctgttt tctgtctgtc cctaacatgc cctgtgatta tccgcaaaca    540

acacacccaa gggcagaact ttgttactta aacaccatcc tgtttgcttc tttcctcagg    600

aactgtggct gcaccatctg tcttcatctt cccgccatct gatgagcagt tgaaatctgg    660

aactgcctct gttgtgtgcc tgctgaataa cttctatccc agagaggcca aagtacagtg    720

gaaggtggat aacgccctcc aatcgggtaa ctcccaggag agtgtcacag agcaggacag    780

caaggacagc acctacagcc tcagcagcac cctgacgctg agcaaagcag actacgagaa    840

acacaaagtc tacgcctgcg aagtcaccca tcagggcctg agctcgcccg tcacaaagag    900

cttcaacagg ggagagtgtt gatagttaac g                                   931
```

<210> SEQ ID NO 101
<211> LENGTH: 2155
<212> TYPE: DNA
<213> ORGANISM: Artificial Sequence
<220> FEATURE:
<223> OTHER INFORMATION: human-mouse sequence

<400> SEQUENCE: 101

```
gccgccacca tggcatgccc tggcttcctg tgggcacttg tgatctccac ctgtcttgaa     60

ttttccatgg ctcagatcca gttggtgcag tctggacctg aggtgaagaa gcctggagag    120

acagtcaaga tctcctgcaa ggcttctggg tataccttca caaaccaagg aatgaactgg    180

gtgaaacagg ctccaggaaa gggtttaaag tggatgggct ggataaacac caacactgga    240

gagccaacat atactgaaga gttcaaggga cggtttgcct tctctttaga aacctctgcc    300

agcactgcct atttgcagat caacaacctc aaaaatgagg acacggctac atatttctgt    360

tatgttaact acgattatta tactatggac ttctggggtc aaggaacctc ggtcaccgtc    420

tcctcaggtg agtgcggccg cgagcccaga cactggacgc tgaacctcgc ggacagttaa    480

gaacccaggg gcctctgcgc cctgggccca gctctgtccc acaccgcggt cacatggcac    540

cacctctctt gcagcctcca ccaagggccc atcggtcttc cccctggcac cctcctccaa    600
```

```
gagcacctct gggggcacag cggccctggg ctgcctggtc aaggactact tccccgaacc     660

ggtgacggtg tcgtggaact caggcgccct gaccagcggc gtgcacacct tcccggctgt     720

cctacagtcc tcaggactct actccctcag cagcgtggtg accgtgccct ccagcagctt     780

gggcacccag acctacatct gcaacgtgaa tcacaagccc agcaacacca aggtggacaa     840

gagagttggt gagaggccag cacagggagg gagggtgtct gctggaagcc aggctcagcg     900

ctcctgcctg gacgcatccc ggctatgcag tcccagtcca gggcagcaag gcaggccccg     960

tctgcctctt cacccggagg cctctgcccg ccccactcat gctcagggag agggtcttct    1020

ggctttttcc ccaggctctg ggcaggcacg ggctaggtgc ccctaaccca ggccctgcac    1080

acaaaggggc aggtgctggg ctcagacctg ccaagagcca tatccgggag gaccctgccc    1140

ctgacctaag cccaccccaa aggccaaact ctccactccc tcagctcgga caccttctct    1200

cctcccagat tccagtaact cccaatcttc tctctgcaga gcccaaatct tgtgacaaaa    1260

ctcacacatg cccaccgtgc ccaggtaagc cagcccaggc ctcgccctcc agctcaaggc    1320

gggacaggtg ccctagagta gcctgcatcc agggacaggc cccagccggg tgctgacacg    1380

tccacctcca tctcttcctc agcacctgaa ctcctggggg gaccgtcagt cttcctcttc    1440

cccccaaaac ccaaggacac cctcatgatc tcccggaccc ctgaggtcac atgcgtggtg    1500

gtggacgtga gccacgaaga ccctgaggtc aagttcaact ggtacgtgga cggcgtggag    1560

gtgcataatg ccaagacaaa gccgcgggag gagcagtaca acagcacgta ccgtgtggtc    1620

agcgtcctca ccgtcctgca ccaggactgg ctgaatggca aggagtacaa gtgcaaggtc    1680

tccaacaaag ccctcccagc ccccatcgag aaaaccatct ccaaagccaa aggtgggacc    1740

cgtggggtgc gagggccaca tggacagagg ccggctcggc ccaccctctg ccctgagagt    1800

gaccgctgta ccaacctctg tccctacagg gcagccccga gaaccacagg tgtacaccct    1860

gcccccatcc cgggaggaga tgaccaagaa ccaggtcagc ctgacctgcc tggtcaaagg    1920

cttctatccc agcgacatcg ccgtggagtg ggagagcaat gggcagccgg agaacaacta    1980

caagaccacg cctcccgtgc tggactccga cggctccttc ttcctctata gcaagctcac    2040

cgtggacaag agcaggtggc agcaggggaa cgtcttctca tgctccgtga tgcatgaggc    2100

tctgcacaac cactacacgc agaagagcct ctccctgtct ccgggtaaat gatga         2155


<210> SEQ ID NO 102
<211> LENGTH: 472
<212> TYPE: PRT
<213> ORGANISM: Artificial Sequence
<220> FEATURE:
<223> OTHER INFORMATION: human-mouse sequence

<400> SEQUENCE: 102

Ala Ala Thr Met Ala Cys Pro Gly Phe Leu Trp Ala Leu Val Ile Ser
1               5                   10                  15

Thr Cys Leu Glu Phe Ser Met Ala Gln Ile Gln Leu Val Gln Ser Gly
            20                  25                  30

Pro Glu Val Lys Lys Pro Gly Glu Thr Val Lys Ile Ser Cys Lys Ala
        35                  40                  45

Ser Gly Tyr Thr Phe Thr Asn Gln Gly Met Asn Trp Val Lys Gln Ala
    50                  55                  60

Pro Gly Lys Gly Leu Lys Trp Met Gly Trp Ile Asn Thr Asn Thr Gly
65                  70                  75                  80

Glu Pro Thr Tyr Thr Glu Glu Phe Lys Gly Arg Phe Ala Phe Ser Leu
                85                  90                  95
```

```
Glu Thr Ser Ala Ser Thr Ala Tyr Leu Gln Ile Asn Asn Leu Lys Asn
            100                 105                 110

Glu Asp Thr Ala Thr Tyr Phe Cys Tyr Val Asn Tyr Asp Tyr Tyr Thr
        115                 120                 125

Met Asp Phe Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 103
<211> LENGTH: 925
<212> TYPE: DNA
<213> ORGANISM: Artificial Sequence
<220> FEATURE:

<223> OTHER INFORMATION: human-mouse sequence

<400> SEQUENCE: 103
gccgccacca tggcatgccc tggcttcctg tgggcacttg tgatctccac ctgtcttgaa 60
ttttccatgg ctcaagttgt tctcacccag tctccagcaa tcatgtctgc atctctaggg 120
gatcgggtca ccatgacctg cactgccagc tcaagtgtaa tttccactta cttgcactgg 180
tatcagcaga agccaggctc ttcccccaaa ctctggattt atagcacatc caccctggct 240
tctggagtcc cacctcgctt cagtggcagt gggtctggga cctcttactc tctcacaatc 300
agcagcatgg aggctgaaga tgctgccact tattactgcc tccagtatca ccgttcccca 360
cggacgttcg gtggaggcac caagctggaa atcaaacgta agtgcacttt gcggccgcta 420
ggaagaaact caaaacatca agattttaaa tacgcttctt ggtctccttg ctataattat 480
ctgggataag catgctgttt tctgtctgtc cctaacatgc cctgtgatta tccgcaaaca 540
acacacccaa gggcagaact ttgttactta aacaccatcc tgtttgcttc tttcctcagg 600
aactgtggct gcaccatctg tcttcatctt cccgccatct gatgagcagt tgaaatctgg 660
aactgcctct gttgtgtgcc tgctgaataa cttctatccc agagaggcca aagtacagtg 720
gaaggtggat aacgccctcc aatcgggtaa ctcccaggag agtgtcacag agcaggacag 780
caaggacagc acctacagcc tcagcagcac cctgacgctg agcaaagcag actacgagaa 840
acacaaagtc tacgcctgcg aagtcaccca tcagggcctg agctcgcccg tcacaaagag 900
cttcaacagg ggagagtgtt gatag 925

<210> SEQ ID NO 104
<211> LENGTH: 239
<212> TYPE: PRT
<213> ORGANISM: Artificial Sequence
<220> FEATURE:
<223> OTHER INFORMATION: human-mouse sequence

<400> SEQUENCE: 104

```
Ala Ala Thr Met Ala Cys Pro Gly Phe Leu Trp Ala Leu Val Ile Ser
1               5                   10                  15

Thr Cys Leu Glu Phe Ser Met Ala Gln Val Val Leu Thr Gln Ser Pro
            20                  25                  30

Ala Ile Met Ser Ala Ser Leu Gly Asp Arg Val Thr Met Thr Cys Thr
        35                  40                  45

Ala Ser Ser Ser Val Ile Ser Thr Tyr Leu His Trp Tyr Gln Gln Lys
    50                  55                  60

Pro Gly Ser Ser Pro Lys Leu Trp Ile Tyr Ser Thr Ser Thr Leu Ala
65                  70                  75                  80

Ser Gly Val Pro Pro Arg Phe Ser Gly Ser Gly Ser Gly Thr Ser Tyr
                85                  90                  95

Ser Leu Thr Ile Ser Ser Met Glu Ala Glu Asp Ala Ala Thr Tyr Tyr
            100                 105                 110

Cys Leu Gln Tyr His Arg Ser Pro Arg Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175
```

-continued

| | | | | | | | | | | | | | | | |
|---|---|---|---|---|---|---|---|---|---|---|---|---|---|---|---|
| Asn | Ala | Leu | Gln | Ser | Gly | Asn | Ser | Gln | Glu | Ser | Val | Thr | Glu | Gln | Asp |
| | | | 180 | | | | | 185 | | | | | 190 | | |
| Ser | Lys | Asp | Ser | Thr | Tyr | Ser | Leu | Ser | Ser | Thr | Leu | Thr | Leu | Ser | Lys |
| | | 195 | | | | | 200 | | | | | 205 | | | |
| Ala | Asp | Tyr | Glu | Lys | His | Lys | Val | Tyr | Ala | Cys | Glu | Val | Thr | His | Gln |
| | 210 | | | | | 215 | | | | | 220 | | | | |
| Gly | Leu | Ser | Ser | Pro | Val | Thr | Lys | Ser | Phe | Asn | Arg | Gly | Glu | Cys | |
| 225 | | | | | 230 | | | | | 235 | | | | | |